(12) United States Patent
Lohray et al.

(10) Patent No.: US 7,348,342 B2
(45) Date of Patent: Mar. 25, 2008

(54) HETEROCYCLIC COMPOUNDS PROCESS FOR THEIR PREPARATION AND PHARMACEUTICAL COMPOSITIONS CONTAINING THEM AND THEIR USE IN MEDICINE

(75) Inventors: Braj B. Lohray, Gujarat (IN); Vidya B. Lohray, Gujarat (IN); Mukul R. Jain, Gujarat (IN); Gautam D. Patel, Gujaret (IN); Harikishore Pingali, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 33 days.

(21) Appl. No.: 10/509,894

(22) PCT Filed: Apr. 1, 2003

(86) PCT No.: PCT/IN03/00133

§ 371 (c)(1),
(2), (4) Date: Jul. 6, 2005

(87) PCT Pub. No.: WO03/087062

PCT Pub. Date: Oct. 23, 2003

(65) Prior Publication Data

US 2005/0277678 A1    Dec. 15, 2005

(30) Foreign Application Priority Data

Apr. 5, 2002   (IN)   ................................ 327/02

(51) Int. Cl.
*A61K 31/444* (2006.01)
*A61K 31/4439* (2006.01)
*A61K 31/426* (2006.01)
*A61K 31/421* (2006.01)
*A61K 31/42* (2006.01)
*A61K 31/4155* (2006.01)
*A61K 31/415* (2006.01)
*C07D 213/22* (2006.01)
*C07D 401/04* (2006.01)
*C07D 277/34* (2006.01)
*C07D 263/38* (2006.01)
*C07D 261/12* (2006.01)
*C07D 231/10* (2006.01)
*C07D 231/12* (2006.01)

(52) U.S. Cl. ............ 514/334; 514/341; 514/369; 514/376; 514/378; 514/406; 546/257; 546/275.4; 548/186; 548/232; 548/243; 548/365.7; 548/377.1

(58) Field of Classification Search ............ 514/334, 514/341, 369, 376, 378, 406; 546/257, 275.4; 548/186, 232, 243, 365.7, 377.1
See application file for complete search history.

(56) References Cited

U.S. PATENT DOCUMENTS

| 5,633,272 | A | 5/1997 | Talley |
| 5,859,257 | A | 1/1999 | Talley |
| 5,981,576 | A | 11/1999 | Belley |
| 5,985,902 | A | 11/1999 | Talley |
| 6,020,343 | A | 2/2000 | Belley |
| 6,169,188 | B1 | 1/2001 | Belley |
| 6,673,818 | B2 | 1/2004 | Brown |
| 6,699,884 | B2 | 3/2004 | Brown |
| 2003/0032657 | A1 | 2/2003 | Brown et al. |
| 2003/0114456 | A1 | 6/2003 | Rosales |
| 2003/0149078 | A1 | 8/2003 | Brown et al. |

FOREIGN PATENT DOCUMENTS

| DE | 3522230 A1 * | 1/1987 |
| EP | 1251126 A2 | 10/2002 |
| EP | 1251126 A3 | 10/2002 |
| WO | 01/83475 A1 | 11/2001 |
| WO | 03/087062 A3 | 10/2003 |
| WO | 03/087062 A3 | 11/2003 |

OTHER PUBLICATIONS

Indicates that CAS Abstract and Structure Findings are attached.*
Morissette et al. Advanced Drug Delivery Reviews 2004, 56, 275-300.*
International Search Report.
Puig et al. "Synthesis and biological evaluation of 3,4-diaryloxazolones: A new class of orally active cyclooxygenase-2 inhibitors" Journal of Medicinal Chemistry, vol. 43, No. 2, pp. 214-223 (2000).
Penning et al. "Synthesis and biological evaluation of the 1,5-diarylpyrazole class of cyclooxygenase-2 inhibitors: Identification of 4-[5-(4-methylphenyl)-3-(trifluoromethyl)-1H-pyrazol-1-yl]benzenesulfonamide (SC-58635, Celecoxib)" Journal of Medicinal Chemistry, vol. 40, No. 9, pp. 1347-1365 (1997).
Shin et al. "2,2-Dimethyl-4,5-diaryl-3(2H)furanone derivatives as selective cyclo-oxygenase-2 inhibitors" Bioorganic & Medicinal Chemistry Letters, vol. 11, No. 2, pp. 165-168 (2001).
Friesen et al. "2-Pyrindinyl-3-(4-methylsulfonyl)phenylpyridines: Selective and orally active cyclooxygenase-2 inhibitors" Bioorganic & Medicinal Chemistry Letters, vol. 8, No. 19, pp. 2777-2782 (1998).

* cited by examiner

Primary Examiner—Rebecca Anderson
Assistant Examiner—Jason M Nolan
(74) Attorney, Agent, or Firm—Nixon & Vanderhye P.C.

(57) ABSTRACT

We describe substituted benzenesulfoximine compounds having anti-inflammatory activity, processes for their preparation, pharmaceutical compositions containing them, and their use in the treatment of inflammatory diseases.

19 Claims, No Drawings

HETEROCYCLIC COMPOUNDS PROCESS FOR THEIR PREPARATION AND PHARMACEUTICAL COMPOSITIONS CONTAINING THEM AND THEIR USE IN MEDICINE

This application is the U.S. national phase of international application PCT/IN03/00133 filed on 1 Apr. 2003, which designated the US and claims priority of IN Application No. 327/MUM/2002 filed 5 Apr. 2002. The entire contents of these applications are incorporated herein by reference.

FIELD OF INVENTION

The present invention relates to novel compounds of general formula (I), their analogs, their derivatives, their tautomeric forms, their pharmaceutically acceptable salts, pharmaceutical compositions containing them, where G represents substituted or unsubstituted, single or fused groups selected from aryl group, heteroaryl or heterocyclic groups. Preferably, G represents the groups A, B, C, D, E & F as described below. The present invention also relates to a process of preparing compounds of general formula (I), their analogs, derivatives, their tautomeric forms, their pharmaceutically acceptable salts, pharmaceutical compositions containing them, and novel intermediates involved in their synthesis.

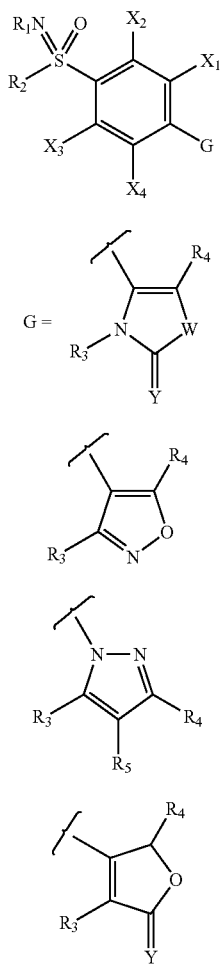

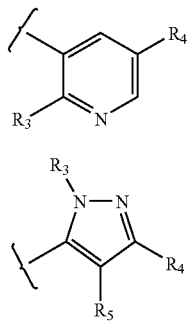

The compounds of the present invention are useful in the treatment of inflammatory diseases, preferably, wherein prostaglandins play a pathophysiological role. Their role have been implicated in a number of diseases which includes rheumatoid arthritis and osteoarthritis, pyrexia, asthma, bone resorption, cardiovascular diseases, dysmenorrhea, premature labour, nephritis, nephrosis, atherosclerosis, hypotension, shock, pain, cancer, and alzheimer disease.

BACKGROUND OF THE INVENTION

Inflammation is a disorder, which is characterized by redness, fever, swelling and pain. Prostaglandins play a major role in the inflammation process and inhibition of prostaglandin production, especially of $PGG_2$, $PGH_2$ and $PGE_2$ has been a common target to treat inflammation. However, NSAIDs that are commonly used to treat prostaglandin-induced pain and inflammation also effect other prostaglandin-regulated processes not associated with inflammation process. This leads to severe side effects including life threatening gastric ulcers dyspepsia & nephrotoxicity, thereby reducing their therapeutic use.

Previously, NSAIDs have been found to prevent the production of prostaglandins by inhibiting enzymes in the human arachidonic acid/prostaglandin pathway, including the enzyme cyclooxygenase (COX). In early 1990s, COX was demonstrated to exist as two distinct isoforms COX-1 and COX-2 (*PNAS* (1991) 88, 2692-96) and recently a third isoform COX-3 has been discovered from brain (*PNAS* (2002) 99, 13926-13931). COX-1 & COX-2 serve different physiological and pathophysiological functions. COX-1 is the constitutive isoform & is mainly responsible for the synthesis of cytoprotective prostaglandins in the GI tract and for the synthesis of thromboxane, which triggers platelet aggregation in blood platelets. COX-2 is believed to be an inducible isoform, which is stimulated in response to endotoxins, cytokines, and mitogens. Importantly, COX-2 plays a major role in prostaglandin biosynthesis in inflammatory cells (monocytes/macrophages) and in the central nervous system. (*Current Medicinal Chemistry* (2000) 7, 1041-62). The use of COX-2 as anti-cancer agents is discussed in *Curr Drug Targets* 2001 March; 2 (1):79-106. Hence, the difference in the function of COX-1 & COX-2 provides a goal of separating the toxicity, particularly related to the gastrointestinal tract from efficacy of NSAIDs by developing drugs that are selective COX-2 inhibitors as anti-inflammatory, analgesic, and/or antipyretic agents. It is believed that these compounds would have minimum or no GI & hematologic liabilities from COX-1 inhibition that plague almost all currently marketed NSAIDs, most of which inhibit both COX-1 & COX-2, with specificity for COX-1 inhibition greatly exceeding that for COX-2 inhibition. Celecoxib and Rofecoxib were the first two selective COX-2 inhibitors approved for selected markets for the treatment of certain inflammatory conditions.

Although, the concept of selectively inhibiting COX-2 in order to have better efficacy & safety looks quite very attractive, recent clinical studies have raised doubts about the long term efficacy of selective COX-2 inhibitors. Celecoxib was not found to be any better than other NSAIDs in long-term clinical study (*BMJ* (2002) 324, 1287-88). On the other hand highly selective COX-2 inhibitors produce adverse cardiovascular effects that are not seen in non-selective COX inhibitors (*Science* (2002) 296, 539-541; *JAMA* (2001) 268 954-959).

The references below disclose anti-inflammatory compounds that are selective COX-2 inhibitors. Increasing number of publications & patents emerging steadily indicates continuing efforts to find a safe and effective anti-inflammatory agent. Such novel compounds, their methods for preparation are described in EP1006114, EP1099695, EP418845, EP554829, EP0863134, EP0714895, EP0799523, GB2294879, U.S. Pat. No. 5,474,995, U.S. Pat. No. 5,486,534, U.S. Pat. No. 5,510,368, U.S. Pat. No. 5,686,460, U.S. Pat. No. 5,691,374, U.S. Pat. No. 5,710,140, U.S. Pat. No. 5,723,485, U.S. Pat. No. 5,776,967, U.S. Pat. No. 5,981,576, U.S. Pat. No. 5,922,742, U.S. Pat. No. 6,083,969, U.S. Pat. No. 6,071,954, U.S. Pat. No. 6,071,936, U.S. Pat. No. 6,133,292, U.S. Pat. No. 6,143,892, U.S. Pat. No. 6,274,590, WO9415932, WO9427980, WO9500501, WO9515315, WO9515316, WO9515317, WO9515318, WO9518799, WO9603387, WO9603392, WO9606840, WO9609304, WO9610012, WO9616934, WO9619469, WO9621667, WO9623786, WO9624585, WO9625405, WO9631509, WO9636623, WO9637467, WO9638418, WO9636617, WO9703667, WO9703953, WO9713755, WO9714691, WO9716435, WO9727181, WO9734882, WO9737984, WO9746524, WO97727181, WO9804527, WO9807425, WO9807714, WO9811080 WO9813483, WO9816227, WO9821195, WO9822442, WO9825896, WO9841511, WO9841516, WO9843966, WO9852940, WO9910331, WO9910332, WO9912930, WO9915503, WO9923087, WO9935130, WO0026216, WO0052008, WO0024719, WO0134577, WO0140216.

In addition to COX, the enzyme lipoxygenase (LOX) also plays an important role in inflammation, 5-LOX products such as LTB4, LTC4 and LTD4 are involved in a variety of pathological processes (*Pharmacol Rev* (2003), 55 195-227). Therefore, inhibition of 5-LOX activity may produce beneficial effects in inflammation. Studies have indicated that dual inhibitors of COX and LOX may have better safety profile (*Pharmacol Res* (2001), 43 429-436) than non-selective NSAIDs. The compounds of the present invention are useful in treating inflammatory conditions caused by increased activities of COX and/or LOX enzymes.

Cytokines are known to be involved in inflammatory processes. Tumor necrosis factor α(TNF-α) is described as a key proinflammatory mediator in autoimmune diseases. This 26 kDa enzyme is membrane associated until processed into a smaller (17 kDa) soluble form by TNF-α converting enzyme (TACE). The compounds of the present invention are also useful in the treatment of inflammatory diseases such as arthritis by inhibiting TNF-α, or TACE or by inhibiting the production of Tumor necrosis factor-α.

SUMMARY OF THE INVENTION

The present invention describes a group of novel compounds useful in the treatment of inflammatory diseases, cytokine related, specially, TNF-α mediated diseases, cyclooxygenase related diseases, like inflammation and pain. The novel compounds are defined by the general formula (I) wherein G represents substituted or unsubstituted, single or fused groups selcted from aryl group, heteroaryl or heterocyclic groups containing one or more heteroatom selected from O, S. N, preferably, G represents the groups A, B, C, D, E & F as described below:

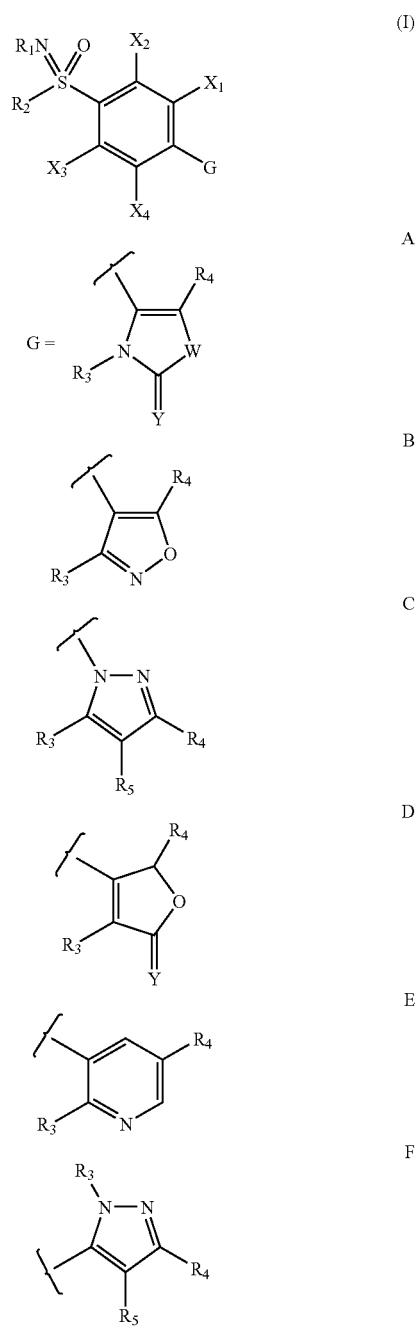

The compounds of the present invention are useful in the treatment of the human or animal body, in particular for the treatment of pain, fever or inflammation, to inhibit prostanoid-induced smooth muscle contraction or for the prevention of colorectal cancer. They are also useful for the relief of pain, fever and inflammation of a variety of conditions including rheumatic fever and neuropathic pain, symptoms associated with influenza or other viral infections, common cold, low back and neck pain, dysmenorrhoea, headache, toothache, sprains and strains, myostis, neuralgia, synovitis, bursitis, tendinitis, injuries following surgical and dental procedures, post-operative inflammation including ophthalmic surgery such as cataract and refractive surgery, menstrual cramps, premature labor, These compounds may also be used in the treatment of arthritis, such as rheumatoid arthritis, spondyloarthropathies, gouty arthritis, osteoarthritis, systemic lupus erythematosus and juvenile arthritis, skin inflammation disorders such as psoriasis, eczema, burning and dermatitis with better efficacy, potency and minimum toxic effects.

The main objective of the present invention thus is to provide novel compounds of general formula (I), their analogs, derivatives, their tautomeric forms, their pharmaceutically acceptable salts, their pharmaceutically acceptable solvates and pharmaceutical compositions containing them or their mixtures.

Another objective of the present invention is to provide a process for the preparation of novel compounds of general formula (I), their analogs, derivatives, their tautomeric forms, their pharmaceutically acceptable salts, pharmaceutically acceptable solvates and pharmaceutical compositions containing them.

The present invention also aims at providing pharmaceutical compositions containing compounds of general formula (I), their analogs, derivatives, their tautomeric forms, their pharmaceutically acceptable salts, solvates, and their mixtures having pharmaceutically acceptable carriers, solvents, diluents and other media normally employed in their manufacture.

The compounds of the present invention provides a method of treatment of cyclooxygenase mediated diseases, by administering a therapeutically effective & non-toxic amount of the compound of formula (I) or their pharmaceutically acceptable compositions to the mammals.

DETAILED DESCRIPTION OF THE INVENTION

The novel compounds of the present invention are defined by the general formula (I) wherein G represents substituted or unsubstituted, single or fused groups selcted from aryl group, heteroaryl or heterocyclic groups containing one or more heteroatom selected from O, S, N, preferably, G represents the groups A, B, C, D, E & F as described below:

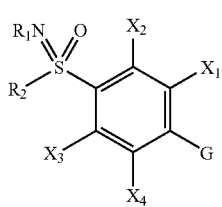

(I)

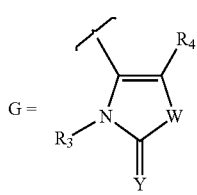

A

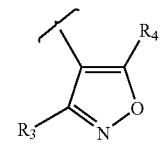

B

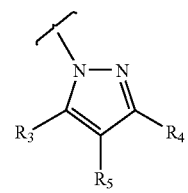

C

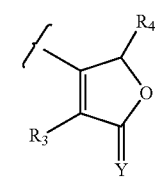

D

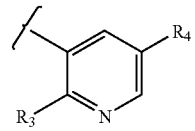

E

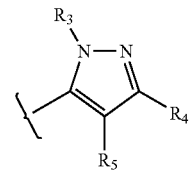

F where $R_1$ represents hydrogen, substituted or unsubstituted groups selected from alkyl, aralkyl, acyl, alkylsulfonyl, arylsulfonyl groups; $R_2$ represents alkyl, aralkyl, alkoxy or —NHR where R represents hydrogen or lower alkyl groups which may be suitably substituted;

$X_1$, $X_2$, $X_3$, $X_4$ may be same or different and represent hydrogen, cyano, nitro, halo, carboxyl, formyl, hydrazino, azido, amino, thio, hydroxy, or substituted or unsubstituted groups selected from alkyl which may be linear or branched, alkenyl cycloalkyl, alkoxy, cycloalkoxy, cycloalkoxyalkyl, haloalkoxy, hydroxyalkyl, alkoxyalkyl, thioalkyl, carboxyalkyl, haloalkyl, aminoalkyl, cyanoalkyl, alkylthio, alkylsulfinyl, alkylsulfonyl alkoxycarbonylalkyl, acyl, acyloxy, acyloxyalkyl, aralkyl, aryloxy, aralkoxy, aryloxyalkyl, aralkoxyalkyl, aralkenyl, acylamino, akylamino, dialkylamino, aralkylamino, alkoxyamino, hydroxylamino, alkoxycarbonyl, aralkoxycarbonyl, groups; two adjacent groups may form a methylenedioxy or a ethylenedioxy group; when G represents heterocycle "D", then at least one of the groups defined by $X_1$, $X_2$, $X_3$, $X_4$ is not hydrogen;

$R_3$ is selected from substituted or unsubstituted alkyl, substituted or unsubstituted single or fused groups selected from aryl, aralkenyl, heteroaryl or heterocyclic groups: $R_4$ and $R_5$ is selected from hydrogen atom, halogen atom, carboxy, substituted or unsubstituted groups selected from linear or branched alkyl, haloalkyl polyhaloalkyl, alkoxycarbonyl, hydroxyalkyl, alkoxyalkyl, phenyl groups; Y represents O or S; W represents O or S;

Suitable substituents on $R_3$ and $R_4$ may be selected from cyano, nitro, halo, carboxyl, hydrazino, azido, formyl, amino, thio, hydroxy, $ONO_2$, alkyl-$ONO_2$ or substituted or unsubstituted groups selected from alkyl which may be linear or branched, perhaloalkyl, alkoxy, hydrazinoalkyl, alkylhydrazido, acyl, acyloxy, oxo, carboxyalkyl, haloalkyl, aminoalkyl, haloalkoxy, hydroxyalkyl, alkoxyalkyl, thioalkyl, alkylthio, alkylsulfinyl, alkylsulfonyl, alkylsulfoximinyl, aryl, aralkyl, aryloxy, aralkyl, aryloxyalkyl, aralkoxyalkyl, aryloxycarbonyl, alkoxycarbonyl, aralkoxycarbonyl, alkoxycarbonylalkyl, amidino, carboxamidoalkyl, acylamino, cyanoamidino, cyanoalkyl, N-aminocarbonylalkyl, N-arylaminocarbonyl, carboxyalkylaminocarboxy, N-alkylamino, N,N-dialkylamino, N-arylamino, N-aralkylamino, N-alkyl-N-aralkylamino, N-alkyl-N-arylamino, N-alkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, arylthio, aralkylthio, N-alkylaminosulfonyl, N-arylaminosulfonyl, arylsulfonyl, N,N-dialkylaminosulfonyl, N-alkyl-N-arylaminosulfonyl, alkoxycarbonyl, aminocarbonyl, cycloalkyl, heterocyclic, heterocyclicalkyl, heteroaryl, heteroaralkyl, heteroaralkoxy, sulfamyl groups; two adjacent groups may form a methylenedioxy or a ethylenedioxy group;

Suitable substituents on $X_1$, $X_2$, $X_3$, $X_4$ may be selected from cyano, nitro, halo, carboxyl, hydrazino, azido, formyl, amino, thio, hydroxy or substituted or unsubstituted groups selected from alkyl which may be linear or branched, alkoxy, alkoxycarbonyl, acyl, acylamino, acyloxy, hydrazinoalkyl, alkylhydrazido, carboxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, alkoxycarbonyl, amidino groups;

Where the term "alkyl" is used anywhere in the specification, either alone or within other terms such as "haloalkyl", "hydroxyalkyl", "alkylthio", "alkylsulfonyl" etc. it includes linear or branched radicals having one to ten carbon atoms. More preferred alkyl radicals are "lower alkyl" radicals having one to six carbon atoms. Examples of such radicals include but not limited to methyl, ethyl, n-propyl, isopropyl, n-butyl, isobutyl, sec-butyl, tert-butyl, pentyl, iso-amyl, hexyl, isohexyl, heptyl, octyl etc. The term "alkenyl" includes linear or branched radicals having at least one carbon-carbon double bond of two to ten carbon atoms or, preferably, two to six carbon atoms. Examples of such radicals include ethenyl, n-propenyl, butenyl, and the like. The term "halo" means halogens such as fluorine, chlorine, bromine or iodine atoms. The term "haloalkyl" includes radicals wherein any one or more of the alkyl carbon atoms is substituted with halogen atoms as defined above. Examples include monohaloalkyl, dihaloalkyl, polyhaloalkyl and similar radicals. A monohaloalkyl radical, for example, may have either an iodo, bromo, chloro or fluoro atom within the radical. Dihalo and polyhaloalkyl radicals may have two or more of the same halo atoms or a combination or different halo radicals. The alkyl group in haloalkyl group is a lower alkyl group and is termed lower haloalkyl group. "Lower haloalkyl" includes radicals having 1-6 carbon atoms. Examples of haloalkyl radicals include fluoromethyl, difluoromethyl, trifluoromethyl, chloromethyl, dichloromethyl, trichloromethyl, trichloroethyl, pentafluoroethyl, difluorochloromethyl, dichlorofluoromethyl, difluoroethyl, difluoropropyl, and the likes. The term "hydroxyalkyl" includes linear or branched alkyl radicals having one to ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl, hydroxypentyl, and hydroxyhexyl.

The terms "alkoxy" and "alkoxyalkyl" includes linear or branched oxy-containing radicals each having alkyl portions of one to about ten carbon atoms, such as methoxy radical. Preferred alkoxy radicals are "lower alkoxy" radicals having one to six carbon atoms. Examples of such radicals include methoxy, ethoxy, propoxy, butoxy and tert-butoxy. The term "alkoxyalkyl" also includes alkyl radicals having two or more alkoxy radicals attached to the alkyl radical that is, to form monoalkoxyalkyl and dialkoxyalkyl radicals. Preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl, methoxypropyl and the like. The "alkoxy" or "alkoxyalkyl" radicals may further contain alkoxy substitution consisting of one or more halo atoms, such as fluoro, chloro or bromo, to provide "haloalkoxy" or "haloalkoxyalkyl" radicals. Examples of such radicals include fluoromethoxy, chloromethoxy, trifluoromethoxy, trifluoroethoxy, fluoroethoxy and the like.

The term "aryl", alone or in combination, includes carbocyclic aromatic system containing one, two or three rings wherein such rings may be attached together in a pendant manner or may be fused. The term "aryl" includes aromatic radicals such as phenyl, naphthyl, tetrahydronaphthyl, indane and biphenyl. The term "heterocyclic" includes saturated, partially saturated and unsaturated ring-shaped radicals, the heteroatoms selected from either nitrogen, sulfur and oxygen. Examples of saturated heterocyclic radicals include saturated 3 to 7 membered heterocyclic group containing one or more heteroatoms selected from N, O and S. Examples of such groups include but are not limited to aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxazepinyl, thiazepinyl, oxazolidinyl, thiazolidinyl and the like: examples of partially saturated heterocyclic radicals include dihydrothiophene, dihydropyran, dihydrofuran, dihydrothiazole and the like; the term "heteroaryl" includes unsaturated heterocyclic radicals. Examples of unsaturated heterocyclic radicals, also termed "heteroaryl" radicals include unsaturated 5 to 6 membered heteromonocyclic, fused polycyclic heteroaryl or fused polycyclic heterocycle groups containing one or more heteroatoms selected from O, N, S. Example of such groups include but not limited to pyrrolyl, pyrrolinyl, imidazolyl, pyrazolyl, 2-pyridyl, 3-pyridyl, 4-pyridyl, pyrimidyl, pyrazinyl, pyridazinyl, triazolyl, (e.g., 4H-1,2,4-triazolyl, 1H-1,2,3-tetrazolyl etc.), indolyl, isoindolyl, dihydroindolyl, benzofuryl, 2,3-dihydrobenzofuryl, chromanyl, benzopyran, thiochromanyl, benzothiopyran, benzodioxolyl, benzodioxanyl pyridyl, thienyl, benzothienyl, oxazolyl, benzimidazolyl, quinolyl, isoquinolyl, indazolyl, benzotriazolyl, tetrazolopyridazinyl, pyranyl, 2-furyl, 3-furyl, pthalazinyl, quinazolinyl, quinolinyl, isoquinolinyl, benzoxazolyl, benzoxadiazolyl, thiazolyl, thiadiazolyl, benzothiazolyl, benzothiadiazolyl, benzofuran, benzothiophene, and the like. The aforesaid "heterocyclic or heteroaryl group" may have 1 to 4 substituents such as lower alkyl, haloalkyl, dihaloalkyl, trihaloalkyl, hydroxy, oxo, amino and lower alkylamino, lower alkoxy, halo, lower thioalkyl, acyl, acylamino groups. Preferred heterocyclic radicals include five to ten membered fused or unfused radicals and more preferable examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, pyrazinyl, pthalazinyl, quinazolinyl, quinolinyl, isoquinolinyl, benzoxazolyl, benzothiazolyl, and the like.

The tem "hydrazino" used herein, either alone or in combination with other radicals, denotes —NHNH—, suitably substituted with other radicals, such as alkyl hydrazino, where an alkyl group, as defined above is attached to a hydrazino group.

The term "sulfonyl", used alone or in combination with other terms such as alkylsulfonyl, denotes respectively divalent radicals —$SO_2$—. "Alkylsulfonyl", includes alkyl radicals attached to a sulfonyl radical, where alkyl is defined as above. More preferred alkylsulfonyl radicals are lower alkylsulfonyl radicals having one to six carbon atoms. Examples of such lower alkylsulfonyl radicals include methylsulfonyl, ethylsulfonyl and propylsulfonyl. The term "arylsulfonyl" includes aryl radicals as defined above, attached to a sulfonyl radical. Examples of such radicals include phenylsulfonyl. The terms "sulfamyl," "aminosulfonyl" and "sulfonamidyl," whether alone or used with terms such as "N-alkylaminosulfonyl" and "N-arylaminosulfonyl", "N,N-dialkylaminosulfonyl", "N-alkyl-N-arylaminosulfonyl", denotes a sulfonyl radical substituted with an amine radical, forming a sulfonamide (—$SO_2NH_2$). The terms "N-arylaminosulfonyl" and "N,N-dialkylaminosulfonyl" denote sulfamyl radicals substituted, respectively with one alkyl radical, or two alkyl radicals. More preferred alkylaminosulfonyl radicals are "lower alkylaminosulfonyl" radicals having one to six carbon atoms. Examples of such lower alkylaminosulfonyl radicals include N-methylaminosulfonyl, N-ethylaminosulfonyl, N-methyl-N-ethylaminosulfonyl and the like. The terms "N-arylaminosulfonyl" and "N-alkyl-N-arylaminosulfonyl" denote sulfamyl radicals substituted respectively with one aryl radical or one alkyl and one aryl radical. Preferred N-alkyl-N-arylaminosulfonyl radicals are lower N-alkyl-N-arylsulfonyl radicals having alkyl radicals of one to six carbon atoms. Examples of such lower N-alkyl-N-arylsulfonyl radicals are N-ethyl-phenylaminosulfonyl and the like.

The terms "carboxy" or "carboxyl", whether used alone or with other terms, such as "carboxyalkyl", denotes —$CO_2H$. The terms "alkanoyl" or "acyl" include radicals derived from carboxylic acids and include but not limited to substituted or unsubstituted groups selected from formyl, acetyl, propionyl (propanoyl), butanoyl (butyryl), isobutanoyl (isobutyryl), valeryl (pentanoyl), isovaleryl, pivaloyl, hexanoyl, benzoyl or the like. The term "carbonyl" used either alone or with other terms, such as "alkylcarbonyl", denotes —(C=O)—. The term "alkylcarbonyl" includes radicals having a carbonyl radical substituted with an alkyl radical such as acyl or alkanoyl described above. The term "alkylcarbonylalkyl" denotes an alkyl radical substituted with an "alkylcarbonyl" radical. The term "alkoxycarbonyl" means a radical containing an alkoxy radical, as defined above, attached via an oxygen atom to a carbonyl radical. Preferably, "lower alkoxycarbonyl" includes alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" includes radicals having "alkoxycarbonyl", as defined above substituted to an alkyl radical. Preferred alkoxycarbonylalkyl radicals are "lower alkoxycarbonylalkyl" having lower alkoxycarbonyl radicals as defined above attached to one to six carbon atoms for example methoxycarbonylmethyl, tert-butoxycarbonylethyl, and methoxycarbonylethyl. The term "aminocarbonyl" when used separately or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", substituted or unsubstituted. The terms "N-alkylaminocarbonyl" and "N,N-dialkylaminocarbonyl" denote aminocarbonyl radicals which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "aminocarbonylalkyl" includes alkyl radicals substituted with aminocarbonyl radicals.

The term "amidino" denotes an —C(=NH)—$NH_2$ radical. The term "cyanoamidino" denotes an —C(=N—CN)—$NH_2$ radical. The term "heterocyclicalkyl" includes heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl, pyridylmethyl and thienylmethyl. The term "aralkyl" includes aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl, diphenylethyl and the like. The aryl in said aralkyl may be additionally substituted with halo, alkyl, alkoxy, haloalkyl, haloalkoxy, hydroxy, amino, acylamino, alkoxycarbonyl, alkylthio and the like. The terms benzyl and phenylmethyl are interchangeable. The term "cycloalkyl" includes radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl, cycloheptyl and the like. The term "cycloalkenyl" includes unsaturated cyclic radicals having three to ten carbon atoms, such as cyclobutenyl, cyclopentenyl, cyclohexenyl, cycloheptenyl and the like. The term "alkylthio" includes radicals containing a linear or branched alkyl radical attached to a divalent sulfur atom. Example of alkylthio are methylthio ($CH_3$—S—), ethylthio, butylthio, and the like. The term "alkylsulfinyl" includes radicals containing a linear or branched alkyl radical attached to a divalent-S(=O)-atom.

The term "aminoalkyl" includes alkyl radicals substituted with amino radicals. Preferred aminoalkyl radicals are "lower aminoalkyl" having one to six carbon atoms. Examples include aminomethyl, aminoethyl and aminobutyl. The term "alkylaminoalkyl" includes aminoalkyl radicals having the nitrogen atom substituted with at least one alkyl radical. Preferred alkylaminoalkyl radicals are "lower alkylaminoalkyl" having one to six carbon atoms attached to a lower aminoalkyl radical as described above. The terms "N-alkylamino" and "N,N-dialkylamino" denote amino groups which have been substituted with one alkyl radical and with two alkyl radicals, respectively. Preferred alkylamino radicals are "lower alkylamino" radicals having one or two alkyl radicals of one to six carbon atoms, attached to a nitrogen atom. Suitable "alkylamino" may be N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" denotes amino groups which have been substituted with one or two aralkyl radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical; respectively, to an amino group. The terms "N-arylaminoalkyl" and "N-aralkylaminoalkyl" denote amino groups which have been substituted with one aryl radical or one aralkyl radical, respectively, and having the amino group attached to an alkyl radical. Preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The terms "N-alkyl-N-arylaminoalkyl" and "N-aralkyl-N-alkylaminoalkyl" denotes N-alkyl-N-arylamino and N-alkyl-N-aralkylamino groups, respectively, and having the amino group attached to alkyl radicals. The term "acyl", whether used alone, or with another term such as "acylamino" denotes a radical provided by the residue after removal of hydroxyl from an organic acid. The term "acylamino" includes an amino radical substituted with an acyl group. Examples of an "acylamino" radical is acetylamino or acetamido ($CH_3C(=O)$—NH—) where the amine may be further substituted with alkyl, aryl, or aralkyl. The term "arylthio" includes aryl radicals of six to ten carbon atoms, attached to a divalent sulfur atom. An example of "arylthio" is phenylthio. The term "aralkylthio" includes aralkyl radicals as described above, attached to a divalent sulfur atom. An example of "aralkylthio" is benzylthio. The term "aryloxy" includes aryl radicals, as defined above, attached to an oxygen atom. Examples of such radicals include phenoxy. The term "aralkoxy" includes oxy-containing aralkyl radicals attached through an oxygen atom to other radicals. Preferred aralkoxy radicals are "lower aralkoxy" radicals having phenyl radicals attached to lower alkoxy radical as described above. The term "haloaralkyl" includes aryl radicals as defined above "carboxyhaloalkyl" includes carboxyalkyl radicals as defined above having halo radicals attached to the alkyl portion. The term "aralkenyl" includes aryl radicals attached to alkenyl radicals having two to ene carbon atoms, such as phenylbutenyl, and phenylethenyl or styryl.

Suitable groups and substituents on the groups may be selected from those described anywhere in the specification.

Particularly useful compounds according to the present invention includes 5-(4-Fluorophenyl)-1-(4-methylsulfoximinylphenyl)-3-trifluoromethyl-1H-pyrazole 5-(4-Chlorophenyl)-1-(4-methylsulfoximinylphenyl)-3-trifluoromethyl-1H-pyrazole 5-(4-Methylphenyl)-1-(4-methylsulfoximinylphenyl)-3-trifluoromethyl-1H-pyrazole 5-(4-Methoxyphenyl)-1-(4-methylsulfoximinylphenyl)-3-trifluoromethyl-1H-pyrazole 1-(4-methylsulfoximinylphenyl)-5-(4-n-propoxyphenyl)-3-trifluoromethyl-1H-pyrazole 5-(4-Ethoxyphenyl)-1-(4-methylsulfoximinylphenyl)-3-trifluoromethyl-1H-pyrazole 5-(4-Hydroxyphenyl)-1-(4-methylsulfoximinylphenyl)-3-trifluoromethyl-1H-pyrazole 5-(3-Chloro-4-fluorophenyl)-1-(4-methylsulfoximinylphenyl)-3-trifluoromethyl-1H-pyrazole 5-(3,4-Difluorophenyl)-1-(4-methylsulfoximinylphenyl)-3-trifluoromethyl-1H-pyrazole 5-(4-Fluoro-3-methylphenyl)-1-(4-methylsulfoximinylphenyl)-3-trifluoromethyl-1H-pyrazole 5-(4-Methoxy-3-methylphenyl)-1-(4-methylsulfoximinylphenyl)-3-trifluoromethyl-1H-pyrazole 5-(3-Chloro-4-methoxyphenyl)-1-(4-methylsulfoximinylphenyl)-3-trifluoromethyl-1H-pyrazole 5-(3-Bromo-4-methoxyphenyl)-1-(4-methylsulfoximinylphenyl)-3-trifluoromethyl-1H-pyrazole 5-(3-Fluoro-4-methoxyphenyl)-1-(4-methylsulfoximinylphenyl)-3-trifluoromethyl-1H-pyrazole 5-(3-Methoxy-4-methylphenyl)-1-(4-methylsulfoximinylphenyl)-3-trifluoromethyl-1H-pyrazole 1-(2-Fluoro-4-methylsulfoximinylphenyl)-5-(4-Methoxyphenyl)-3-trifluoromethyl-1H-pyrazole 1-(3Fluoro-4-methylsulfoximinylphenyl)-5-(4-Methoxyphenyl)-3-trifluoromethyl-1H-pyrazole 1-(4-Methylsulfoximinylphenyl)-5-phenyl-3-trifluoromethyl 1H-pyrazole 1-(4-Methylsulfoximinylphenyl)-5-(1-naphthyl)-3-trifluoromethyl-1H-pyrazole 5-(4-Methoxyphenyl)-3-methyl-1-(4-methylsulfoximinylphenyl)-1H-pyrazole 1-(4-Methylsulfoximinylphenyl)-5-(4-nitrophenyl)-3-trifluoromethyl-1H-pyrazole 5-(3-Methoxyphenyl)-1-(4-methylsulfoximinylphenyl)-3-trifluoromethyl-1H-pyrazole 5-(3,5-Difluoro-4-Methoxyphenyl)-1-(4-methylsulfoximinylphenyl)-3-trifluoromethyl-1H-pyrazole 5-(3-Hydroxy-4-methoxyphenyl)-1-(4-methylsulfoximinylphenyl)-3-trifluoromethyl-1H-pyrazole 5-(4-Methoxyphenyl)-1-(4-methylsulfoximinylphenyl)-1H-pyrazole-3-carboxylicacid 3-(Hydroxymethyl)-5-(4-Methoxyphenyl)-1-(4-methylsulfoximinylphenyl)-1H-pyrazole 5-(4-Methoxyphenyl)-1-(4-methylsulfoximinylphenyl)-1H-pyrazol-3-ylmethylhydrogen sulphate 5-{4-(2-Hydroxy-ethoxy)phenyl}-1-(4-methylsulfoximinylphenyl)-3-trifluoromethyl-1H-pyrazole 1-(4-Methylsulfoximinylphenyl)-5-(4-pyridyl)-3-trifluoromethyl-1H-pyrazole 1-(4-Methylsulfoximinylphenyl)-5-(3-pyridyl)-3-trifluoromethyl-1H-pyrazole 1-(4-Methylsulfoximinylphenyl)-5-(2-pyridyl)-3-trifluoromethyl-1H-pyrazole 5-(4-Isopropoxyphenyl)-1-(4-methylsulfoximinylphenyl)-3-trifluoromethyl-1H-pyrazole 1-(4-Methylsulfoximinylphenyl)-5-(2-thiophenyl)-3-trifluoromethyl-1H-pyrazole 5-(4-Methylsulfoxyminylphenyl)-1-phenyl-3-trifluoromethyl-1H-pyrazole. 1-(4-Methoxyphenyl)-5-(4-methylsulfoximinylphenyl)-3-trifluoromethyl-1H-pyrazole 5-Ethyl-4-(4-methylsulfoximinylphenyl)-3-phenyl-isoxazole 5-Methoxymethyl-4-(4-methylsulfoximinylphenyl)-3-phenyl-isoxazole 3-(4-Fluorophenyl)-5-methyl-4-(4-methylsulfoximinylphenyl)-isoxazole 3-(4-Chlorophenyl)-5-methyl-4-(4-methylsulfoximinylphenyl)-isoxazole 3-Ethyl-4-(4-methylsulfoximinylphenyl)-5-phenyl-isoxazole 5-Chloro-4-(4-methylsulfoximinylphenyl)-3-phenyl-isoxazole 5-methyl-4-(4-methylsulfoximinylphenyl)-3-phenyl-isoxazole 3-(4-Methoxyphenyl)-5-methyl-4-(4-methylsulfoximinylphenyl)-isoxazole 3-(3,4-Dichlorophenyl)-4-(3-fluoro-4-methylsulfoximinylphenyl)-5H-furan-2-one 3-(4-Chlorophenyl)-4-(3-fluoro-4-methylsulfoximinylphenyl)-5H-furan-2-one 3-Phenyl-4-(3-fluoro-4-methylsulfoximinylphenyl)-5H-furan-2-one 3-(3,4-Difluorophenyl)-4-(3-fluoro-4-methylsulfoximinylphenyl)-5H-furan-2-one 3-(3,4-Dimethoxyphenyl)-4-(3-fluoro-4-methylsulfoximinylphenyl)-5H-furan-2-one 3-(4-methoxyphenyl)-4-(3-fluoro-4-methylsulfoximinylphenyl)-5H-furan-2-one 3-(4-Methylphenyl)-4-(3-fluoro-4-methylsulfoximinylphenyl-5H-furan-2-one 5-Chloro-3-(4-methylsulfoximinylphenyl)-6'-methyl-[2,3']bipyridinyl 5-Chloro-3-(4-methylsulfoximinylphenyl)-[2,3']bipyridinyl 3-(3-Fluorophenyl)-4-(4-methylsulfoximinylphenyl)-3H-thiazol-2-one 3-(3,4-Dichlorophenyl)-4-(4-methylsulfoximinylphenyl)-3H-oxazol-2-one 3-(3,4-Dichlorophenyl)-4-(4-methylsulfoximinylphenyl)-3H-thiazol-2-one 3-(2-Fluorophenyl)-4-(4-methylsulfoximinylphenyl)-3H-oxazol-2-one 3-(4-Bromophenyl)-4-(4-methylsulfoximinylphenyl)-3H-oxazol-2-one 4-(4-Methylsulfoximinylphenyl)-3-phenyl-3H-oxazol-2-one 3-(3,4-Dichlorophenyl)-4-[4-(N-chloroacetyl)methylsulfoximinylphenyl]-3H-oxazol-2-one 3-(3,4-Dichlorophenyl)-4-[4-(N-acetyl)methylsulfoximinylphenyl]-3H-oxazol-2-one 3-(3,4-Dichlorophenyl)-4-[4-(N-methylsulfonyl)methylsulfoximinyl-phenyl]-3H-oxazol- 2-one 3-(3,4-Dichlorophenyl)-4-[4-{N-(4-methylphenyl) sulfonyl}-methylsulfoximinyl-phenyl]-3H-oxazol-2-one The present invention also provides methods for the preparation of novel compounds described in the general formula (I), their tautomeric forms, their derivatives, their analogs, their pharmaceutically acceptable salts and their pharmaceutically acceptable solvates, wherein all symbols are as defined earlier. The process comprising:

Oxidizing a compound of formula (P) to get a compound of formula (Q) which is iminated with suitable reagents get compound of formula (I) which may further be converted to their pharmaceutically acceptable salts, if desired.

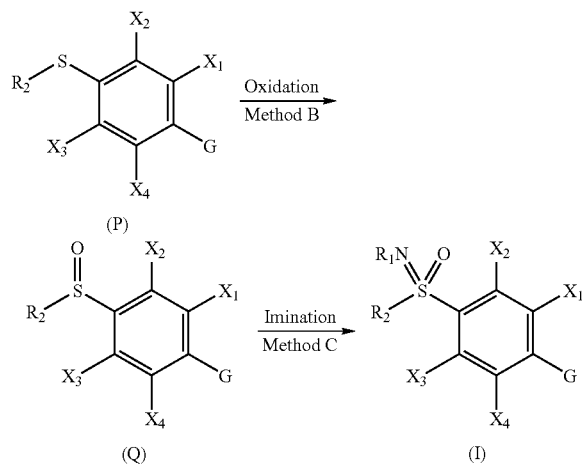

A detailed process with different G groups are outlined in the schemes:

Method B:

The mercapto compounds of formula P may be converted to the respective sulfoxides of formula Q by reacting with an oxidizing agent. Suitable oxidizing agents may be selected from but not limited to peroxides and peroxyacids and their salts. Suitable oxidizing agent is selected from $H_2O_2$, meta-peroxides of Na, K, and the like, oxone®, sodium perborate, sodium tungstate and the like, peracetic acid, m-chloroperbenzoic acid, magnesium monoperoxyphthalate, and the like. Suitable solvents are based on the oxidizing agents used and are selected from water, acetic acid, acetonitrile, dichloromethane, acetone, THF, methanol, ethanol and the like or a mixture thereof. Reaction temperature may range from −78° C. to 40° C., based on the solvent used.

Method C:

The sulfoxide compounds of formula Q may be converted to sulfoximine compounds of formula (I) by reacting with suitable iminating agents such as hydrazoic acid ($HN_3$) which may be generated by the reaction of $NaN_3$ with conc. sulfuric acid in solvents such as $CH_2Cl_2$, $CHCl_3$ and the like. Temperature in the range −10° C. to reflux temperature of the solvent(s) used may be used. Alternatively, sulfoxides of formula IV or V may be treated with O-substituted hydroxylamines, such as O-mesitylenesulfonylhydroxylamine (MSH), followed by a base such as KOH, NaOH, $NaHCO_3$ and the like. Solvents such as $CH_2Cl_2$, $CHCl_3$ may be used.

Scheme I

The compounds of general formula (IA) wherein all the symbols are as defined earlier, may be prepared by one or more routes or combinations of reactions outlined in Scheme I below which comprises:

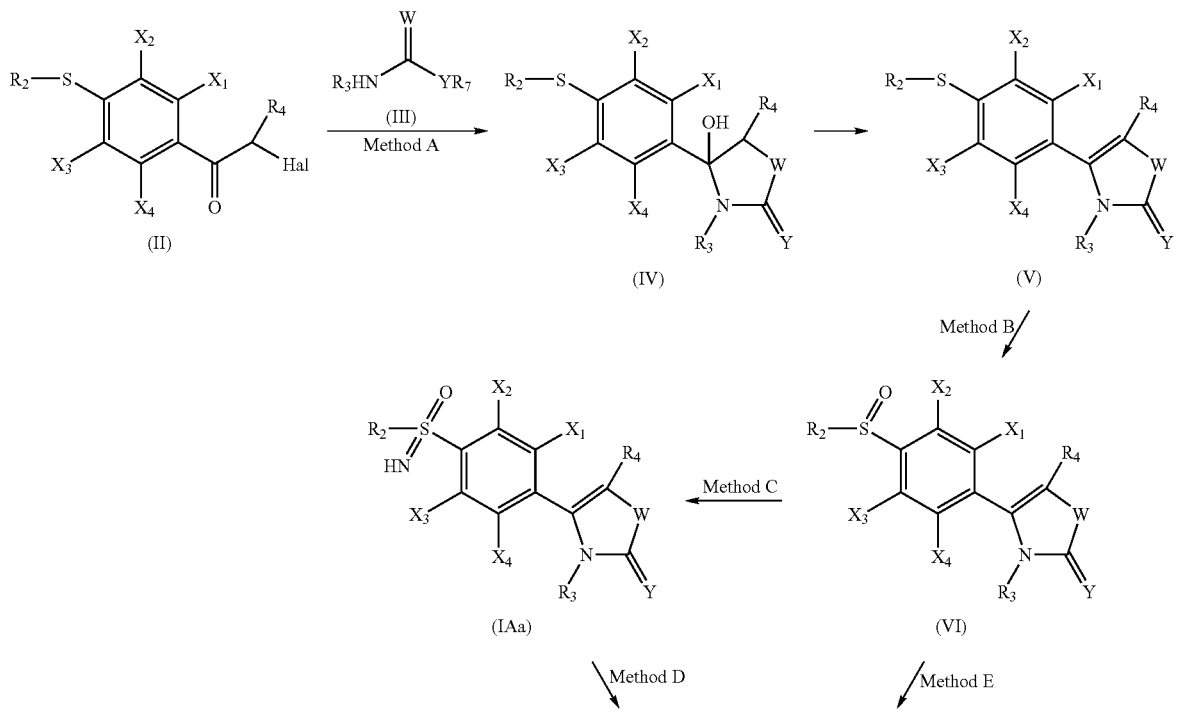

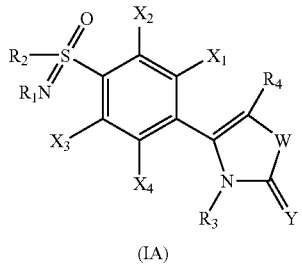

(IA)

i) Reacting a compound of formula II wherein, $R_2$, $R_4$, $X_1$, $X_2$, $X_3$, $X_4$ are as defined earlier and Hal represents a halogen atom such as chlorine, bromine or iodine atom with an aryl thiocarbamate III to yield a compound of formula V, after dehydration of the intermediate IV.

ii) Reacting the compound of formula V with an oxidizing compound such as $H_2O_2$, peracids and such other oxidizing agents to yield a sulfoxide of formula VI iii) Reacting the sulfoxide of formula VI an appropriate iminating agent such as $HN_3$, O-substituted hydroxylamines such as O-mesitylenesulfonyl hydroxylamine (MSH) and the like to yield sulfoxamine of formula (IAa);

iv) optionally, compound of formula (IAa) is converted to compound of formula (IA) by suitable agents to get appropriate $R_1$ group. Alternatively, the compound of formula VI may be converted to compound (IA) by treating with appropriate agents;

v) optionally, if desired, the compound of formula (IAa) or (IA) are converted to pharmaceutically acceptable salts;

The reactions described in the processes (i) to (v) outlined above may be performed by using the methods described herein:

Method A:

The haloketones of formula II may be converted to corresponding cyclic compounds of formula V by reacting with a compound of formula II, through an initial formation of a compound of formula IV, in a solvent such as an alcohol like methanol, ethanol, isopropanol and the like; acetone, THF, dioxane, acetonitrile, toluene, xylene and the like or a mixture thereof. Reaction temperature may range from ambient to reflux temperature of the solvent(s) used. The compounds of formula IV is converted to respective compound of formula V, by dehydration by refluxing in a suitable medium such as an aqueous alcoholic medium containing a mineral acid such as HCl or $H_2SO_4$, or $H_3PO_4$; organic acids such as PTSA may also be used in an organic solvent such as toluene, xylene and the like; organic acid such as acetic acid, propionic acid or trifluoroacetic acid may also be used.

Method B:

The mercapto compounds of formula V may be converted to the respective sulfoxides by reacting with an oxidizing agent. Suitable oxidizing agents may be selected from but not limited to peroxides and peroxyacids and their salts. Suitable oxidizing agent is selected from $H_2O_2$, meta-peroxides of Na, K, and the like, oxone®, sodium perborate, sodium tungstate and the like, peracetic acid, m-chloroperbenzoic acid, magnesium monoperoxyphthalate, and the like. Suitable solvents are based on the oxidizing agents used and are selected from water, acetic acid, acetonitrile, dichloromethane, acetone, THF, methanol, ethanol and the like or a mixture thereof. Reaction temperature may range from $-78°$ C. to $40°$ C., based on the solvent used.

Method C:

The sulfoxide compounds of formula VI may be converted to sulfoximine compounds by reacting with suitable iminating agents such as hydrazoic acid ($HN_3$) which may be generated by the reaction of $NaN_3$ with conc. sulfuric acid in solvents such as $CH_2Cl_2$, $CHCl_3$ and the like. Temperature in the range $-10°$ C. to reflux temperature of the solvent(s) used may be used. Alternatively, sulfoxides of formula IV or V may be treated with O-substituted hydroxylamines, such as O-mesitylenesulfonylhydroxylamine (MSH), followed by a base such as KOH, NaOH, $NaHCO_3$ and the like. Solvents such as $CH_2Cl_2$, $CHCl_3$ may be used.

Method D:

The sulfoximines of formula (IAa) may be converted to corresponding substituted compounds of formula (IA) by reaction with appropriate alkylating/acylating agents in the presence of a base. The alkylating/acylating agent depends on the desired group $R_1$ such as suitably substituted alkyl halides/acylhalides or acyl anhydrides. When $R_1$=Me, formic acid/formaldehyde mixture is used. Solvents used may be DMF, DMSO, acetone, THF, diaoxane, toluene, xylene and the like or a mixture thereof. Bases such as $K_2CO_3$, $Na_2CO_3$, Na, KI, nBuLi $Et_3N$ or a mixture thereof may be used. Reaction temperature may range from $0°$ C. to reflux temperature of the solvent(s) used.

Method E:

The sulfoxide compounds of formula VI may be directly converted to substituted sulfoximine compounds by reacting with suitable reagents such as Tosylazide, Chloramine T, in solvents such as ethanol, methanol and the like, followed by basification to yield $R_1$=Tosyl groups. Alternatively, reaction with arylamines in the presence of t-BuOCl gives N-arylsulfoximines.

Scheme II:

The compounds of general formula (IB) wherein all the symbols are as defined earlier may be prepared by one or more routes or combinations of reactions outlined in scheme II which comprises:

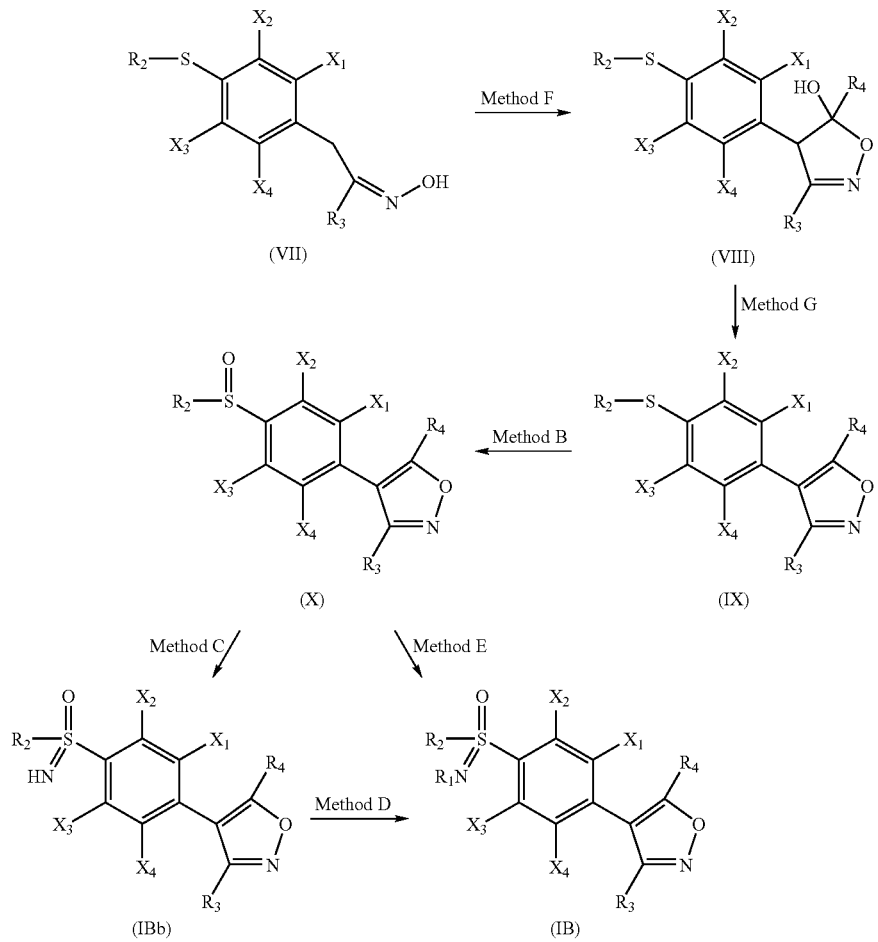

i) Reacting the compound of general formula VII with at least two equivalents of an appropriate base followed by treatment with an appropriate ester or anhydride to afford an alcohol of general formula VIII;
ii) heating the compound of general formula VIII in an appropriate solvent in the presence of appropriate acid to get compound of general formula IX.
iii) Oxidizing compound of formula IX with appropriate oxidizing agents to get a compound of general formula X;
iv) Reacting sulfoxide of formula X with appropriate agents to afford compound of general formula (IBb);
v) Optionally compound of formula X may be converted to compound of formula (IB) by suitable agents to get appropriate $R^1$ group. Alternatively, compound of formula (IBb) may be converted to compound of formula (IB) using appropriate agents.
vi) Optionally, if desired, compounds of formula (IBb) or (IB) are converted to pharmaceutically acceptable salts;

The reactions described in the processes outlined in the schemes II above may be performed by using the methods described herein:

Method F:

The oxime of formula VII may be converted to alcohol of formula VIII by reacting with two equivalents of a suitable base to produce a dianion which is further acylated. Bases such as n-BuLi, Sodium hydride, LDA, LiHMDS, NaH-MDS and the like or a mixture thereof may be used. Temperature in the range of −78° C. to ambient temperature may be used. Preferably, the dianion formation is done at −78° to −40° C. range. Suitable acylating agents are esters, anhydrides, acyl imidazoles and the like. The reaction is conducted under a blanket of inert atmosphere using inert gases like $N_2$, He or Ar. Anhydrous condition is very critical for the reaction to give good product and yield.

Method G:

The alcohol of formula VIII may be converted to isooxazole of formula IX by dehydration in the presence of an acid. Solvents such as ethanol, THF, toluene, xylene, and the like or a mixture thereof may be used. Suitable acids may, be PTSA, $H_2SO_4$, HCl, HBr, camphorsulfonic acid, pyridinium paratoluene sulfonic acid and the like. The amount acid used may be catalytic or substoichiometric or Stoichiometric to effect the dehydration. Temperature in the range of ambient to reflux temperature of the solvent(s) may be used.

Method B:

The mercapto compound of formula IX may be converted to sulfoxide of formula X by reacting with an oxidizing agent as described in Method B of scheme I earlier.

and the like, followed by basification to yield $R_1$=Tosyl groups. Alternatively, reaction with aryl amines in the presence of t-BuOCl gives N-aryl sulfoximines as described in method E of scheme I.

Scheme III

The compound of general formula (IC) wherein all the symbols are as defined earlier may be prepared by a process outlined in scheme III which comprises:

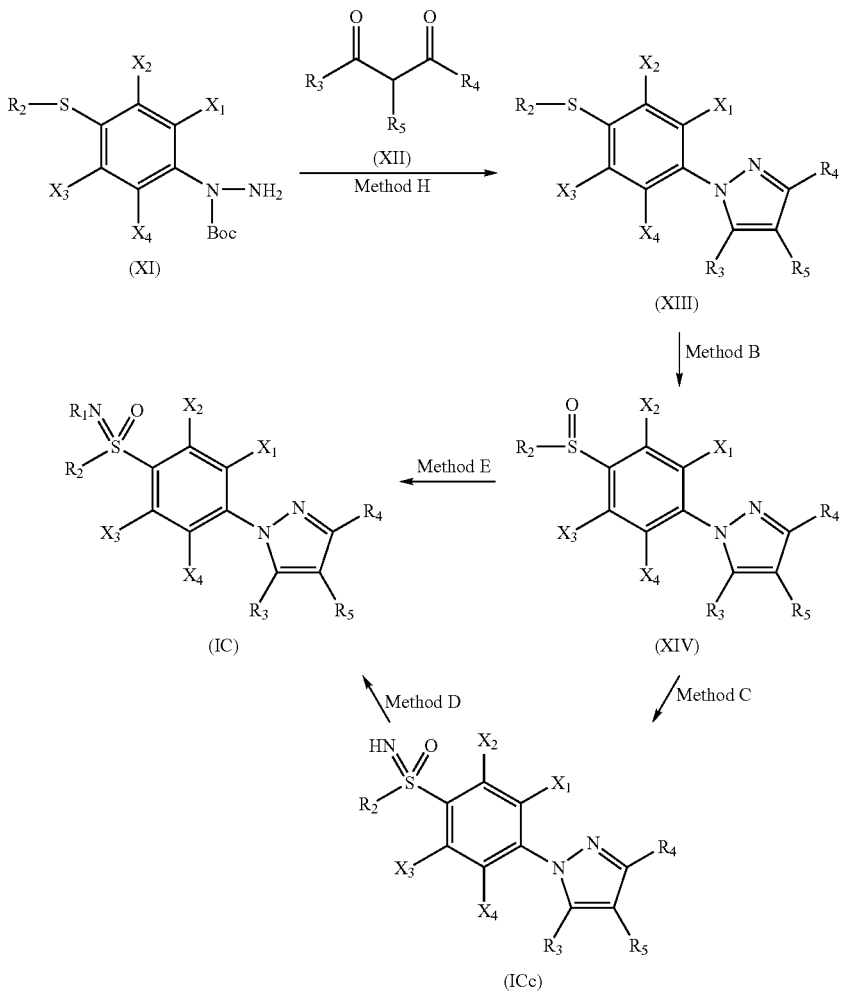

Method C:

The sulfoxide compounds of formula X may be converted to sulfoximine compounds of formula (IBb) by reacting with suitable iminating agents as described earlier in Method C of scheme I.

Method D:

The sulfoximines of formula (IBb) may be converted to compounds of formula (IB) by reaction with appropriate alkylating/acylating agents in the presence of a base as described earlier in method D of scheme I.

Method E:

The compounds X may be directly converted to compounds of formula (IB) by reacting with suitable reagents as described earlier in Method E of scheme I, such as Tosyl azide, Chloramine T, in solvents such as ethanol, methanol i. Reacting hydrazine of general formula XI with 1,3-diketone of general formula XII to get compound of general formula XIII;

ii. Oxidizing compound of formula XIII with appropriate oxidizing agents to get a compound of general formula XIV;

iii. Reacting sulfoxide of formula XIV with appropriate agents to afford compound to of general formula (ICc);

iv. Optionally compound of formula XIV may be converted to compound of formula (IC) by suitable agents to get appropriate $R^1$ group. Alternatively, compound of formula (ICc) may be converted to compound of formula (IC) using appropriate agents.

v. Optionally, if desired, compounds of formula (ICc) or (IC) are converted to pharmaceutically acceptable salts;

The reactions described in the processes outlined in the scheme III above may be performed by using the methods described herein:

Scheme IV

The compound of general formula (ID) wherein all the symbols are as defined earlier may be prepared by a process outlined in scheme IV which comprises:

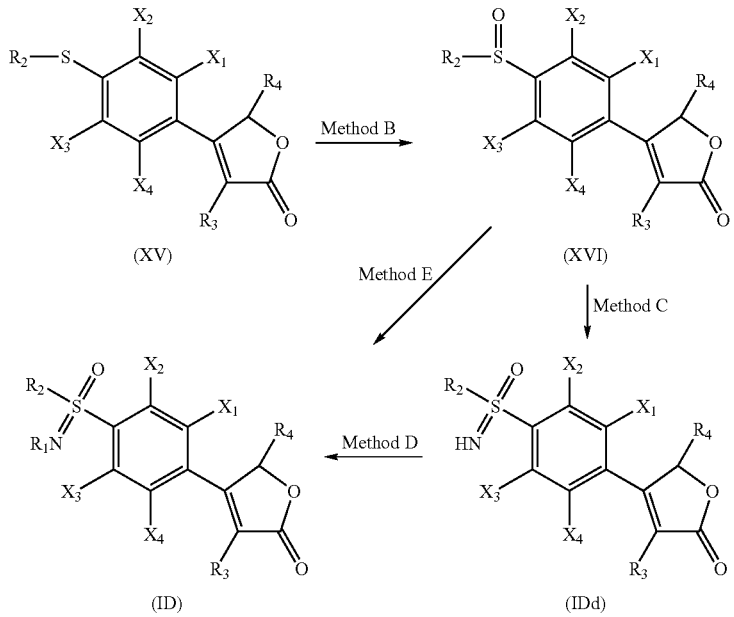

Method H:

The hydrazene of formula XI or its acid addition salts may be converted to compound of formula III by reacting with appropriately substituted 1,3-diketones of formula XII. Reagents like sodium acetate may be used but not critical. Solvents such as alcohols like, ethanol, methanol, isopropanol and the like, THF, dioxane, toluene, xylene, cyclohexane, heptane, hexane, and the like or mixture thereof may be used. Temperature in the range 20° C. to reflux temperature of the solvent may be used, preferably in the range 60° C. to reflux temperature of the solvent(s) may be used. Inert atmosphere may be maintained using $N_2$, He, or argon gas.

Method B:

The pyrazole compound of formula XII may be converted to sulfoxide of formula XIV by reacting with an oxidizing agent as described earlier in method B of scheme I.

Method C:

The sulfoxide compounds of formula XIV may be converted to sulfoximine compounds of formula (ICc) by reacting with suitable iminating agents as described earlier in method C of scheme I.

Method D:

The sulfoximines of (ICc), may be converted to compounds of formula (IC), by reaction with appropriate alkylating/acylating agents in the presence of a base as described earlier in method D of scheme I.

Method E:

The compounds XIV may be directly converted to compounds of formula (IC), by reacting with suitable reagents; such as Tosyl azide, Chloramine T, in solvents such as ethanol, methanol and the like, followed by basification to yield $R_1$=Tosyl groups. Alternatively, reaction with aryl amines in the presence of t-BuOCl gives N-aryl sulfoximines as described in method E of scheme I.

The compound of XV in scheme IV above, may be converted to compound of to general formula (ID) defined earlier, by a method which comprises:

i. Oxidizing compound of XV with appropriate oxidizing agents to get a compound of general formula XVI;

ii. Reacting sulfoxide of formula XVI with appropriate agents to afford compound of general formula (IDd).

iii. Optionally compound of formula (IDd) obtained in ii) above may be converted to compound of formula (ID) by suitable agents to get appropriate $R^1$ group.

iv. Optionally, compound of formula XVI may be directly converted to compound of formula (ID) using appropriate reagents.

v. Optionally, if desired, compound of formula (IDd) or (ID) may be converted to pharmaceutically acceptable salts;

The compound of general formula (ID) may be prepared by a process outlined in scheme IV which comprises:

Method B:

The lactone compound of formula XV may be converted to sulfoxide of formula XVI by reacting with an oxidizing agent as described earlier in method B of scheme I.

Method C:

The sulfoxide compounds of formula XVI may be converted to sulfoximine compounds of formula (IDd) by reacting with suitable iminating agents as described earlier in method C of scheme I.

Method D:

The sulfoximines of (IDd) may be converted to compounds of formula (ID), by reaction with appropriate alkylating/acylating agents in the presence of a base as described earlier in method D of scheme I.

Method E:

The compounds XVI may be directly converted to compounds of formula (ID) by reacting with suitable reagents; such as Tosyl azide, Chloramine T, in solvents such as ethanol, methanol and the like, followed by basification to yield $R_1$=Tosyl groups. Alternatively, reaction with aryl amines in the presence of t-BuOCl gives N-aryl sulfoximines as described in method E of scheme I.

v. Optionally, compound of formula XX may be directly converted to compound of formula (IE) using appropriate reagents.

vi. Optionally, if desired, compound of formula (Ee) or (E) may be converted to pharmaceutically acceptable salts;

The compound of general formula (IE) may be prepared by a process outlined in scheme V which comprises:

Method I:

The keto compound of the formula XVII, may be converted to compound of formula XIX by reacting with Scheme V The compound of general formula (IE) wherein all the symbols are as defined earlier may be prepared by a process outlined in scheme V which comprises:

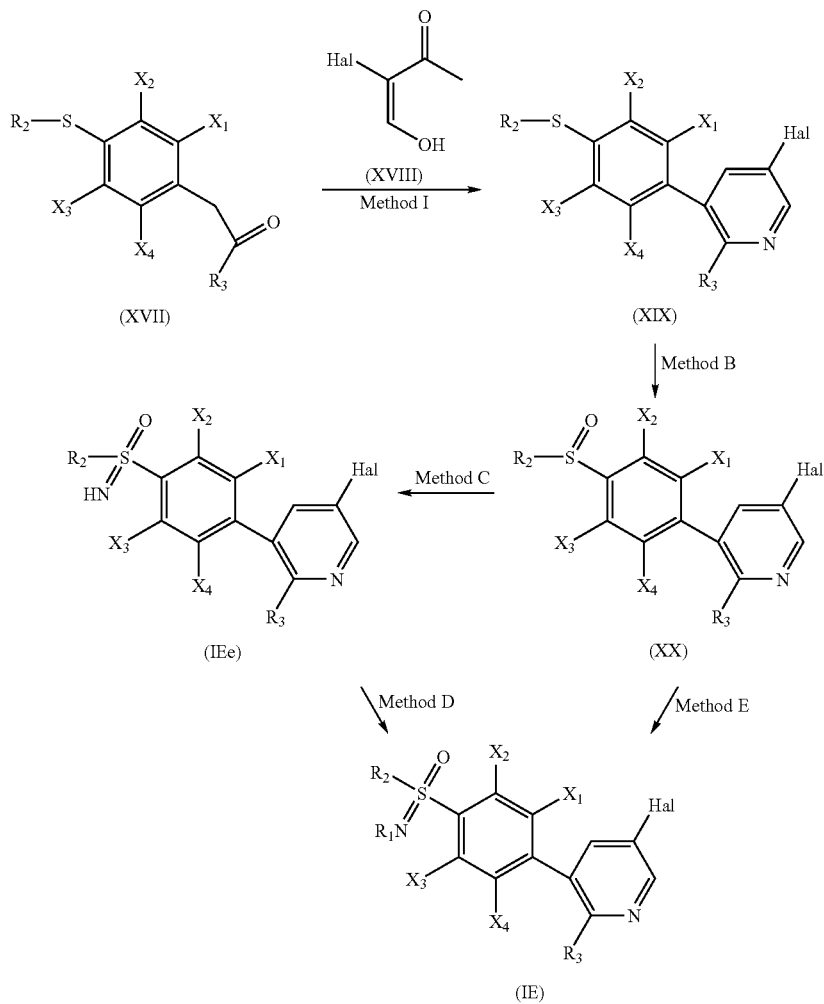

i. Reacting compound of formula XVII, with a compound of formula XVIII to get the compound of formula XIX;

ii. Oxidizing compound of XIX with appropriate oxidizing agents to get a compound of general formula XX;

iii. Reacting sulfoxide of formula XX with appropriate agents to afford compound of (general formula (IEe);

iv. Optionally compound of formula (IEe) obtained in iii) above may be converted to compound of formula (IE) by suitable agents to get appropriate $R^1$ group.

compound of formula XVIII Reagents like ammonium acetate may be used. Reaction may be carried out using solvents like propionic acid or without using solvent. Reaction temperatures may range between ambient and 150° C. or reflux temperature of the solvent(s) used.

Method B:

The pyridine compound of formula XIX may be converted to sulfoxide of formula XX by reacting with an oxidizing agent as described earlier in method B of scheme I.

Method C:

The sulfoxide compounds of formula XX may be converted to sulfoximine compounds of formula (IEe) by reacting with suitable iminating agents as described earlier in method C of scheme I.

Method D:

The sulfoximines of (IEe), may be converted to compounds of formula (IE), by reaction with appropriate alkylating/acylating agents in the presence of a base as described earlier in method D of scheme I.

Method E:

The compounds XX may be directly converted to compounds of formula (IE) by reacting with suitable reagents; such as Tosyl azide, Chloramine T, in solvents such as ethanol, methanol and the like, followed by basification to yield $R_1$=Tosyl groups. Alternatively, reaction with aryl amines in the presence of t-BuOCl gives N-aryl sulfoximines as described in method E of scheme I.

ii. Oxidizing compound of formula XXIII with appropriate oxidizing agents to get a compound of general formula XXIV;

iii. Reacting sulfoxide of formula XXIV with appropriate agents to afford compound of general formula (IFf);

iv. Optionally compound of formula XXIV may be converted to compound of formula (IF) by suitable agents to get appropriate $R^1$ group. Alternatively, compound of formula (IFf) may be converted to compound of formula (IF) using appropriate agents.

v. Optionally, if desired, compounds of formula (IFf) or (IF) are converted to pharmaceutically acceptable salts;

The reactions described in the processes outlined in the scheme VI above may be performed by using the methods described herein:

Method H:

The hydrazene of formula XXII or its acid addition salts may be converted to compound of formula XXIII by react- Scheme VI The compound of general formula (IF) wherein all symbols are as defined earlier may be prepared by a process outlined in scheme VI which comprises:

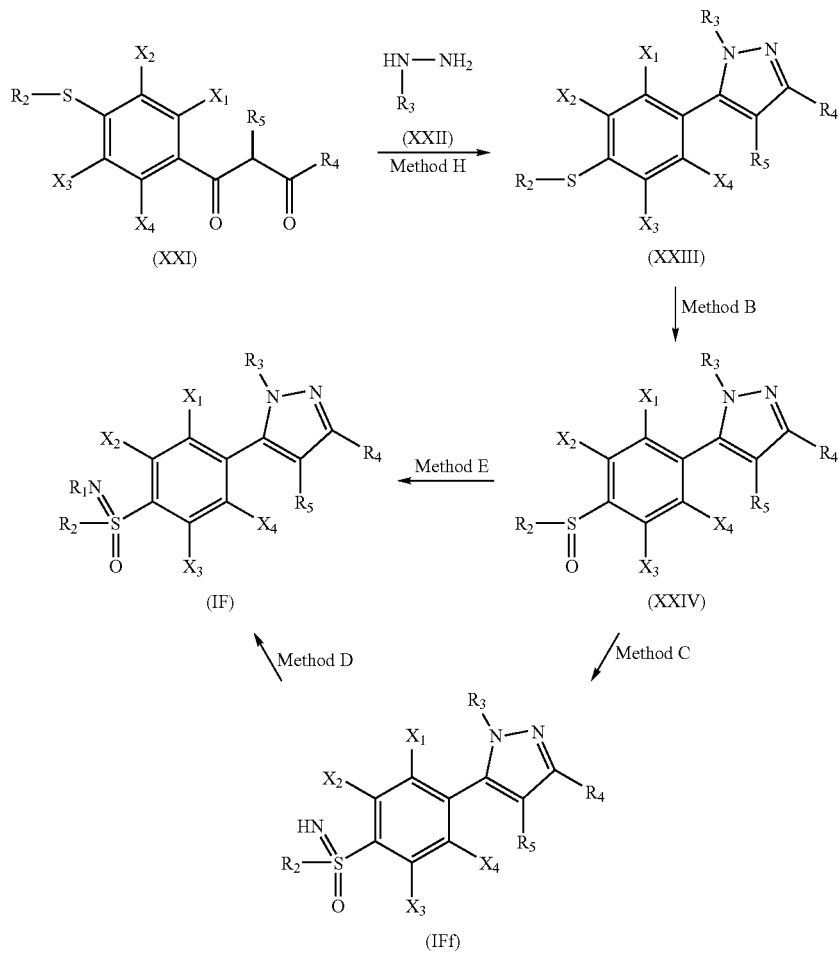

i. Reacting hydrazine of general formula XXII with 1,3-diketone of general formula XXI to get compound of general formula XXIII;

ing with appropriately substituted 1,3-diketones of formula XXI. Reagents like sodium acetate may be used but not critical. Solvents such as alcohols like, ethanol, methanol, isopropanol and the like, THF, dioxane, toluene, xylene, cyclohexane, heptane, hexane, and the like or mixture thereof may be used. Temperature in the range 20° C. to reflux temperature of the solvent may be used, preferably in the range 60° C. to reflux temperature of the solvent(s) may be used. Inert atmosphere may be maintained using $N_2$, He, or argon gas.

Method B:

The pyrazole compound of formula XXIII may be converted to sulfoxide of formula XXIV by reacting with an oxidizing agent as described earlier in method B of scheme I.

Method C:

The sulfoxide compounds of formula XXIV may be converted to sulfoximine compounds of formula (IFf) by reacting with suitable iminating agents as described earlier in method C of scheme I.

Method D:

The sulfoximines of (IFf), may be converted to compounds of formula (IF), by reaction with appropriate alkylating/acylating agents in the presence of a base as described earlier in method D of scheme I.

Method E:

The compounds XXIV may be directly converted to compounds of formula (IF) by reacting with suitable reagents; such as Tosyl azide, Chloramine T, in solvents such as ethanol, methanol and the like, followed by basification to yield $R_1$=Tosyl groups. Alternatively, reaction with aryl amines in the presence of t-BuOCl gives N-aryl sulfoximines as described in method E of scheme I.

Pharmaceutically acceptable salts forming part of this invention are intended to define but not limited to salts of the carboxylic acid moiety when present in the molecule such as alkali metal salts like Li, Na, and K salts; alkaline earth metal salts like Ca and Mg salts; salts of organic bases such as lysine, arginine, guanidine and its derivatives, which may be optionally substituted, diethanolamine, choline, tromethanine and the like; ammonium or substituted ammonium salts and aluminium salts. Salts may be acid addition salts which defines but not limited to sulfates, bisulfates, nitrates, phosphates, perchlorates, borates, hydrohalides, acetates, tartrates, maleates, fumarates, maleates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

It will be appreciated that in any of the above mentioned reactions any reactive group in the substrate molecule may be protected, according to conventional chemical practice. Suitable protecting groups in any of the above mentioned reactions are those used conventionally in the art. The methods of formation and removal in such protecting groups are those conventional methods appropriate to the molecule being protected. T. W. Greene and P. G. M. Wuts "Protective groups in Organic Synthesis", John Wiley & Sons, Inc, 1999, $3^{rd}$ Ed., 201-245 along with references therein.

Acid addition salts, wherever applicable may be prepared by treatment with acids such as tartaric acid, mandelic acid, fumaric acid, malic acid, lactic acid, maleic acid, salicylic acid, citric acid, ascorbic acid, benzene sulfonic acid, p-toluene sulfonic acid, hydroxynaphthoic acid, methane sulfonic acid, acetic acid, benzoic acid, succinic acid, palmitic acid, hydrochloric acid, hydrobromic acid, sulfuric acid, nitric acid and the like in solvents such as water, alcohols, ethers, ethyl acetate, dioxane, THF, acetonitrile, DMF or a lower alkyl ketone such as acetone, or mixtures thereof.

Another aspect of the present invention comprises a pharmaceutical composition, containing at least one of the compounds of the general formula (I), their derivatives, their analogs, their tautomeric forms, their pharmaceutically acceptable salts, their pharmaceutically acceptable solvates thereof as an active ingredient, together with pharmaceutically employed carriers diluents and the like.

Pharmaceutical compositions containing a compound of the present invention may be prepared by conventional techniques, e.g. as described in Remington: the Science and Practice of Pharmacy, $19^{th}$ Ed., 1995. The compositions may be in the conventional forms, such as capsules, tablets, powders, solutions, suspensions, syrups, aerosols or topical applications. They may contain suitable solid or liquid carriers or in suitable sterile media to form injectable solutions or suspensions. The compositions may contain 0.5 to 20%, preferably 0.5 to 10% by weight of the active compound, the remaining being pharmaceutically acceptable carriers, excipients, diluents, solvents and the like. Due to their mixed COX-1/COX-2 activity, the compounds of formula (I) represent good anti-inflammatory compounds having less harmful side effects than the NSAIDs as well as selective COX-2 inhibitors.

The present invention provides a compound of formula (I) for use in a method of treatment of the human or animal body by therapy, in particular for the treatment of pain fever or inflammation, to inhibit prostanoid-induced smooth muscle contraction or for the prevention of colorectal cancer.

Another objective of the present invention is to provide for the use of compound of formula (I) in the manufacture of a medicament for the treatment of pain, fever or inflammation, to inhibit prostanoid-induced smooth muscle contraction or for the prevention of colorectal cancer.

The compounds of the present invention are useful in the treatment of inflammation and inflammation related disorders by administering the subject a therapeutic amount of the compound of formula-I or its active salt. Inflammation is associated with a variety of disease conditions. A list of such disease conditions which can be treated by cyclooxygenase inhibitors and COX-2 inhibitors in particular, are disclosed in U.S. Pat. Nos. 5,604,253 and 5,908,852 and WO 9638442, 9603392 and WO 9714691. Such conditions includes pail, fever and inflammation of a variety of conditions including rheumatic fever, symptoms associated with influenza or other viral infections, common cold, low back and neck pain, dysmenorrhea, headache, toothache, sprains and strains, menstrual cramps, premature labor, Such compounds may also be used in the treatment of arthritis, including but not limited to rheumatoid arthritis, spondyloarthropathies, gouty arthritis, osteoarthritis, systemic lupus erythematosus and juvenile arthritis. They may also be used in the treatment of skin inflammation disorders such as psoriasis, eczema, burning and dermatitis.

The compounds of formula (I) can also be used as alternative to conventional NSAIDs, particularly where such non-steroidal anti-inflammatory drugs may be contraindicated such as the treatment of patients with gastrointestinal disorders including peptide ulcers, gastritis, regional enteritis, ulcerative colitis, diverticulitis, Crohn's disease, inflammatory bowel syndrome and irritable bowl syndrome, ulcerative colitis, Crohn's disease, gastrointestinal bleeding and coagulation disorders, kidney disease (e.g. impaired renal function), those prior to surgery or taking anticoagulants, and those susceptible to NSAIDs.

In addition, compounds of the present invention may inhibit cellular neoplastic transformations and metastatic tumour growth and hence useful in the treatment of cancer. In particular, the present invention provides for a method for treating neoplasia that produces prostaglandin by treating the subject to a therapeutic amount of the compound (I).

Thus the compounds of the present invention would be useful for the prevention and treatment of cancer, such as colorectal cancer and cancer of the lip, mouth, esophagus, breast, lung, prostate, bladder, pancreas, cervix and skin, small bowel cancer, stomach cancer ovary cancer, cervical cancer and the like. Use of COX-2 inhibitors in aforesaid diseases are discussed in U.S. Pat. No. 5,972,986 and WO 0076983 & 9714691. Such compounds will also be useful in the treatment of inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling after injury, myocardial ischemia and the like. The compounds would also be useful in the treatment of ophthalmic diseases such as retinitis, retinopathies, uveitis, ocular photophobia, and of acute injury to the eye tissue. They are also useful in the treatment of pulmonary inflammation, such as that associated with viral infections and cystic fibrosis.

The compounds of the present invention would also be useful for the treatment of certain central nervous system disorders, such as cortical dementias including Alzheimer's disease (*Bratisl Lek Listy* 2001; 102 (3): 123-132) and central nervous system damage resulting from stroke, ischemia and trauma. These compounds will also be use in alleviating neuropathic pain. The compounds of the invention are useful as anti-inflammatory agents, such as for the treatment of arthritis, with the additional benefit of having significantly less harmful side effects. These compounds would be useful in the treatment of allergic rhinitis, respiratory distress syndrome, endotoxin shock syndrome and atherosclerosis.

The compounds of the present invention may also be useful in the treatment of angiogenesis-mediated disorders. Angiogenesis mediated disorders may be treated with cyclooxygenase inhibitors are described in U.S. Pat. No. 6,025,353 and WO 0076983. According to these patents such disorders include, for example, metastasis, corneal graft rejection, ocular neovascularization, diabetic retinopathty, retrolental fibroplasia, neovascular glaucoma, gastric ulcer, infantilehemaginomas, angiofibroma of the nasopharynx, avascular necrosis of the bone and endometrosis.

Besides being useful for human treatment, these compounds are also useful for veterinary treatment of companion animals, exotic animals and farm animals including mammals, rodents, and the like. More preferred animals include horses, dogs and cats.

The present compounds may also be used as co-therapies, partially or completely, in place of other conventional anti-inflammants like steroids, NSAIDs, 5-lipoxygenase inhibitors, $LTB_4$ receptor antagonists and $LTA_4$ hydrolase inhibitors. They can also be used in combination therapies with opoids and other analgesics, including narcotic analgesics, Mu receptor antagonists, Kappa receptor antagonists, non-narcotic analgesics, monoamine uptake inhibitors, adenosine regulating agents, cannabinoid derivatives, substance P antagonists, neurokinin-1 receptor antagonists and sodium channel blockers among others.

The present invention also relates to a pharmaceutical composition for the treatment of a disorder or condition that can be treated by inhibition COX in a mammal, preferably a human, cat, livestock or dog, comprising a COX inhibiting effective amount of a compound of formula (I) or a pharmaceutically acceptable salt thereof and a pharmaceutically acceptable carrier.

The present invention also relates to a method for treating a disorder or condition that can be treated or prevented by inhibiting COX in a mammal, preferably a human, cat, dog livestock, comprising administering to a mammal requiring such treatment a COX inhibiting effective amount of a compound of formula (I) or a pharmaceutically acceptable salt thereof.

This invention also relates to a method of or a pharmaceutical composition for the treatment of inflammation and similar diseases which comprises administering a compound of formula (I) of this invention or its salt to a mammal including a human, cat, livestock or dog. The said inhibitory compound is used in combination with one or more other therapeutically active agents such as:

A) In a condition where a joint has become inflamed along with a bacterial, fungal, protozoal, and/or oral infection, said inhibitory compound is administered in combination with one or more antibiotic, antifungal, antiprotozoal, and/or antiviral therapeutic agents.
   i) During multi-fold treatment of pain and inflammation is required, the compound should be administered in combination with inhibitors of other mediators of inflammation, consisting, of members of the following groups: NSAIDS, $H_1$-receptor antagonists, kinin-$B_1$- and $B_2$-receptor antagonists; prostaglandin inhibitors selected from the group consisting of PGD-, PGF-, $PGI_2$-, and PGE-receptor antagonists; thromboxane $A_2$ ($TXA_2$-) inhibitors; 5-, 12- and 15-lipoxygenase inhibitors; leukotriene $LTC_4$-, $LTD_4/LTE_4$-, and $LTB_4$-inhbitors; PAF-receptor antagonists; anti-inflammatory glucocorticoids; anti-gout agents including colchicine; xanthine oxidase inhibitors including allopurinol; and uricosuric agents selected from probenecid, sulfinpyrazone, and benzbromarone.
B) When treating older mammals with geriatric disorders, the said compound is administered in combination with members selected from any of the following groups: cognitive therapeutics, anti-hypertensives and other cardiovascular drugs selected from among diuretics, vasodilators, β-adrenergic receptor antagonists, ACE inhibitors alone or in combination with neutral endopeptidase inhibitors intending to offset the consequences of atherosclerosis, hypertension, myocardial ischemia, angina, congestive heart failure, and myocardial infarction For the treatment of any of the above-mentioned diseases the compounds of formula (I) may be administered, for example, orally, topically, parenterally, by inhalation spray or rectally in dosage unit formulations containing conventional non-toxic pharmaceutically acceptable carriers, adjuvants and vehicles.

The compounds of the present invention is useful in the treatment of inflammatory diseases caused by cytokines, specially, TNF-α, by either inhibiting the production or by inhibiting the TNF-α converting enzyme (TACE) or by inhibiting TNF-α itself.

In general, the dosage for humans will range preferentially from 0.01 mg to 100 mg per kg of body weight per day, although variations will occur, depending upon the weight, sex and condition of the subject being treated, the state of the disease being treated and the particular route of administration. However, the preferred dosage level should be in the range of from 0.1 mg to 10 ma per kg of body weight per day in single or divided dosage.

For non-human mammals e.g. dogs, cats, horses or other livestock the dosage should be from about 0.01 mg/g to about 20.0 mg/kg/day, and more preferably from about 0.5 mg/kg to about 8.0 mg/kg/day.

The compounds of the present invention may be administered alone or in combination with pharmaceutically acceptable carriers or diluents by any of the routes as previously indicated, in single or multiple doses. More specifically, the novel compounds described in the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, eels, pastes, lotions, ointments, aqueous suspensions, injectable solutions, elixirs, syrups, and the like. The carriers may include solid diluents or fillers, sterile aqueous media and various nontoxic organic solvents etc. Moreover, for oral consumption, the pharmaceutical compositions can be suitably sweetened and/or flavored. In general, the therapeutically-effective compounds as described in the invention are present in the compositions at concentration levels ranging from 5% to 60% by weight, preferably 10% to 50% by weight.

For oral administration, the tablets may be combined with various excipients such as microcrystalline cellulose, sodium citrate, calcium carbonate, dipotassium phosphate and glycine along with various disintegrants such as starch more preferably corn, potato or tapioca starch, alginic acid, sodium carbonate and certain complex sillicates; together with binders like polyvinylpyrrolidone, sucrose, gelatin and acacia, humectants such as for example, glycerol; solution retarding agents, such as, for example paraffin; absorption accelerators such as, for example, quartenary ammonium compounds; wetting agents like cetyl alcohol and glycerol monostearate; absorbents like kaolin and bentonite clay. Additionally, magnesium stearate, sodium lauryl sulfate, talc, calcium stearate, solid polyethylene glycols and mixtures thereof are often added as lubricating agents for tabletting purposes. In the case of capsules, tablets and pills, the dosage form may also comprise buffering agents.

Similar type of solid compositions may also be employed as fillers and excipients in soft and hard gelatine capsules; preferred materials include lactose, milk sugar or high molecular weight polyethylene glycols.

The active compounds can also be in micro-encapsulated form using one or more of the excipients noted above. The solid dosage forms of tablets, dragees, capsules, pills, and the granules can be prepared with coatings and shells such as enteric coatings, release controlling coatings and other coatings which are well known in the field of pharmaceutical formulation art. In such solid dosage forms the active compound may be admixed with at least one inert diluent such as sucrose, lactose and starch. They may also contain, additional substances for e.g. tableting lubricants and other substances like magnesium stearate and microcrystalline cellulose. In the case of capsules, tablets, and pills, the formulation may also contain buffering agents. They may also be so formulated that they release the active ingredient(s) only or preferentially in a certain part of the intestinal tract, optionally in a delayed manner. The same may be achieved using embedded agents like, for example, polymeric substances and waxes.

Liquid dosage forms for oral administration include pharmaceutically acceptable emulsions, microemulsions, solutions, suspensions, syrups, and elixirs. For such oral consumption it is desirable to combine the active ingredient with various sweetening or flavoring agents, coloring matter or dyes, if so desired. The diluents may be selected from water, ethanol, propylene glycol, isopropyl alcohol, ethyl carbonate, ethyl acetate, benzyl alcohol, benzyl benzoate, 1,3 butylene glycol, dimethyl formamide, oils for e.g. cottonseed, groundnut, corn, germ, olive, castor, sesame oils and the like, glycerol, tetrahydrofurfuryl alcohol, polyethylene glycols and esters of fatty acids like sorbitan and various combination thereof. For mammals other than humans, the composition of the active substance are suitably modified.

For parenteral administration, the solutions of the compound is prepared in either sesame or peanut oil or in aqueous propylene glycol. The aqueous solutions should be suitably buffered if necessary, and the diluent should be first rendered isotonic. The aqueous solutions are suitable for intravenous injection purposes while the oily solutions are suitable for intra-articular, intra-muscular and subcutaneous injection purposes. The aforesaid compositions can be readily prepared under sterile conditions following well known standard pharmaceutical techniques by persons skilled in the art.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration the composition may take the form of tablets or lozenges formulated in conventional manner.

For transdermal and topical administration, the dosage forms will include ointments, pastes, creams, lotions, gels, powders, solutions, sprays and inhalants. Transdermal patches may be prepared following standard drug delivery techniques and applied to the skin of a mammal, preferably a human or a dog, to be treated. Ophthalmic solutions, ear drops, eye ointments, powders can also be used as a medium of providing therapeutic dosages to the patients as will be necessary.

The ointments, pastes, creams and gels may, in addition to the active ingredient, contain excipients like animal and vegetable fats, oils, waxes, paraffins, starch tragacanth, cellulose derivatives, polyethylene glycols, silicones, bentonites, silicic acid, talc, zinc oxide or their mixtures.

Powders and sprays may contain, in addition to the active substance, excipients like lactose, talc, silicic acid, aluminium hydroxide, calcium silicates and polyamide powder, or their mixtures. Sprays will additionally contain propellants like chlorofluorohydrocarbons.

The compounds of the present invention have been tested for their biological activities by carrageenan foot pad edema test in male as well as female Wistar rats according to standard protocol described in literature (Winter et. al, *Proc. Soc. Exp. Biol. Med.*, 111, 544, (1962); Otterness and Bliven, Laboratory Models for Testing NSAIDS, in Non-Steroidal Anti-inflammatory Drugs, (J. Lombardino, ed. 1985)). The protocol followed was as described below:

Wistar rats obtained from the Experimental Animal Facility of Zydus Research. Centre. Animals were housed in an environmentally controlled rooms with food and water available ad-libitum. All the experimental protocols were approved by the Institutional Animal Ethics Committee. Animals were divided into different groups, each group comprising of five-six animals. After an overnight fast, animals of the control group received vehicle only by oral gavage whereas animals of the other groups received different doses of the test substance(s). Each rat received same volume of the formulation i.e. 2 ml/kg on body weight basis. One hour after administration of the vehicle or test substance, all the animals received sub-planter injection of carrageenan (1% w/v in saline). Paw volume was measured at 0, 1, 3 and 5 hour after carrageenan injection. Anti-inflammatory activity, expressed as % Inhibition in paw swelling was calculated by measuring change in paw volume at different time intervals after carrageenan injection vs corresponding 0 hr values using the following formula.

$$\% \text{ inhibition} = \frac{(PVC - PVT)}{PVC} \times 100$$

Where

PVC=Average change in Paw volume of control animals

PVT=Average change in Paw volume of treated animals.

The compounds of the present invention inhibited 10%-95% rat paw edema at a dose of 30 mg/kg. The compounds of the present invention possess analgesic property and is effective in neuropathy pain. The compounds of the present invention inhibit the COX-1 and COX-2 coenzymes to varying extents as found by human whole blood assay (C. Brideau, S. Kargman, S. Liu; *Inflammation Research*, 45, 68-74 (1996))

The inhibitory activities of representative compounds of the present invention are given in the following table:

| Sl. No. | Compound No. | Dose (mg/kg) | % Inhibition of paw edema | |
|---|---|---|---|---|
| | | | 1 hour | 3 hour |
| 1. | 179 | 30 | 54 | 41 |
| 2. | 171 | 30 | 50 | 25 |
| 3. | 154 | 30 | 46 | 47 |
| 4. | 97 | 30 | 13 | 36 |
| 5. | 153 | 30 | 42 | 43 |
| 6. | 158 | 30 | 44 | 26 |
| 7. | 187 | 30 | 33 | 29 |
| 8. | 112 | 30 | 57 | 40 |
| 9. | Celecoxib | 30 | 33 | 26 |

The invention is explained in detail by the examples given below, which are provided by way of illustration only and therefore should not be construed to limit the scope of the invention.

1H NMR spectral data given in the tables (vide infra) are are recorded using a 300 MHz spectrometer (Bruker AVANCE-300) and reported in δ scale. Until and otherwise mentioned the solvent used for NMR is $CDCl_3$ Using Tetramethyl silane as the internal standard.

Preparation 1

5-(3-Fluoro-4-methoxyphenyl)-1-(4-methylsulfanylphenyl)-3-trifluoromethyl-1H-pyrazole (Compound No. 14)

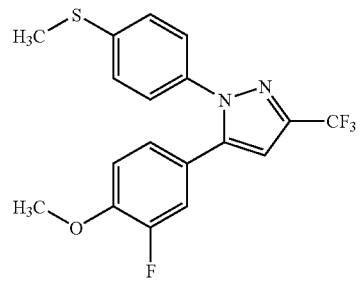

Step 1: Preparation of N-tert-butoxycarbonyl-N-(4-methylsulfanyl)phenyl hydrazine A mixture of 4-methylsulfanyliodobenzene (10 g), tert-butylcarbazate (5.2 g), cesium carbonate (18.2 g), copper iodide (80 rag) and 1,10-phenanthroline (576 mg) in DMF (30 mL) was stirred at 90° C. for 18 h under nitrogen atmosphere. The reaction mixture was chromatographed over silicagel, using 5% ethyl acetate in petroleum ether as eluent to afford 6.2 g of product as a thick liquid.

Step 2: Preparation of 5-(3-fluoro-4-methoxyphenyl)-1-(4-methylsulfanylphenyl)-3-trifluoromethyl-1H-pyrazole A mixture of 1-(3-fluoro-4-methoxyphenyl)-4,4,4-trifluoro butane-1,3-dione (1.0 g) and N-tert-butoxycarbonyl-N-(4-methylthio)phenyl hydrazine (0.9 g) (obtained in step 1 above) in ethanolic HCl (25 mL, 12%) was refluxed for 24 h. Solvent was evaporated under reduced pressure. Water (50 mL) was added to the residue and extracted with diethyl ether (3×50 mL). The organic extract was washed with water (2×50 mL), brine (50 mL), dried over sodium sulphate and evaporated under reduced pressure. The product obtained was chromatographed over silicagel, using 2% ethyl acetate in petroleum ether as eluent to afford 820 mg of product as a thick liquid.

In like manner the following compounds in table 1 were prepared following the procedure described above:

TABLE 1

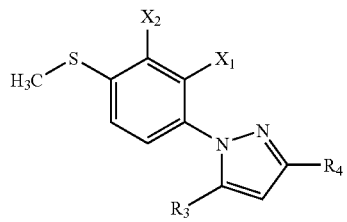

| | $X_2$ | $X_1$ | $R_4$ | $R_3$ | Mol. Wt | % Yield |
|---|---|---|---|---|---|---|
| 1. | H | H | $CF_3$ | 4-F-phenyl | Mol. Wt. = 352 | % Yield = 34 |

$^1$H: 2.49(3H, s), 6.7(1H, s), 7.0(2H, t, J=8.7Hz), 7.2(6H, m).

TABLE 1-continued

[Structure: methylthio-substituted phenyl with X₂, X₁ substituents, attached to pyrazole ring with R₃, R₄ substituents]

| | X₂ | X₁ | R₄ | R₃ | Mol. Wt | % Yield |
|---|---|---|---|---|---|---|
| 2. | H | H | CF₃ | 4-Cl-phenyl | Mol. Wt. = 368.5 | % Yield = 62 |

¹H: 2.5(3H, s), 6.7(1H, s), 7.15(2H, d, J=8.5Hz), 7.2(4H, m), 7.3(2H, d, J=8.5Hz).

| 3. | H | H | CF₃ | 4-CH₃-phenyl | Mol. Wt. = 348 | % Yield = 50 |

¹H: 2.3(3H, s), 2.48(3H, s), 6.7(1H, s), 7.1(4H, m), 7.13(3H, m), 7.3(1H, m).

| 4. | H | H | CF₃ | 4-CH₃O-phenyl | Mol. Wt. = 364 | % Yield = 67 |

¹H: 2.4(3H, s), 3.8(3H, s), 6.67(1H, s), 6.8(2H, d, J=8.8Hz), 7.1(2H, d, J=8.8Hz), 7.2(4H, m).

| 5. | H | H | CF₃ | 4-n-PrO-phenyl | Mol. Wt. = 392 | % Yield = 46 |

¹H: 1.0(3H, t, J=5.7Hz), 1.8(2H, m), 2.4(3H, s), 3.9(2H, t, J=6.5Hz), 6.6(1H, s), 6.8(2H, d, J=6.7Hz), 7.1(2H, d, J=6.6Hz), 7.2(4H, d, J=2.3Hz).

| 6 | H | H | CF₃ | 4-EtO-phenyl | Mol. Wt. = 378 | % Yield = 82 |

¹H: 1.4(3H, t, J=6.9Hz), 2.4(3H, s), 4.0(2H, q, J=6.9Hz), 6.6(1H, s), 6.8(2H, d, J=8.7Hz), 7.1(2H, d, J=8.7Hz), 7.2(4H, m).

| 7. | H | H | CF₃ | 4-iPrO-phenyl | Mol. Wt. = 392 | % Yield = 69 |

¹H: 1.3(6H, d, J=6.0Hz), 2.48(3H, s), 4.5(1H, m), 6.6(1H, s), 6.8(2H, d, J=6.6Hz), 7.1(2H, d, J=8.7Hz), 7.2(4H, m).

| 8. | H | H | CF₃ | 3-Cl-4-F-phenyl | Mol. Wt. = 386.5 | % Yield = 50 |

¹H: 2.5(3H, s), 6.7(1H, s), 7.1(2H, m), 7.2(3H, m), 7.3(2H, dd, J=6.8 & 2.2Hz).

| 9. | H | H | CF₃ | 3,4-diF-phenyl | Mol. Wt. = 370 | % Yield = 88 |

¹H: 2.5(3H, s), 6.7(1H, s), 6.9-7.25(7H, complex).

TABLE 1-continued

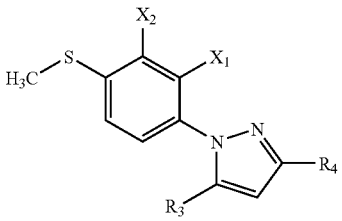

| | $X_2$ | $X_1$ | $R_4$ | $R_3$ | Mol. Wt. | % Yield |
|---|---|---|---|---|---|---|
| 10. | H | H | CF$_3$ | 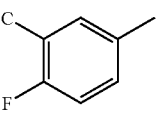 | Mol. Wt. = 366 | % Yield = 53 |

$^1$H: 2.2(3H, s), 2.4(3H, s), 6.7(1H, s), 6.9(2H, d, J=7.4Hz), 7.1(1H, d, J=7.2Hz), 7.2(4H, m).

| 11. | H | H | CF$_3$ | 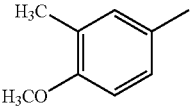 | Mol. Wt. = 378 | % Yield = 58 |

$^1$H: 1.57(3H, s), 2.49(3H, s), 3.9(3H, s), 6.7(1H, s), 6.8(1H, d, J=8.7Hz), 6.9(1H, dd, J=2.1 & 8.7Hz), 7.2(4H, m), 7.3(1H, d, J=2.1Hz).

| 12. | H | H | CF$_3$ | 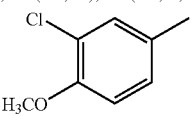 | Mol. Wt. = 398.5 | % Yield = 57 |

$^1$H: 2.49(3H, s), 3.9(3H, s), 6.7(1H, s), 6.8(1H, d, J=8.7Hz), 6.9-7.0(1H, dd, J=2.4 & 8.7Hz), 7.2(4H, m), 7.3(1H, d, J=2.4Hz).

| 13. | H | H | CF$_3$ | 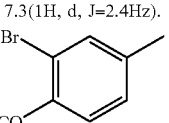 | Mol. Wt = 443 | % Yield = 55 |

$^1$H: 2.49(3H, s), 3.9(3H, s), 6.7(1H, s), 6.8(1H, d, J=7.8Hz), 7.0(1H, dd, J=2.1 & 8.5Hz), 7.2(4H, m), 7.5(1H, d, J=2.6Hz).

| 14. | H | H | CF$_3$ | 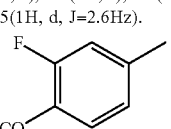 | Mol. Wt. = 382 | % Yield = 56.5 |

$^1$H: 2.49(3H, s), 3.9(3H, s), 6.7(1H, s), 6.8-6.9(3H, m), 7.2(4H, m).

| 15. | H | H | CF$_3$ | 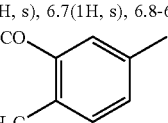 | Mol. Wt. = 378 | % Yield = 50.3 |

$^1$H: 2.2(3H, s), 2.48(3H, s), 3.6(3H, s), 6.6(1H, s), 6.7(2H, m), 7.0(1H, d, J=7.5Hz), 7.2(4H, m).

| 16. | H | F | CF$_3$ | 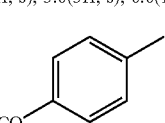 | Mol. Wt. = 382 | % Yield = 74 |

$^1$H: 2.8(3H, s), 3.8(3H, s), 6.7(1H, s), 6.8(2H, dd, J=8.8 & 2.14Hz), 6.9(2H, dd, J = 10.4 & 2.01Hz), 7.15(2H, dd, J=8.85 & 2.1Hz), 7.4(1H, t, J=8.0Hz).

| 17. | F | H | CF$_3$ | 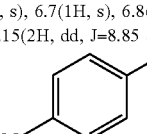 | Mol. Wt. = 382 | % Yield = 66 |

$^1$H: 2.4(3H, s), 3.8(3H, s), 6.67(1H, s), 6.8(2H, d, J=8.8Hz), 7.1(2H, m), 7.17(3H, m).

TABLE 1-continued

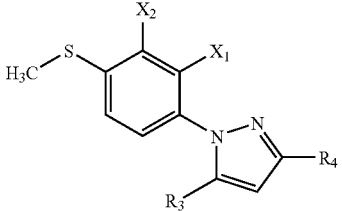

| | $X_2$ | $X_1$ | $R_4$ | $R_3$ | Mol. Wt | % Yield |
|---|---|---|---|---|---|---|
| 18. | H | H | $CF_3$ | 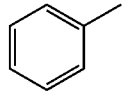 | Mol. Wt. = 334 | % Yield = 59 |

$^1$H: 2.48(3H, s), 6.7(1H, s), 7.23(4H, m), 7.3(5H, m).

| | | | | | | |
|---|---|---|---|---|---|---|
| 19. | H | H | $CH_3$ | 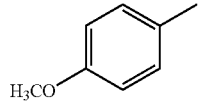 | Mol. Wt. = 310 | % Yield = 42.6 |

$^1$H: 2.23(3H, s), 2.46(3H, s), 3.74(3H, s), 6.3(H, s), 6.9(2H, d, J=8.8Hz), 7.1(4H, m), 7.25(2H, d, J=8.67Hz).

| | | | | | | |
|---|---|---|---|---|---|---|
| 20. | H | H | $CF_3$ | 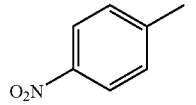 | Mol. Wt. = 379 | % Yield = 77 |

$^1$H: 2.5(3H, s), 6.8(1H, s), 7.2(4H, m), 7.4(2H, d, J=8.9Hz), 8.2(2H, d, J=8.9Hz).

| | | | | | | |
|---|---|---|---|---|---|---|
| 21. | H | H | $CF_3$ | 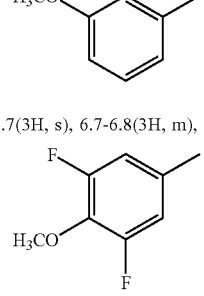 | Mol. Wt. = 364 | % Yield = 71 |

$^1$H: 2.48(3H, s), 3.7(3H, s), 6.7-6.8(3H, m), 6.9(1H, m), 7.3(5H, m).

| | | | | | | |
|---|---|---|---|---|---|---|
| 22. | H | H | $CF_3$ | 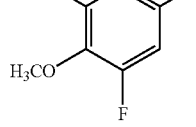 | Mol. Wt. = 400 | % Yield = 73.6 |

$^1$H: 2.5(3H, s), 4.0(3H, s), 6.7(1H, s), 6.79(2H, d, -J=8.6Hz), 7.24(4H, m).

| | | | | | | |
|---|---|---|---|---|---|---|
| 23. | H | H | $CF_3$ | 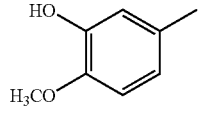 | Mol. Wt. = 380 | % Yield = 98.5 |

$^1$H: 2.5(3H, s), 3.9(3H, s), 5.7(1H, s, —OH), 6.4-6.8(4H, m), 7.1-7.2(4H, m).

| | | | | | | |
|---|---|---|---|---|---|---|
| 24. | H | H | COOH | 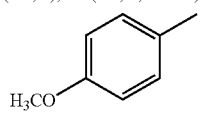 | Mol. Wt. = 340 | % Yield = 90 |

$^1$H: 2.49(3H, s), 3.82(3H, s), 6.8(2H, d, J=8.76Hz), 7.0(1H, s), 7.1(2H, d, J=8.76Hz), 7.26(4H, m)

| | | | | | | |
|---|---|---|---|---|---|---|
| 25. | H | H | $CH_2OH$ | 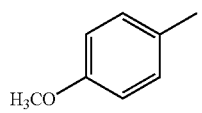 | Mol. Wt. = 326 | % Yield = 85.5 |

$^1$H: 2.0(1H, t, OH), 2.48(3H, s), 3.8(3H, s), 4.8(2H, m), 6.4(1H, s), 6.8(2H, dd, J=8.8 & 3.5Hz), 7.1(2H, d, J=8.7Hz), 7.14-7.3(4H, m).

TABLE 1-continued

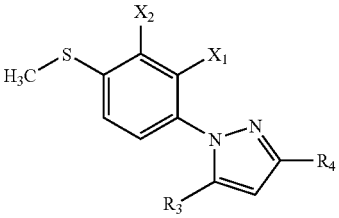

| | $X_2$ | $X_1$ | $R_4$ | $R_3$ | Mol. Wt | % Yield |
|---|---|---|---|---|---|---|
| 26. | H | H | $CF_3$ | 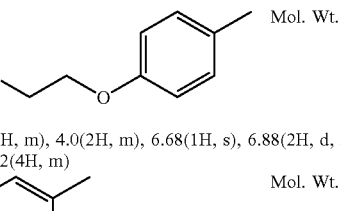 | Mol. Wt. = 394 | % Yield = 53 |

$^1$H: 2.48(3H, s), 3.98(2H, m), 4.0(2H, m), 6.68(1H, s), 6.88(2H, d, J=8.85Hz), 7.1(2H, d, J=8.9Hz), 7.2(4H, m).

| 27. | H | H | $CF_3$ | 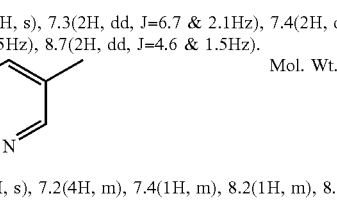 | Mol. Wt. = 335 | % Yield = 25.9 |

$^1$H: 2.55(3H, s), 7.18(1H, s), 7.3(2H, dd, J=6.7 & 2.1Hz), 7.4(2H, d, J=8.6Hz), 7.7(2H, dd, J=4.5 & 1.5Hz), 8.7(2H, dd, J=4.6 & 1.5Hz).

| 28. | H | H | $CF_3$ | 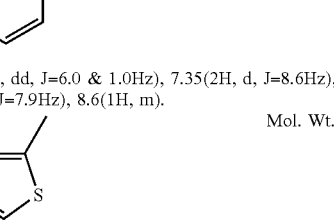 | Mol. Wt. = 335 | % Yield = 61.3 |

$^1$H: 2.54(3H, s), 6.8(1H, s), 7.2(4H, m), 7.4(1H, m), 8.2(1H, m), 8.5(1H, d, J=2.0Hz), 9.0(1H, d, J=1.5Hz).

| 29. | H | H | $CF_3$ | 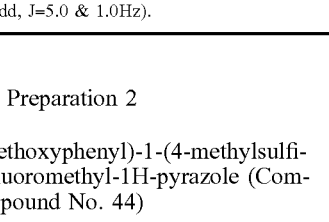 | Mol. Wt. = 335 | % Yield = 27.8 |

$^1$H: 2.54(3H, s), 7.3(1H, dd, J=6.0 & 1.0Hz), 7.35(2H, d, J=8.6Hz), 7.48(3H, m), 7.7(1H, m), 8.0(1H, d, J=7.9Hz), 8.6(1H, m).

| 30. | H | H | $CF_3$ | 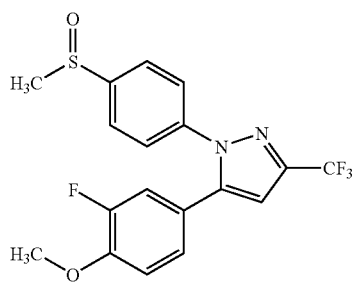 | Mol. Wt. = 340 | % Yield = 45 |

$^1$H: 2.54(3H, s), 6.7(1H, s), 6.8(1H, dd, J=3.57 & 1.05Hz), 6.9(1H, dd, J=5.0 & 3.6Hz), 7.28(4H, m), 7.33(1H, dd, J=5.0 & 1.0Hz).

Preparation 2

5-(3-Fluoro-4-methoxyphenyl)-1-(4-methylsulfinylphenyl)-3-trifluoromethyl-1H-pyrazole (Compound No. 44)

To a solution of 5-(3-fluoro-4-methoxyphenyl)-1-(4-methylsulfanylphenyl)-3-trifluoromethyl-1H-pyrazole (compound No. 14) (790 mg) in chloroform (25 mL), m-chloroperbenzoic acid (55-75%, 464 mg) was added in one portion at −40° C. and stirred at the same temperature for one hour. The reaction mixture was diluted with chloroform (50 mL), washed with saturated solution of aqueous sodium bicarbonate (30 mL), water (2×30 mL), dried over calcium chloride and evaporated under reduced pressure. The product obtained was chromatographed over silicagel using 7:3 ethyl acetate: petroleum ether as eluent to afford 600 mg of product as a thick liquid.

In like manner compounds in the table 2 were prepared following the procedure described above:

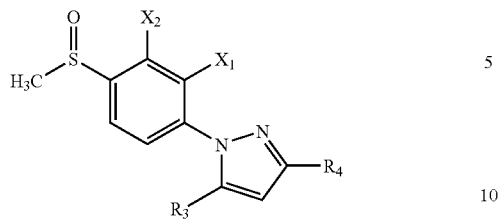

TABLE 2

| # | X$_2$ | X$_1$ | R$_4$ | R$_3$ | Mol. Wt | % Yield |
|---|---|---|---|---|---|---|
| 31. | H | H | CF$_3$ | 4-F-C$_6$H$_4$ | 368 | 59 |

$^1$H: 2.7(3H, s), 6.7(1H, s), 7.0(2H, t, J=8.7Hz), 7.2(2H, m), 7.4(2H, d, J=8.7Hz), 7.6(2H, d, J=8.7Hz).

| 32. | H | H | CF$_3$ | 4-Cl-C$_6$H$_4$ | 384.5 | 53 |

$^1$H: 2.7(3H, s), 6.7(1H, s), 7.1(2H, d, J=8.5Hz), 7.3(2H, d, J=8.5Hz), 7.4(2H, d, J=6.4Hz), 7.6(2H, d, J=8.6Hz).

| 33. | H | H | CF$_3$ | 4-CH$_3$-C$_6$H$_4$ | 364 | 70 |

$^1$H: 2.3(3H, s), 2.7(3H, s), 6.7(1H, s), 7.11(2H, d, J=8.1Hz), 7.16(2H, d, J=8.1Hz), 7.49(2H, d, J=8.5Hz), 7.6(2H, d, J=8.5Hz).

| 34. | H | H | CF$_3$ | 4-CH$_3$O-C$_6$H$_4$ | 380 | 63 |

$^1$H: 2.7(3H, s), 3.8(3H, s), 6.7(1H, s), 6.8(2H, d, J=8.7Hz), 7.1(2H, d, J=8.7Hz), 7.5(2H, d, J=8.5Hz), 7.6(2H, d, J=8.9Hz).

| 35. | H | H | CF$_3$ | 4-n-PrO-C$_6$H$_4$ | 408 | 87 |

$^1$H: 1.0(3H, t, J=7.4Hz), 1.8(2H, m), 2.7(3H, s), 3.9(2H, t, J=6.5Hz), 6.7(1H, s), 6.8(2H, d, J=6.7Hz), 7.1(2H, d, J=6.7Hz), 7.4(2H, d, J=6.6Hz), 7.6(2H, d, J=6.6Hz).

| 36. | H | H | CF$_3$ | 4-EtO-C$_6$H$_4$ | 394 | 84 |

$^1$H: 1.4(3H, t, J=6.9Hz), 2.7(3H, s), 4.0(2H, q, J=6.9Hz), 6.7(1H, s), 6.8(2H, d, J=8.8Hz), 7.1(2H, d, J=8.8Hz), 7.5(2H, d, J=8.6Hz), 7.6(2H, d, J=8.6Hz).

| 37. | H | H | CF$_3$ | 4-i-PrO-C$_6$H$_4$ | 408 | 68 |

$^1$H: 1.3(6H, d, J=6.1Hz), 2.7(3H, s), 4.5(1H, m), 6.7(1H, s), 6.8(2H, d, J=8.9Hz), 7.1(2H, d, J=9.0Hz), 7.5(2H, d, J=8.7Hz), 7.6(2H, d, J=8.9Hz).

TABLE 2-continued

| | $X_2$ | $X_1$ | $R_4$ | $R_3$ | Mol. Wt | % Yield |
|---|---|---|---|---|---|---|
| 38 | H | H | $CF_3$ | 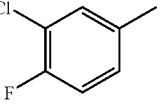 | Mol. Wt. = 402.5 | % Yield = 64 |

$^1$H: 2.7(3H, s), 6.7(1H, s), 7.1(2H, m), 7.3(1H, dd, J=8.9 & 2.1Hz), 7.5(2H, d, J=8.67Hz), 7.7(2H, d, J=8.7Hz).

| | | | | | | |
|---|---|---|---|---|---|---|
| 39. | H | H | $CF_3$ | 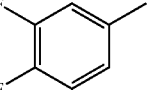 | Mol. Wt. = 386 | % Yield = 65 |

$^1$H: 2.7(3H, s), 6.78(1H, s), 7.1(3H, m), 7.5(2H, d, J=8.6Hz), 7.7(2H, d, J=8.3Hz).

| | | | | | | |
|---|---|---|---|---|---|---|
| 40. | H | H | $CF_3$ | 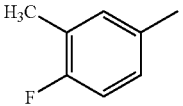 | Mol. Wt. = 382 | % Yield = 65 |

$^1$H: 2.2(3H, s), 2.7(3H, s), 6.7(1H, s), 6.9(2H, m), 7.1(1H, m), 7.4(2H, d, J=8.7Hz), 7.6(2H, d, J=8.6Hz).

| | | | | | | |
|---|---|---|---|---|---|---|
| 41. | H | H | $CF_3$ | 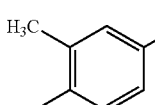 | Mol. Wt. = 394 | % Yield = 78 |

$^1$H: 2.1(3H, s), 2.7(3H, s), 3.8(3H, s), 6.7(1H, s), 6.73(1H, d, J=8.3Hz), 6.9(1H, dd, J=2.1 & 8.1Hz), 7.0(1H, d, J=2.4Hz), 7.5(2H, d, J=8.5Hz), 7.6(2H, d, J=8.3Hz).

| | | | | | | |
|---|---|---|---|---|---|---|
| 42. | H | H | $CF_3$ | 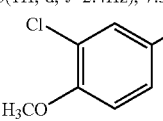 | Mol. Wt. = 414.5 | % Yield = 80.5 |

$^1$H: 2.7(3H, s), 3.9(3H, s), 6.7(1H, s), 6.8(1H, d, J=8.5Hz), 7.0(1H, dd, J=2.1 & 8.4Hz), 7.3(1H, d, J=2.4Hz), 7.5(2H, d, J=8.5Hz), 7.6(2H, d, J=8.5Hz).

| | | | | | | |
|---|---|---|---|---|---|---|
| 43. | H | H | $CF_3$ | 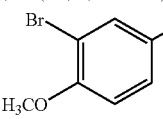 | Mol. Wt. = 459 | % Yield = 55 |

$^1$H: 2.7(3H, s), 3.9(3H, s), 6.7(1H, s), 6.8(1H, d, J=8.5Hz), 7.0(1H, dd, J=2.1 & 8.5Hz), 7.4-7.5(3H, m), 7.6(2H, d, J=8.5Hz).

| | | | | | | |
|---|---|---|---|---|---|---|
| 44. | H | H | $CF_3$ | 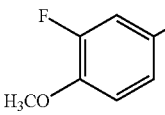 | Mol. Wt. = 398 | % Yield = 73 |

$^1$H: 2.7(3H, s), 3.9(3H, s), 6.7(1H, s), 6.9(3H, m), 7.4(2H, d, J=8.5Hz), 7.6(2H, d, J=8.5Hz).

| | | | | | | |
|---|---|---|---|---|---|---|
| 45. | H | H | $CF_3$ | 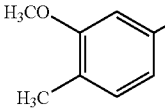 | Mol. Wt. = 394 | % Yield = 71 |

$^1$H: 2.2(3H, s), 2.7(3H, s), 3.6(3H, s), 6.6(1H, d, J=1.2Hz), 6.6-6.7(1H, dd, J=1.4 & 7.6Hz), 6.7(1H, s), 7.0-7.1(1H, d, J=7.6Hz), 7.5(2H, d, J=8.6Hz), 7.6(2H, d, J=8.6Hz).

| | | | | | | |
|---|---|---|---|---|---|---|
| 46. | H | F | $CF_3$ | 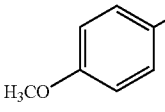 | Mol. Wt. = 398 | % Yield = 51 |

$^1$H: 2.7(3H, s), 3.8(3H, s), 6.7(1H, s), 6.8(2H, d, J=8.8Hz), 7.1(2H, d, J=8.8Hz), 7.4(2H, m), 7.6(1H, m).

TABLE 2-continued

| | $X_2$ | $X_1$ | $R_4$ | $R_3$ | Mol. Wt | % Yield |
|---|---|---|---|---|---|---|
| 47. | F | H | CF$_3$ | 4-H$_3$CO-C$_6$H$_4$- | Mol. Wt. = 398 | % Yield = 77 |

$^1$H: 2.8(3H, s), 3.8(3H, s), 6.7(1H, s), 6.9(2H, d, J=8.8Hz), 7.1(2H, d, J=8.8Hz), 7.2(2H, m), 7.8(1H, t, J=7.8Hz).

| | | | | | | |
|---|---|---|---|---|---|---|
| 48. | H | H | CF$_3$ | C$_6$H$_5$- | Mol. Wt. = 350 | % Yield = 36 |

$^1$H: 2.7(3H, s), 6.7(1H, s), 7.2(2H, d, J=8.5Hz), 7.4(3H, m), 7.5(2H, d, J=8.5Hz), 7.6(2H, d, J=8.5Hz).

| | | | | | | |
|---|---|---|---|---|---|---|
| 49. | H | H | CH$_3$ | 4-H$_3$CO-C$_6$H$_4$- | Mol. Wt. = 326 | % Yield = 80 |

$^1$H: 2.37(3H, s), 2.7(3H, s), 3.8(3H, s), 6.27(1H, s), 6.8(2H, d, J=8.8Hz), 7.1(2H, d, J=8.8Hz), 7.46(2H, d, J=8.6Hz), 7.6(2H, d, J=8.6Hz).

| | | | | | | |
|---|---|---|---|---|---|---|
| 50. | H | H | CF$_3$ | 4-O$_2$N-C$_6$H$_4$- | Mol. Wt. = 395 | % Yield = 82 |

$^1$H: 2.8(3H, s), 6.9(1H, s), 7.2-7.4(4H, m), 7.7(2H, d, J=8.5Hz), 8.25(2H, d, J=8.8Hz).

| | | | | | | |
|---|---|---|---|---|---|---|
| 51. | H | H | CF$_3$ | 3-H$_3$CO-C$_6$H$_4$- | Mol. Wt. = 380 | % Yield = 68 |

$^1$H: 2.7(3H, s), 3.7(3H, s), 6.8(3H, m), 6.9(1H, m), 7.3(1H, m), 7.5(2H, d, J=8.5Hz), 7.7(2H, d, J=8.5Hz).

| | | | | | | |
|---|---|---|---|---|---|---|
| 52. | H | H | CF$_3$ | 3,5-F$_2$-4-H$_3$CO-C$_6$H$_2$- | Mol. Wt. = 416 | % Yield = 49 |

$^1$H: 2.7(3H, s), 4.0(3H, s), 6.79(3H, m), 7.5(2H, d, J=8.64Hz), 7.7(2H, d, J=8.6Hz).

| | | | | | | |
|---|---|---|---|---|---|---|
| 53. | H | H | CF$_3$ | 3-HO-4-H$_3$CO-C$_6$H$_3$- | Mol. Wt. = 396 | % Yield = 83 |

$^1$H: 2.7(3H, s), 3.9(3H, s), 5.7(1H, s), 6.7(2H, m), 6.8(2H, m), 7.5(2H, d, J=8.6Hz), 7.67(2H, d, J=8.6Hz).

| | | | | | | |
|---|---|---|---|---|---|---|
| 54. | H | H | COOH | 4-H$_3$CO-C$_6$H$_4$- | Mol. Wt. = 356 | % Yield = 63 |

$^1$H: 2.7(3H, s), 3.8(3H, s), 6.8(2H, d, J=8.4Hz), 6.9(1H, s), 7.16(2H, d, J=8.34Hz), 7.5(2H, d, J=8.3Hz), 7.65(2H, d, J=8.3Hz0).

| | | | | | | |
|---|---|---|---|---|---|---|
| 55. | H | H | CH$_2$OH | 4-H$_3$CO-C$_6$H$_4$- | Mol. Wt. = 342 | % Yield = 80 |

$^1$H: 2.7(3H, s), 3.8(3H, s), 4.79(2H, s), 6.5(1H, s), 6.87(2H, d, J=8.7Hz), 7.16(2H, d, J=8.7Hz), 7.47(2H, d, J=8.5Hz), 7.6(2H, d, J=8.5Hz).

TABLE 2-continued

| | X₂ | X₁ | R₄ | R₃ | Mol. Wt | % Yield |
|---|---|---|---|---|---|---|
| 56. | H | H | CF₃ | 4-(2-hydroxyethoxy)phenyl | Mol. Wt. = 410 | % Yield = 70 |

¹H: 2.74(3H, s), 3.98(2H, m), 4.1(2H, dd, J=5.4 & 4.0Hz), 6.7(1H, s), 6.9(2H, dd, J=8.8 & 2.0Hz), 7.1(2H, dd, J=8.8 & 2.0Hz), 7.5(2H, dd, J=8.9 & 2.1Hz), 7.6(2H, dd, J=6.6 & 1.9Hz)

| | | | | | | |
|---|---|---|---|---|---|---|
| 57. | H | H | CF₃ | pyridin-4-yl | Mol. Wt. = 351 | % Yield = 25.9 |

¹H: 2.89(3H, s), 7.66(1H, s), 7.84(2H, d, J=8.55Hz), 7.9(4H, m), 8.6(2H, d, J=5.7Hz).

| | | | | | | |
|---|---|---|---|---|---|---|
| 58. | H | H | CF₃ | pyridin-3-yl | Mol. Wt. = 351 | % Yield = 61.3 |

¹H: 2.8(3H, s), 7.1(1H, s), 7.4(1H, m), 7.75(2H, d, J=8.58Hz), 7.8(2H, d, J=8.64Hz), 8.1(1H, m), 8.6(1H, dd, J=4.74 & 1.2Hz), 9.0(1H, d, J=1.53Hz).

| | | | | | | |
|---|---|---|---|---|---|---|
| 59. | H | H | CF₃ | pyridin-2-yl | Mol. Wt. = 351 | % Yield = 27.8 |

¹H: 2.8(3H, s), 7.3(1H, dd, J=9.0 & 1.2Hz), 7.54(1H, s), 7.8(5H, m), 8.0(1H, d, J=8.0Hz), 8.67(1H, d, J=4.5Hz).

| | | | | | | |
|---|---|---|---|---|---|---|
| 60. | H | H | CF₃ | thien-2-yl | Mol. Wt. = 356 | % Yield = 54 |

¹H: 2.76(3H, s), 6.8(1H, s), 6.9(1H, dd, J=3.7 & 1.05Hz), 7.0(1H, dd, J=5.0 & 3.6Hz), 7.4(1H, dd, J=5.1 & 1.1Hz), 7.6(2H, dd, J=8.5 & 1.9Hz), 7.7(2H, dd, J=8.5 & 1.9Hz).

Preparation 3

5-(3-Fluoro-4-methoxyphenyl)-1-(4-methylsulfoximinylphenyl)-3-trifluoromethyl-1H-pyrazole (Compound No. 74)

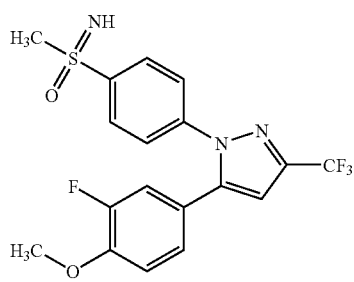

To a solution of 5-(3-fluoro-4-methoxyphenyl)-1-(4-methylsulfinylphenyl)-3-trifluoromethyl-1H-pyrazole (Compound No. 44) (570 mg) in chloroform (25 mL) were added sodium azide (186 mg) followed by concentrated sulfuric acid (0.14 mL) at 0° C. and stirred at 40° C. for 18 h. An equal amount of sodium azide and sulfuric acid that were added earlier was added every two hours for four times and stirred for further four hours thereafter at 40° C. The reaction mixture was cooled to 20° C., diluted with chloroform (50 mL), washed with saturated aqueous solution of sodium bicarbonate (2×50 mL), water (50 mL), dried over calcium chloride and evaporated under reduced pressure to afford the product (500 mg) as a thick liquid.

In like manner compounds in the table 3 were prepared following the procedure described above

TABLE 3

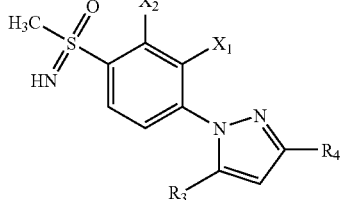

| | X₂ | X₁ | R₄ | R₃ | Mol. Wt | Yield |
|---|---|---|---|---|---|---|
| 61. | H | H | CF₃ | 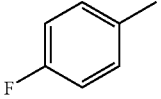 | Mol. Wt. = 383 | % Yield = 36 |

¹H, CD₃OD: 3.8(3H, s), 6.9(1H, s), 7.0(2H, t, J=8.7Hz), 7.2(2H, m), 7.6(2H, d, J=8.9Hz), 8.1(2H, d, J=8.9Hz).

| | | | | | | |
|---|---|---|---|---|---|---|
| 62. | H | H | CF₃ | 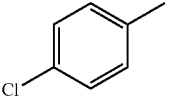 | Mol. Wt. = 399.5 | % Yield = 72 |

¹H, CD₃OD: 3.8(3H, s), 7.0(1H, s), 7.3(2H, d, J=8.7Hz), 7.4(2H, d, J=8.6Hz), 7.7(2H, d, J=8.9Hz), 8.2(2H, d, J=9.0Hz).

| | | | | | | |
|---|---|---|---|---|---|---|
| 63. | H | H | CF₃ | 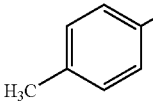 | Mol. Wt. = 379 | % Yield = 71 |

¹H: 2.3(3H, s), 3.1(3H, s), 6.7(1H, s), 7.1(2H, d, J=8.1Hz), 7.18(2H, d, J=8.1Hz), 7.5(2H, d, J=8.5Hz), 7.9(2H, d, J=8.5Hz).

| | | | | | | |
|---|---|---|---|---|---|---|
| 64. | H | H | CF₃ | 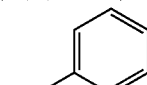 | Mol. Wt. = 395 | % Yield = 51 |

¹H, CD₃OD: 3.8(3H, s), 3.9(3H, s), 6.9(1H, s), 6.9(2H, d, J=8.7Hz), 7.2(2H, d, J=9.0Hz), 7.7(2H, d, J=9.0Hz), 8.2(2H, d, J=9.1Hz).

| | | | | | | |
|---|---|---|---|---|---|---|
| 65. | H | H | CF₃ | 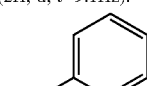 | Mol. Wt. = 423 | % Yield = 33 |

¹H, dMSO-d₆: 1.0(3H, t, J=7.4Hz), 1.8(2H, m), 3.8(3H, s), 3.9(2H, t, J=6.4Hz), 6.9(2H, d, J=8.7Hz), 6.9(1H, s), 7.2(2H, d, J=8.7Hz), 7.7(2H, d, J=8.8Hz), 8.19(2H, d, J=8.8Hz).

| | | | | | | |
|---|---|---|---|---|---|---|
| 66. | H | H | CF₃ | 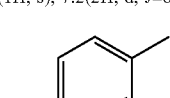 | Mol. Wt. = 409 | % Yield = 22 |

¹H, CD₃OD: 1.2(3H, t, J=6.9Hz), 3.7(3H, s), 3.9(2H, q, J=6.9Hz), 6.8(1H, s), 6.8(2H, d, J=8.8Hz), 7.1(2H, d, J=8.8Hz), 7.6(2H, d, J=8.9Hz), 8.1(2H, d, J=8.9Hz).

| | | | | | | |
|---|---|---|---|---|---|---|
| 67. | H | H | CF₃ | 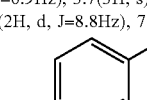 | Mol. Wt. = 381 | % Yield = 66 |

¹H, CD₃OD: 3.8(3H, s), 6.7(2H, d, J=8.6Hz), 6.8(1H, s), 7.1(2H, d, J=8.6Hz), 7.7(2H, d, J=8.9Hz), 8.2(2H, d, J=8.9Hz).

| | | | | | | |
|---|---|---|---|---|---|---|
| 68. | H | H | CF₃ | 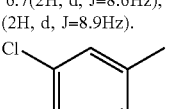 | Mol. Wt. = 417.5 | % Yield = 95 |

¹H, CD₃OD: 3.89(3H, s), 7.0(1H, s), 7.3(2H, d, J=7.7Hz), 7.5(1H, d, J=6.9Hz), 7.8(2H, d, J=8.9Hz), 8.2(2H, m).

TABLE 3-continued

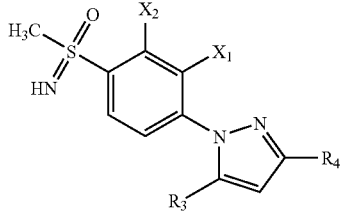

| | X₂ | X₁ | R₄ | R₃ | Mol. Wt | Yield |
|---|---|---|---|---|---|---|
| 69. | H | H | CF₃ | 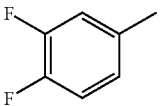 | Mol. Wt. = 401 | % Yield = 96 |

¹H, CD₃OD: 3.9(3H, s), 7.0(1H, s), 7.2(1H, m), 7.3(2H, m), 7.8(2H, d, J=8.8Hz), 8.2(2H, d, J=8.8Hz).

| | | | | | | |
|---|---|---|---|---|---|---|
| 70. | H | H | CF₃ | 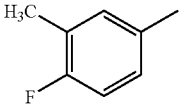 | Mol. Wt. = 397 | % Yield = 47 |

¹H, CD₃OD: 2.2(3H, s), 3.7(3H, s), 6.9(1H, s), 7.1(2H, m), 7.3(1H, d, J=7.2Hz), 7.7(2H, d, J=8.9Hz), 8.2(2H, d, J=8.9Hz).

| | | | | | | |
|---|---|---|---|---|---|---|
| 71. | H | H | CF₃ | 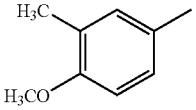 | Mol. Wt. = 409 | % Yield = 41 |

¹H, CD₃OD: 2.1(3H, s), 3.3(3H, s), 3.8(3H, s), 6.9(1H, d, J=8.5Hz), 7.0(1H, dd, J=2.1 & 8.5Hz), 7.1(1H, s), 7.2(1H, d, J=1.52Hz), 7.6(2H, d, J=8.6Hz), 8.0(2H, d, J=8.7Hz).

| | | | | | | |
|---|---|---|---|---|---|---|
| 72. | H | H | CF₃ | 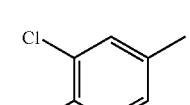 | Mol. Wt. = 429.5 | % Yield = 34.5 |

¹H, CD₃OD: 3.8(3H, s), 3.9(3H, s), 6.9(1H, s), 7.0-7.1(1H, d, J=8.6Hz), 7.2(1H, dd, J=2.1 & 8.2Hz), 7.3(1H, d, J=2.1Hz), 7.7(2H, d, J=8.9Hz), 8.2(2H, d, J=8.9Hz).

| | | | | | | |
|---|---|---|---|---|---|---|
| 73. | H | H | CF₃ | 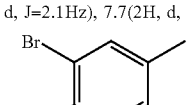 | Mol. Wt. = 474 | % Yield = 56 |

¹H, CD₃OD: 3.9(3H, s), 3.92(3H, s), 6.9(1H, s), 7.0(1H, d, J=8.5Hz), 7.2-7.3(1H, dd, J=2.1 & 8.5Hz), 7.5(1H, d, J=2.1Hz), 7.8(2H, d, J=8.9Hz), 8.2(2H, d, J=8.9Hz).

| | | | | | | |
|---|---|---|---|---|---|---|
| 74. | H | H | CF₃ | 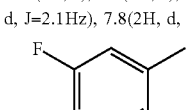 | Mol. Wt. = 413 | % Yield = 74 |

¹H, CD₃OD: 3.89(3H, s), 3.9(3H, s), 6.9(1H, s), 7.1(3H, m), 7.7(2H, d, J=8.8Hz), 8.2(2H, d, J=8.5Hz).

| | | | | | | |
|---|---|---|---|---|---|---|
| 75. | H | H | CF₃ | 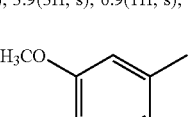 | Mol. Wt. = 409 | % Yield = 40 |

¹H: 2.2(3H, s), 2.7(3H, s), 3.6(3H, s), 6.6(1H, d, J=1.2Hz), 6.6-6.7(1H, dd, J=1.4 & 7.6Hz), 6.7(1H, s), 7.0-7.1(1H, d, J=7.6Hz), 7.5(2H, d, J=8.6Hz), 7.6(2H, d, J=8.6Hz).

TABLE 3-continued

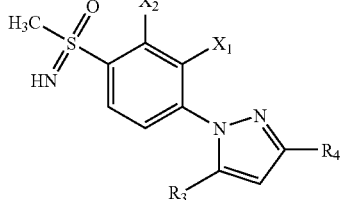

| | X₂ | X₁ | R₄ | R₃ | Mol. Wt | Yield |
|---|---|---|---|---|---|---|
| 76. | H | F | CF₃ | 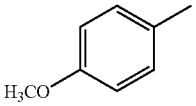 | Mol. Wt. = 413 | % Yield = 94 |

¹H: 3.1(3H, s), 3.8(3H, s), 6.7(1H, s), 6.8(2H, dd, J=2.0 & 8.8Hz), 7.1(2H, dd, J=2.0 & 8.8Hz), 7.7(2H, m), 7.9(1H, m).

| 77. | F | H | CF₃ | 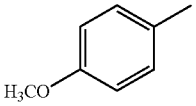 | Mol. Wt. = 413 | % Yield = 25 |

¹H: 3.2(3H, s), 3.8(3H, s), 6.7(1H, s), 6.9(2H, d, J=8.8Hz), 7.1(3H, m), 7.3(1H, dd, J=1.9 & 10.4Hz), 7.9(1H, d, J=8.4Hz).

| 78. | H | H | CF₃ | 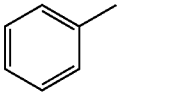 | Mol. Wt. = 365 | % Yield = 32 |

¹H, CD₃OD: 3.8(3H, s), 7.0(1H, s), 7.3-7.4(5H, m), 7.7(2H, d, J=8.7Hz), 8.1(2H, d, J=8.8Hz).

| 79. | H | H | CH₃ | 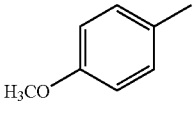 | Mol. Wt. = 341 | % Yield = 93 |

¹H, CD₃OD: 2.35(3H, s), 3.8(3H, s), 3.89(3H, s), 6.4(1H, s), 6.9(2H, d, J=8.8Hz), 7.2(2H, d, J=8.8Hz), 7.7(2H, d, J=8.9Hz), 8.1(2H, d, J=8.9Hz).

| 80. | H | H | CF₃ | 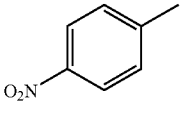 | Mol. Wt. = 410 | % Yield = 92 |

¹H, CD₃OD: 3.9(3H, s), 7.2(1H, s), 7.6(2H, d, J=8.9Hz), 7.8(2H, d, J=8.9Hz), 8.2(4H, m),

| 81. | H | H | CF₃ | 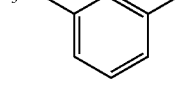 | Mol. Wt. = 395 | % Yield = 84 |

¹H, CD₃OD: 3.7(3H, s), 3.9(3H, s), 6.9(2H, m), 7.0(2H, m), 7.3(1H, t, J=7.9Hz), 7.8(2H, d, J=8.9Hz), 8.2(2H, d, J=8.9Hz).

| 82. | H | H | CF₃ | 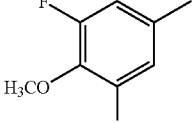 | Mol. Wt. = 431 | % Yield = 90 |

¹H, CD₃OD: 3.9(3H, s), 4.0(3H, s), 7.02(1H, s), 7.06(2H, d, J=2.7Hz), 7.8(2H, d, J=8.9Hz), 8.2(2H, d, J=8.9Hz).

| 83. | H | H | CF₃ | 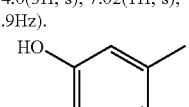 | Mol. Wt. = 411 | % Yield = 46 |

¹H, CD₃OD: 3.86(3H, s), 3.91(3H, s), 6.7(1H, d, J=2.07Hz), 6.8(1H, dd, J=8.25 & 2.07Hz), 6.9(2H, m), 7.8(2H, d, J=8.85Hz), 8.2(2H, d, J=8.85Hz).

TABLE 3-continued

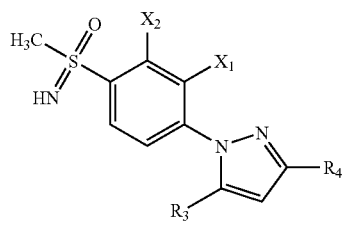

| | X₂ | X₁ | R₄ | R₃ | Mol. Wt | Yield |
|---|---|---|---|---|---|---|
| 84. | H | H | COOH | 4-methoxyphenyl | Mol. Wt. = 371 | % Yield = 56 |

¹H, dMSO-d₆: 3.09(3H, s), 3.75(3H, s), 6.9(2H, d, J=8.7Hz), 7.0(1H, s), 7.2(2H, d, J=8.7Hz), 7.5(2H, d, J=8.5Hz), 7.9(2H, d, J=8.5Hz).

| | | | | | | |
|---|---|---|---|---|---|---|
| 85. | H | H | CH₂OH | 4-methoxyphenyl | Mol. Wt. = 357 | % Yield = 46 |

¹H, CD₃OD: 3.8(3H, s), 3.9(3H, s), 4.67(2H, s), 6.6(1H, s), 6.95(2H, d, J=8.8Hz), 7.23(2H, d, J=8.8Hz), 7.7(2H, d, J=8.99Hz), 8.17(2H, d, J=8.99Hz).

| | | | | | | |
|---|---|---|---|---|---|---|
| 86. | H | H | CH₂OSO₃H | 4-methoxyphenyl | Mol. Wt. = 437 | % Yield = 28 |

¹H, dMSO-d₆: 3.77(3H, s), 3.86(3H, s), 4.87(2H, s), 6.6(1H, s), 6.98(2H, d, J=8.7Hz), 7.2(2H, d, J=8.7Hz), 7.65(2H, d, J=8.8Hz), 8.1(2H, d, J=8.8Hz).

| | | | | | | |
|---|---|---|---|---|---|---|
| 87. | H | H | CF₃ | 4-(2-hydroxyethoxy)phenyl | Mol. Wt. = 425 | % Yield = 25 |

¹H: 1.99(1H, t, OH), 2.73(1H, br, NH), 3.1(3H, s), 4.0(2H, m), 4.1(2H, m), 6.7(1H, s), 6.9(2H, dd, J=8.7 & 2.1Hz), 7.15(2H, dd, J=8.8 & 2.1Hz), 7.5(2H, dd, J=8.7 & 2.2Hz), 8.0(2H, dd, J=8.7 & 1.9Hz).

| | | | | | | |
|---|---|---|---|---|---|---|
| 88 | H | H | CF₃ | 4-pyridyl | Mol. Wt. = 366 | % Yield = 78.3 |

¹H: 3.18(3H, s), 7.27(1H, s), 7.75(2H, dd, J=4.5 & 1.6Hz), 7.8(2H, d, J=8.5Hz), 8.2(2H, d, J=8.7Hz), 8.7(2H, dd, J=4.5 & 1.5Hz).

| | | | | | | |
|---|---|---|---|---|---|---|
| 89. | H | H | CF₃ |  | Mol. Wt. = 366 | % Yield = 86.5 |

¹H: 3.18(3H, s), 7.23(1H, s), 7.4(1H, m), 7.8(2H, d, J=8.61Hz), 8.1(3H, m), 8.6(1H, d, J=4.7Hz), 9.0(1H, s).

| | | | | | | |
|---|---|---|---|---|---|---|
| 90. | H | H | CF₃ |  | Mol. Wt. = 366 | % Yield = 88.8 |

¹H: 3.1(3H, s), 7.3(1H, m), 7.5(1H, s), 7.7-7.8(3H, m), 8.0(1H, d, J=7.9Hz), 8.2(2H, d, J= 8.64Hz), 8.69(1H, d, J=4.68Hz).

TABLE 3-continued

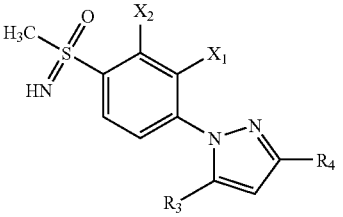

| | $X_2$ | $X_1$ | $R_4$ | $R_3$ | Mol. Wt | Yield |
|---|---|---|---|---|---|---|
| 91. | H | H | $CF_3$ | 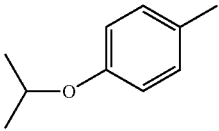 | Mol. Wt. = 423 | % Yield = 82 |

$^1$H: 1.3(6H, d, J=6.0Hz), 3.1(3H, s), 4.6(1H, m), 6.7(1H, s), 6.85(2H, d, J=8.6Hz), 7.1(2H, d, J=8.67Hz), 7.5(2H, d, J=8.52Hz), 8.0(2H, d, J=8.55Hz).

| 92. | H | H | $CF_3$ |  | Mol. Wt. = 371 | % Yield = 14 |

$^1$H, $CD_3OD$: 3.8(3H, s), 7.1(3H, m), 7.6(1H, dd, J=4.8 & 1.4Hz), 7.8(2H, d, J=8.7Hz), 8.2(2H, d, J=8.7Hz).

Preparation 4

5-Chloro-3-(4-methylsulfanylphenyl)-[2,3']bipyridinyl (Compound No. 93)

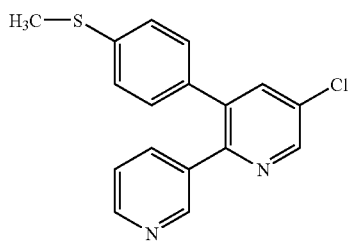

A mixture of 3-[2-(4-methylsulfanylphenyl)acetyl]pyridine (0.9 g), 2-chloromalondialdehyde (0.98 g) and ammonium acetate (1.85 g) was heated to 130° C. for 16 h. while distilling off the acetic acid formed. The reaction mixture was cooled, basified with aqueous sodium carbonate, extracted with dichloromethane (2×100 mL) and dried over anhydrous sodium sulfate. The combined organic layer was heated with activated charcoal, filtered, and evaporated under reduced pressure. The crude product was chromatographed over silicagel
using 10% to 50% ethyl acetate in petroleum ether as eluent yielding 280 mg of product as a dark yellow solid.

In like manner compounds in the table 4 were prepared following the procedure described above.

TABLE 4

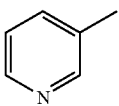

| Compound No. | $R_3$ | Molecular Weight | % yield |
|---|---|---|---|
| 93. | 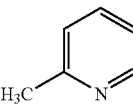 | Mol. Wt. = 312.5 | % Yield = 24.21 |

$^1$H: 2.48(3H, s), 7.06-7.08(2H, d, J=8.4Hz), 7.15-7.18(2H, d, J=8.4Hz), 7.20-7.25(1H, m), 7.67-7.69(1H, m), 7.73-7.74(1H, d, J=2.3Hz), 8.50-8.52(1H, dd, J=3.2 & 4.8Hz), 8.57(1H, d, J=1.64Hz), 8.6(1H, d, J=2.35Hz)

| 94. |  | Mol. Wt. = 326.5 | % Yield = 26.24 |

$^1$H: 2.48(3H, s), 2.53(3H, s), 7.05-7.09(3H, m), 7.19-7.16(2H, d, J=6.39Hz), 7.59-7.55(1H, d, J=8.04Hz), 7.71-7.70(1H, d, J=2.34Hz), 8.45-8.44(1H, d, J=2.25Hz), 8.64-8.63(1H, d, J=2.37Hz)

The sulfides obtained as per the procedure described in preparation 4 were converted to the corresponding sulfoxides by a procedure similar to that described in preparation 2 above.

TABLE 5

[Structure: methylsulfinyl-phenyl-pyridine with Cl and R3 substituents]

| Compound No. | R3 | Molecular Weight | % yield |
|---|---|---|---|
| 95. | 3-pyridyl | Mol. Wt. = 328.5 | % Yield = 44.16 |

$^1$H: 2.76(3H, s), 7.28-7.30(1H, d, J=4.95Hz),
7.34-7.37(2H, d, J=8.3Hz),
7.61-7.64(2H, d, J=8.3Hz), 7.73-7.76(1H, d, J=8Hz),
7.78-7.79(1H, d, J=2.34Hz),
8.54(2H, s), 8.72-8.73(1H, d, J=2.3Hz)

| 96. | 6-methyl-3-pyridyl | Mol. Wt. = 342.5 | % Yield = 47 |

$^1$H: 2.54(3H, s), 2.2.76(3H, s), 7.06-7.08(1H, d, J=8Hz),
7.34-7.37(2H, d, J=8.37Hz),
7.54-7.57(1H, dd, J=2.3 & 8Hz), 7.6-7.63(2H, d, J=6.4Hz), 7.7(1H, d, J=2.34Hz),
8.4(1H, d, J=2.3Hz), 8.7(1H, d, J=2.3Hz).

The sulfoxides obtained as per the procedure described in Preparation 5 were converted to the corresponding sulfoximines by a procedure similar to that described in preparation 3 above.

TABLE 6

[Structure: methylsulfoximino-phenyl-pyridine with Cl and R3 substituents]

| Compound No. | R3 | Molecular Weight | % yield |
|---|---|---|---|
| 97. | 3-pyridyl | Mol. Wt. = 343.5 | % Yield = 44 |

$^1$H: 2.75(3H, s), 7.22-7.24(1H, m),
7.33-7.36(2H, d, J=8.2Hz), 7.60-7.63(2H, d, J=8.2Hz), 7.67-7.7(1H, d, J=8Hz),
7.77-7.78(1H, d, J=2.3Hz),
8.52-8.54(2H, s), 8.72(1H, d, J=2.3Hz)

| 98. | 6-methyl-3-pyridyl | Mol. Wt. = 357.5 | % Yield = 79 |

$^1$H: 2.54(3H, s), 3.14(3H, s),
7.10-7.13(1H, d, J=8.04Hz), 7.36-7.39(2H, d, J=8Hz), 7.60-7.64(1H, dd, J=2.3 & 8.04Hz), 7.7(1H, d, J=2.3Hz),
7.96-7.98(2H, d, J=8.5Hz), 8.3(1H, d, J=2Hz), 8.7(1H,d, J=2.4Hz)

The sulfides of general formula given below were prepared according to the procedures well known in the art (for example as described in WO 0181332).

[Structure: methylthio-phenyl-furanone with X1, X2, R3 substituents]

The sulfides of general formula given above were converted to the corresponding sulfoxides by a procedure similar to that described in preparation 2 above

TABLE 7

[Structure: 4-(4-methylsulfinyl-phenyl)-furan-2(5H)-one scaffold with X₂, X₁ substituents on the phenyl and R₃ on the furanone]

| Compound No. | X₂ | X₁ | R₃ | Mol. Wt | Yield |
|---|---|---|---|---|---|
| 99. | F | H | 3,4-dichlorophenyl | Mol. Wt. = 385 | % Yield = 41.1 |

¹H: 2.9(3H, s), 5.2(2H, s), 7.05(1H, dd, J=1.5 & 10Hz), 7.2(1H, dd, J=2 & 8.3Hz), 7.3(1H, d, J=1.5 & 8.1Hz), 7.4(1H, d, J=8.3Hz), 7.5(1H, d, J=8.4Hz), 7.9(1H, t, J=7.6Hz).

| 100. | F | H | 4-chlorophenyl | Mol. Wt. = 350.5 | % Yield = 70 |

¹H: 2.9(3H, s), 5.2(2H, s), 7.05(1H, dd, J=1.5 & 10Hz), 7.3-7.4(5H, m), 7.8(1H, t, J=7.5Hz)

| 101. | F | H | phenyl | Mol. Wt. = 316 | % Yield = 33.3 |

¹H: 2.85(3H, s), 5.2(2H, s), 7.05(1H, dd, J=1.5 & 10Hz), 7.34-7.37(1H, dd, J=1.5 & 8.1Hz), 7.38-7.8(5H, m), 7.83-7.89(1H, t, J=7.7Hz).

| 102. | F | H | 3,4-difluorophenyl | Mol. Wt. = 352 | % Yield = 57.4 |

¹H: 2.87(3H, s), 5.2(2H, s), 7.03-7.07(1H, dd, J=1.5 & 10Hz), 7.16-7.3(3H, m), 7.34-7.37(1H, dd, J=1.5 & 8.1Hz), 7.9(1H, t, J=7.6Hz).

| 103. | F | H | 3,4-dimethoxyphenyl | Mol. Wt. = 376 | % Yield = 66 |

¹H: 2.85(3H, s), 3.80(3H, s), 3.9(3H, s), 5.15(2H, s), 6.86-6.89(1H, d, J=8.2Hz), 6.96-7.0(2H, m), 7.09-7.14(1H, dd, J=1.5 & 10.3Hz), 7.4(1H, dd, J=1.5 & 8.07Hz), 7.86-7.91(1H, t, J=7.6Hz).

| 104. | F | H | 4-methoxyphenyl | Mol. Wt. = 346 | % Yield = 71.5 |

¹H: 2.86(3H, s), 3.84(3H, s), 5.14(2H, s), 6.91-6.95(2H, dd, J=2 & 6.87Hz), 7.08-7.12(1H, dd, J=1.4 & 10.3Hz), 7.36-7.39(3H, m), 7.84-7.89(1H, t, J=7.6Hz)

TABLE 7-continued

[Structure: 4-(4-methylsulfinyl-phenyl with X₂, X₁ substituents)-3-R₃-furan-2(5H)-one]

| Compound No. | X₂ | X₁ | R₃ | Mol. Wt | Yield |
|---|---|---|---|---|---|
| 105. | F | H | (4-methylphenyl) | Mol. Wt. = 330 | % Yield = 35.4 |

¹H: 2.39(3H, s), 2.85(3H, s), 5.15(2H, s), 7.07-7.1(1H, dd, J=1.5 & 10.35Hz), 7.2-7.32(4H, m), 7.34-7.38(1H, dd, J=1.5 & 8.1Hz), 7.84-7.89(1H, t, J=7.6Hz)

The sulfoxides of table 7 were converted to the corresponding sulfoximines by a procedure similar to that described in preparation 3 above.

TABLE 8

[Structure: 4-(4-(S-methylsulfonimidoyl)-phenyl with X₂, X₁ substituents)-3-R₃-furan-2(5H)-one]

| Compound No. | X₂ | X₁ | R₃ | Mol. Wt | % Yield |
|---|---|---|---|---|---|
| 106. | F | H | (3,4-dichlorophenyl) | Mol. Wt. = 400 | % Yield = 77 |

¹H: 3.3(3H, s), 5.18(2H, s), 7.15-7.27(3H, m), 7.7.47-7.5(1H, d, J=8.3Hz), 7.58(1H, d, J=2Hz), 7.97-8.02(1H, t, J=7.6Hz).

| 107. | F | H | (4-chlorophenyl) | Mol. Wt. = 365.5 | % Yield = 77 |

¹H: 3.3(3H, s), 5.17(2H, s), 7.15-7.19(1H, dd, J=1.56 & 10.32Hz), 7.24(1H, d, J=1.6Hz), 7.32-7.42(4H, m), 7.95-8.0(1H, t, J=7.8Hz)

| 108. | F | H | (phenyl) | Mol. Wt. = 331 | % Yield = 47 |

¹H, dMSO-d₆: 3.30(3H, s), 5.39(2H, s), 7.32-7.36(3H, m), 7.42-7.5(4H, m), 7.83-7.88(1H, t, J=7.9Hz).

TABLE 8-continued

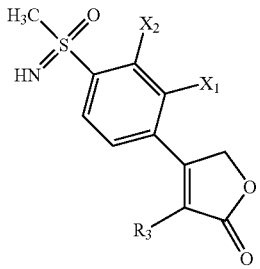

| Compound No. | X₂ | X₁ | R₃ | Mol. Wt | % Yield |
|---|---|---|---|---|---|
| 109. | F | H | (3,4-difluorophenyl) | Mol. Wt. = 367 | % Yield = 67 |

¹H: 3.3(3H, s), 5.17(2H, s), 7.15-7.34(5H, m), 7.97-8.02(1H, t, J=7.7Hz).

| 110. | F | H | (3,4-dimethoxyphenyl) | Mol. Wt. = 391 | % Yield = 30 |

¹H: 3.3(3H, s), 3.8(3H, s), 3.9(3H, s), 5.15(2H, s), 6.85-6.88(1H, d, J=8.3Hz), 6.93-6.96(1H, d, J=2 & 8.3Hz), 7.0(1H, d, J=1.5Hz), 7.20-7.24(1H, dd, J=1.5 & 8.1Hz), 7.29-7.32(1H, dd, J=1.5 & 8.1Hz), 7.93-7.98(1H, t, J=7.8Hz).

| 111. | F | H | (4-methoxyphenyl) | Mol. Wt. = 361 | % Yield = 48 |

¹H: 3.3(3H, s), 3.85(3H, s), 5.14(2H, s), 6.92-6.95(2H, d, J=6.78Hz), 7.18-7.22(1H, dd, J=1.5 & 10.56Hz), 7.27-7.30(1H, dd, 1.59 & 8.25Hz), 7.35-7.38(2H, d, J=6.8Hz), 7.92-7.98(1H, t, J=7.8Hz)

| 112. | F | H | (4-methylphenyl) | Mol. Wt. = 345 | % Yield = 69 |

¹H: 2.39(3H, s), 3.28(3H, s), 5.15(2H, s), 7.17-7.13(6H, m), 7.91-7.97(1H, t, J=7.8Hz).

Preparation 5

3-(3-Fluorophenyl)-4(4-methylsulfanyl)-3H-thiazol-2-one (Compound No. 113)

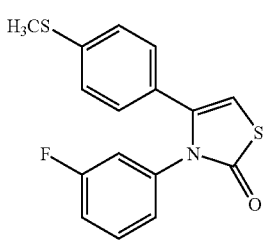

Step 1: Preparation of ethyl(3-fluorophenyl)thiocarbamate

A solution of 3-fluoroaniline (4 g) and bis(ethoxythiocarbanyl)sulfide (7.56 g) in 50 mL EtOH was stirred at ambient temperature for 24 h. The solvent was evaporated and the residue was triturated with pentane yielding 4.0 g of product as a light cream solid.

Step 2: Preparation of 3-(3-fluorophenyl)-4-hydroxy-4(4-methylsulfanylphenyl)-thiazolidin-2-one A mixture of ethyl(3-fluorophenyl)thiocarbamate (1 g) (prepared in step 1) and 2-bromo-1-(4-methylsulfanylphenyl)ethanone (1.4 g) in 20 mL of THF was refluxed for 8 h. A slight insoluble material was filtered, the solvent was then evaporated and the residue was taken up in dichloromethane. The organic solution was dried over sodium sulfate, evaporated and the residue was crystallized from ether giving 0.8 g of product as a pale yellow solid.

Step 3: Preparation of 3-(3-fluorophenyl)-4(4-methylsulfanyl)-3H-thiazol-2-one To a solution of 3-(3-fluorophenyl)-4-hydroxy-4-(4-methylsulfanylphenyl)-thiazolidin-2-one (1 g) (prepared in step 2) in ethanol (50 mL) was added 0.5 mL of concentrated HCl and refluxed for 5 h. The reaction mixture was cooled to 25° C. Precipitated solid was filtered, washed with ethanol and dried to yield 0.8 g of product as a pale yellow solid.

In like manner compounds in the table 9 were prepared following the procedure described above

TABLE 9

| Compound No. | R₃ | Molecular Weight | % yield |
|---|---|---|---|
| 113. | 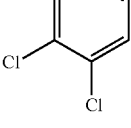 | Mol. Wt. = 317 | % Yield = 84 |
| | ¹H: 2.45(3H, s), 6.18(1H, s), 6.89-7.09(6H, complex), 7.28-7.31(2H, m). | | |
| 114. | 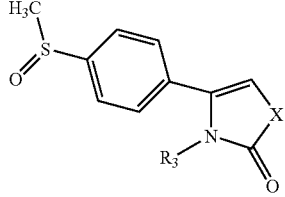 | Mol. Wt. = 368 | % Yield = 84 |
| | ¹H: 2.46(3H, s), 6.18(1H, s), 6.88-6.92(1H, dd, J=2.43Hz & 8.5Hz), 6.96-6.99(2H, d, J=8.4Hz), 7.09-7.12(2H, d, J=7.5Hz), 7.35(1H, d, J=2.4Hz), 7.37-7.40(1H, d, J=8.6Hz). | | |

The sulfides described above were converted to the corresponding sulfoxides by a procedure similar to that described in preparation 2.

TABLE 10

| Compound No. | X | R₃ | Mol. Wt | % Yield |
|---|---|---|---|---|
| 115.* | O | 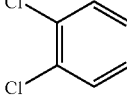 | Mol. Wt. = 368 | % Yield = 64.5 |
| | | ¹H: 2.74(3H, s), 6.9-7.0(1H, d, J=8.6 & 2.5Hz), 7.1(1H, s), 7.2(2H, d, J=8.5Hz), 7.4(1H, d, J=2.5Hz), 7.4(1H, d, J=8.6Hz), 7.6(2H, d, J=8.5Hz). | | |

TABLE 10-continued

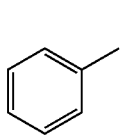

| Compound No. | X | R₃ | Mol. Wt | % Yield |
|---|---|---|---|---|
| 116.* | O | 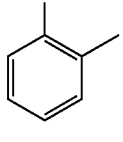 | Mol. Wt. = 378 | % Yield = 73 |
| | | ¹H: 2.74(3H, s), 7.0(2H, d, J=8.7Hz), 7.09(1H, s), 7.2(2H, d, J=8.4Hz), 7.5(2H, d, J=8.7Hz), 7.6(2H, d, J=8.4Hz). | | |
| 117.* | O | 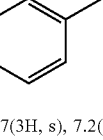 | Mol. Wt. = 299 | % Yield = 28 |
| | | ¹H: 2.7(3H, s), 7.1(1H, s), 7.2(4H, m), 7.4(3H, m), 7.5(2H, d, J=8.5Hz). | | |
| 118.* | O | 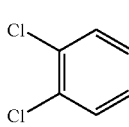 | Mol. Wt. = 317 | % Yield = 53 |
| | | ¹H: 2.7(3H, s), 7.2(3H, m), 7.27(2H, d, J=8.3Hz), 7.3-7.4(2H, m), 7.6(2H, d, J=8.4Hz). | | |
| 119. | S | 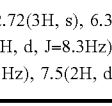 | Mol. Wt. = 333 | % Yield = 76 |
| | | ¹H: 2.7(3H, s), 6.3(1H, s), 6.4-6.9(2H, m), 7.0-7.08(2H, m), 7.23-7.36(3H, m), 7.5(2H, d, J=8.2Hz). | | |
| 120. | S | 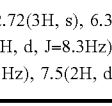 | Mol. Wt. = 384 | % Yield = 88 |
| | | ¹H: 2.72(3H, s), 6.3(1H, s), 6.9(1H, dd, J=2.4 & 8.5Hz), 7.2(2H, d, J=8.3Hz), 7.3(1H, d, J=2.4Hz), 7.4(1H, d, J=8.5Hz), 7.5(2H, d, J=8.3Hz). | | |

*The corresponding sulfides were prepared according to procedures known in the art.

Preparation 6

4-(4-Methylsulfoximinylphenyl)-3-(3,4-dichlorophenyl)-3H-oxazol-2-one (Compound No. 121)

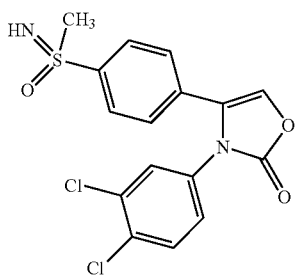

To a stirred solution of 4-(4-methylsulfinylphenyl)-3-(3,4-dichlorophenyl)-3H-oxazol-2-one (Compound no. 115) (1.1 g) in 20 ml of dichloromethane was added O-mesitylenesulfonyl hydroxylamine (1.12 g) at 25° C. and stirred for 12 h. The reaction mixture was basified to pH 11 with 2N NaOH solution, stirred for 30 min and extracted with dichloromethane (3×100 mL), The organic extract was dried over anhydrous sodium sulfate and evaporated under reduced pressure.

The crude product obtained was chromatographed using 20 to 60% ethyl acetate in petroleum ether as eluent to give 670 mg pure product as a gum.

In like manner compounds in the table 11 were prepared following the procedure described above.

TABLE 11

| Compound No. | X | R³ | Mol. Wt | Yield |
|---|---|---|---|---|
| 121. | O | 3,4-dichlorophenyl | Mol. Wt. = 383 | % Yield = 32 |

¹H, CD₃OD: 3.6(3H, s), 7.0-7.1(1H, d, J=2.4 & 8.6Hz), 7.4-7.5(4H, m), 7.59(1H, s), 8.0(2H, d, J=8.7Hz).

| 122. | O | 4-bromophenyl | Mol. Wt. = 393 | % Yield = 57.7 |

¹H: 3.1(3H, s), 7.0(2H, d, J=6.7Hz), 7.09(1H, s), 7.2(2H, d, J=6.2Hz), 7.5(2H, d, J=8.7Hz). 7.9(2H, d, J=8.4 Hz).

TABLE 11-continued

| Compound No. | X | R³ | Mol. Wt | Yield |
|---|---|---|---|---|
| 123. | O | phenyl | Mol. Wt. = 314 | % Yield = 47 |

¹H, CDCl₃ + DMSO-d₆: 3.2(3H, s), 7.2(2H, d, J=8.1Hz), 7.3(2H, d, J=9.0Hz), 7.4(3H, m), 7.8(2H, d, J=8.5Hz), 8.1(1H, s).

| 124. | O | 2-fluorophenyl | Mol. Wt. = 332 | % Yield = 53 |

¹H: 3.08(3H, s), 7.1(3H, m), 7.2(2H, d, J=8.49Hz), 7.3-7.4(2H, m), 7.9(2H, d, J=8.5Hz).

| 125. | S | 3-fluorophenyl | Mol. Wt. = 348 | % Yield = 60 |

¹H, CD₃OD: 3.8(3H, s), 6.8(1H, s), 7.0(1H, d, J=8.0Hz), 7.09-7.16(2H, m), 7.3-7.4(1H, dd, J=6.3 & 8.0Hz), 7.6 (2H, d, J=8.6Hz), 8.0(2H, d, J=8.6Hz).

| 126. | S | 3,4-dichlorophenyl | Mol. Wt. = 399 | % Yield = 61 |

¹H, dMSO-d₆: 3.5(3H, s), 6.9(1H, s), 7.2(1H, dd, J=2.4 & 8.5Hz), 7.5(2H, d, J=8.5Hz), 7.6(1H, d, J=8.5Hz), 7.7 (1H, d, J=2.4Hz), 7.9(2H, d, J=8.4Hz).

Preparation 7

3-(3,4-Dichlorophenyl)-4-[4-(N-chloroacetyl) methylsulfoximinylphenyl]-3H-oxazol-2-one (Compound No. 128)

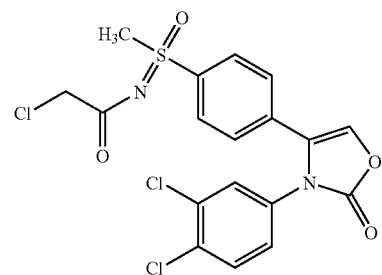

To a solution of 3-(3,4-dichlorophenyl)-4-[4-methylsulfoximinylphenyl]-3H-oxazol-2-one (Compound No. 119) (100 mg) and triethyl amine (0.18 mL) in dry THF (5 mL) was added chloroacetyl chloride (59 mg) at 0° C. The reaction mixture was allowed to warm upto 25° C. and stirred for 2 h. The reaction mixture was washed with water extracted with dichloromethane (3×10 mL). The organic extract was washed with water followed by brine solution, dried over calcium chloride and evaporated under reduced pressure. The crude product was purified over silicagel using 50% ethyl acetate in petroleum ether as eluent yielding 70 mg of product as a yellow solid.

In like manner following compounds in table 12 were prepared by a procedure similar to that described above.

TABLE 12

| Compound No. | R₁ | R₃ | Mol. Wt | Yield |
|---|---|---|---|---|
| 127. | (acetyl, -C(O)CH₃) | 3,4-dichlorophenyl | Mol. Wt. = 424 | % Yield = 69 |

$^1$H: 2.1(3H, s), 3.3(3H, s), 6.9(1H, d, J=2.4 & 8.5Hz), 7.1(1H, s), 7.3(2H, d, J=8.5Hz), 7.4(1H, d, J=2.5Hz), 7.4(1H, d, J=8.5 Hz), 7.9(2H, d, J=8.5Hz).

| 128. | -C(O)CH₂Cl | 3,4-dichlorophenyl | Mol. Wt. = 460 | % Yield = 50 |

$^1$H: 3.3(3H, s), 4.1(2H, s), 6.9(1H, dd, J=2.5 & 8.5Hz), 7.1(1H, s), 7.3(2H, d, J=8.6Hz), 7.4(1H, d, J=2.4Hz), 7.4(1H, d, J=8.5 Hz), 7.9(2H, d, J=8.67Hz).

| 129. | -S(O)₂CH₃ | 3,4-dichlorophenyl | Mol. Wt. = 461 | % Yield = 66 |

$^1$H: 3.1(3H, s), 3.4(3H, s), 6.9(1H, dd, J=2.5 & 8.6Hz), 7.1(1H, s), 7.3(2H, d, J=8.5Hz), 7.4(1H, d, J=2.5Hz), 7.4(1H, d, J=8.5 Hz), 7.9(2H, d, J=8.5Hz).

| 130. | -S(O)₂-(4-tolyl) | 3,4-dichlorophenyl | Mol. Wt. = 537 | % Yield = 53 |

$^1$H: 2.4(3H, s), 3.4(3H, s), 6.9(1H, dd, J=2.5 & 8.6Hz), 7.1(1H, s), 7.2-7.3(4H, m), 7.4(1H, d, J=2.4Hz), 7.4(1H, d, J=8.6Hz), 7.8(2H, d, J=8.3Hz), 7.9(2H, d, J=8.6Hz).

Preparation 8

3-(4-Methoxyphenyl)-4-(4-methylsulfanyl)-5-methyl-isoxazole (Compound No. 138)

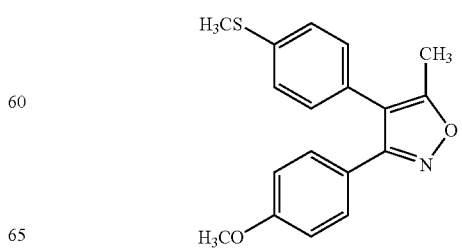

Step 1: Preparation of 3-(4-methoxyphenyl)-4-(4-methylsulfanyl)-5-methyl-4,5-dihydro-isoxazol-5-ol To a stirred solution of 1-(4-methoxyphenyl)-2-(4-methylsulfanylphenyl)ethanone oxime (4.5 g) in dry THE (30 mL), was added a solution of n-butyl lithium (1.3 M, 30.7 mL) in hexane at −70° C. over a period of 30 minutes. The reaction mixture was warmed to 20° C. over a period of 2 h. To this was added ethyl acetate (2.1 mL) and the reaction mixture was stirred the same temperature for 30 minutes. The reaction mixture was quenched with cold water (100 mL) and extracted with ethyl acetate (3×100 mL). The organic extract was washed with water (100 mL), brine (100 mL), dried over sodium sulphate and evaporated under reduced pressure. The crude product was chromatographed over silicagel using 10% ethyl acetate in petroleum ether as eluent, yielding 4.1 g of pure product as a pale yellow solid.

Step 2: Preparation of 3-(4-methoxyphenyl)-4-(4-methylsulfanyl)-5-methyl-isoxazole A solution of 3-(4-methoxyphenyl)-4-(4-methylsulfanyl)-5-methyl-4,5-dihydro-isoxazol-5-ol (2.1 g) and PTSA (100 mg) in benzene (20 mL) was refluxed for 30 minutes. The reaction mixture was cooled to 25° C., diluted with 50 mL of benzene and washed with water (50 mL) followed by brine solution (50 mL). The organic extract was dried over sodium sulphate and evaporated under reduced pressure to yield 1.7 g of product as a thick liquid.

Preparation 9

5-Chloro-4(4-methyl sulfanylphenyl)-3-phenyl isoxazole (compound No. 136)

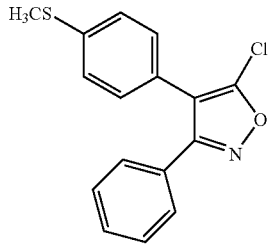

Step 1: Preparation of 5-hydroxy-4(4-methylsulfanylphenyl)-3-phenyl isoxazole

To a stirred solution of 1-phenyl-2-(4-methylsulfanylphenyl) ethanone oxime (2.0 g) in dry THF (20 mL), was added a solution of n-butyl lithium (0.98 M. 25 mL) in hexane at −70° C. over a period of 30 minutes. The reaction mixture was warmed to 20° C. over a period of 2 h. To this was added solid $CO_2$ (25 g) and the reaction mixture was stirred at the same temperature for 30 minutes. The reaction mixture was quenched with cold 1N HCl (20 mL) and extracted with ethyl acetate (3×50 mL). The organic extract was washed with water (100 mL); brine (100 mL), dried over sodium sulphate and evaporated under reduced pressure. The crude product was chromatographed over silicagel using 10% ethyl acetate in petroleum ether as eluent, yielding 1.2 g of pure product as a thick liquid.

Step 2: Preparation of 5-chloro-4(4-methylsulfanylphenyl)-3-phenyl isoxazole

To a mixture of 5-hydroxy-4(4-methylsulfanylphenyl)-3-phenyl isoxazole (Compound prepared in step 1) (0.6 g) and triethyamine (0.43 mL) was added $POCl_3$ (10 mL) under stirring and the reaction mixture was heated to 70° C. for 4 h. Solvents were evaporated and the crude product was chromatographed over silicagel using petroleum ether as eluent to yield 310 mg of product as a pale yellow solid.

In like manner compounds in the following table were prepared following the procedure described in preparation 8.

TABLE 13

| Compound No. | $R_3$ | $R_4$ | Mol. Wt | % Yield |
|---|---|---|---|---|
| 131. | phenyl | —CH$_2$CH$_3$ | Mol. Wt. = 295 | % Yield = 44 |
| | $^1$H: 1.3(3H, t, J=7.6Hz), 2.7(3H, s), 2.8(2H, q, J=7.6Hz), 7.2-7.6(9H, complex). | | | |
| 132. | phenyl | —CH$_2$OCH$_3$ | Mol. Wt. = 311 | % Yield = 60 |
| | $^1$H: 2.5(3H, s), 3.4(3H, s), 4.5(2H, s), 7.1-7.2(4H, m), 7.3(3H, m), 7.4(2H, m). | | | |

TABLE 13-continued

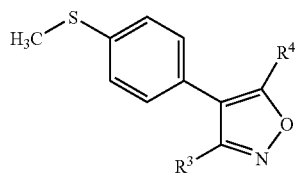

| Compound No. | R₃ | R₄ | Mol. Wt | % Yield |
|---|---|---|---|---|
| 133. | 4-fluorophenyl | —CH₃ | Mol. Wt. = 299 | % Yield = 35 |

¹H: 2.4(3H, s), 2.7(3H, s), 7.0(2H, t, J=8.7Hz), 7.3(4H, m), 7.6(2H, d, J=8.4Hz).

| 134. | 4-chlorophenyl | —CH₃ | Mol. Wt. = 315.5 | % Yield = 85 |

¹H: 2.4(3H, s), 2.7(3H, s), 7.2-7.3(6H, m), 7.6(2H, d, J=8.2Hz).

| 135. | —CH₂CH₃ | phenyl | Mol. Wt. = 295 | % Yield = 23 |

¹H: 1.2(3H, t, J=7.5Hz), 2.6(2H, q, J=7.5Hz), 2.8(3H, s), 7.3(3H, m), 7.4(4H, m), 7.7(2H, d, J=8.4Hz).

| 136. | phenyl | —Cl | Mol. Wt. = 301.5 | % Yield = 49 |

¹H: 2.7(3H, s), 7.2-7.4(7H, complex), 7.6(2H, d, J=8.3Hz)

| 137. | phenyl | —CH₃ | Mol. Wt. = 281 | % Yield = 94 |

¹H: 2.45(3H, s), 2.5(3H, s), 7.1(2H, d, J=8.44Hz), 7.2(2H, d, J=8.44Hz), 7.3(3H, m), 7.4(2H, m)

| 138. | 4-methoxyphenyl | —CH₃ | Mol. Wt. = 311 | % Yield = 85 |

¹H: 2.4(3H, s), 2.5(3H, s), 3.8(3H, s), 6.8(2H, dd, J=6.8 & 2.0Hz), 7.1(2H, dd, J=6.5 & 1.9Hz). 7.2(2H, dd, J=6.57 & 1.9Hz), 7.3(2H, dd, J=6.8 & 2.0Hz)

The sulfides of table 13 were converted to the corresponding sulfoxides by a procedure similar to that described in preparation 2:

TABLE 14

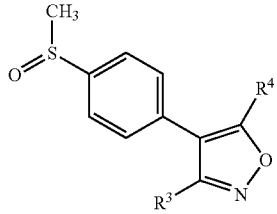

| Compound No. | R₃ | R₄ | Mol. Wt | Yield |
|---|---|---|---|---|
| 139. | 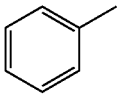 |  CH₃ | Mol. Wt. = 311 | % Yield = 67 |
| | ¹H: 1.3(3H, t, J=7.6Hz), 2.7(3H, s), 2.8(2H, q, J=7.6Hz), 7.2-7.6(9H, complex). | | | |
| 140. | 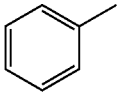 | —CH₂OCH₃ | Mol. Wt. = 327 | % Yield = 72 |
| 141. | 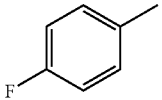 | —CH₃ | Mol. Wt. = 315 | % Yield = 87 |
| | ¹H: 2.4(3H, s), 2.7(3H, s), 7.0(2H, t, J=8.7Hz), 7.3(4H, m), 7.6(2H, d, J=8.4Hz). | | | |
| 142. | 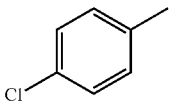 | —CH₃ | Mol. Wt. = 331.5 | % Yield = 79 |
| | ¹H: 2.4(3H, s), 2.7(3H, s), 7.2-7.3(6H, m), 7.6(2H, d, J=8.2Hz). | | | |
| 143. | 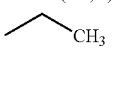 CH₃ | 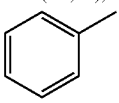 | Mol. Wt. = 311 | % Yield = 71 |
| | ¹H: 1.2(3H, t, J=7.5Hz), 2.6(2H, q, J=7.5Hz), 2.8(3H, s), 7.3(3H, m), 7.4(4H, m), 7.7(2H, d, J=3.4Hz). | | | |
| 144. | 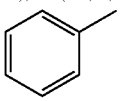 | —Cl | Mol. Wt. = 317.5 | % Yield = 51 |
| | ¹H: 2.7(3H, s), 7.2-7.4(7H, complex), 7.6(2H, d, J=8.3Hz) | | | |
| 145. | 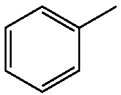 | —CH₃ | Mol. Wt. = 297 | % Yield = 72 |
| | ¹H: 2.5(3H, s), 2.8 (3H, s), 7.3-7.4(7H, m), 7.6(2H, d, J=8.5Hz) | | | |
| 146. | 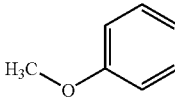 | —CH₃ | Mol. Wt. = 327 | % Yield = 78 |
| | ¹H: 2.5(3H, s), 2.8(3H, s), 3.8(3H, s), 6.8(2H, dd, J=6.82 & 2.02Hz), 7.3(4H, m), 7.6(2H, d, J=8.3Hz) | | | |

The sulfoxides of table 14 were converted to the corresponding sulfoximines by a procedure similar to that described in preparation 3:

TABLE 15

| Compound No. | R₃ | R₄ | Mol. Wt | Yield |
|---|---|---|---|---|
| 147. | phenyl | —CH₂CH₃ (ethyl) | Mol. Wt. = 326 | % Yield = 71 |

¹H, dMSO-d₆: 1.3(3H, t, J=7.6Hz), 2.8(2H, q, J=7.6Hz), 3.79(3H, s), 7.4(5H, m), 7.6(2H, d, J=8.5Hz), 8.1(2H, d, J=8.5Hz).

| 148. | phenyl | —CH₂OCH₃ | Mol. Wt. = 342 | % Yield = 26 |

¹H, dMSO-d₆: 3.3(3H, s), 3.4(3H, s), 4.5(2H, s), 7.4(5H, m), 7.5(2H, d, J=8.4 Hz), 8.0(2H, d, J=8.4Hz).

| 149. | 4-F-phenyl | —CH₃ | Mol. Wt. = 330 | % Yield = 41 |

¹H: 2.4(3H, s), 2.7(3H, s), 7.0(2H, t, J=8.7Hz), 7.3(4H, m), 7.6(2H, d, J=8.4Hz).

| 150. | 4-Cl-phenyl | —CH₃ | Mol. Wt. = 346.5 | % Yield = 86 |

¹H, dMSO-d₆: 3.4(3H, s), 3.5(3H, s), 7.3(2H, d, J=8.5Hz), 7.4(2H, d, J=8.5Hz), 7.5(2H, d, J=8.4Hz), 8.0(2H, d, J=8.7Hz).

| 151. | —CH₂CH₃ (ethyl) | phenyl | Mol. Wt. = 326 | % Yield = 63 |

¹H, dMSO-d₆: 1.1(3H, t, J=7.5Hz), 2.6(2H, q, J=7.5Hz), 3.6(3H, s), 7.4(5H, m), 7.7(2H, d, J=8.4Hz), 8.1(2H, d, J=8.4Hz).

| 152. | phenyl | —Cl | Mol. Wt. = 332.5 | % Yield = 57 |

¹H, dMSO-d₆: 3.3(3H, s), 7.3-7.4(5H, m), 7.5(2H, d, J=8.4Hz), 8.0(2H, d, J=8.4Hz)

| 153. | phenyl | —CH₃ | Mol. Wt. = 312 | % Yield = 87 |

¹H: 2.5(3H, s), 3.2(3H, s), 7.3-7.4(7H, m), 7.6(2H, dd, J=6.7 & 1.8Hz)

| 154. | 4-OCH₃-phenyl | —CH₃ | Mol. Wt. = 342 | % Yield = 30.2 |

¹H: 2.5(3H, s), 3.1(3H, s), 3.8(3H, s), 6.8(2H, d, J=8.8Hz), 7.3(4H, m), 8.0(2H, d, J=8.3Hz)

Preparation 10

5-(4-Methylsulfoximinylphenyl)-1-phenyl-3-trifluoromethyl-1H-pyrazole (Compound No. 155)

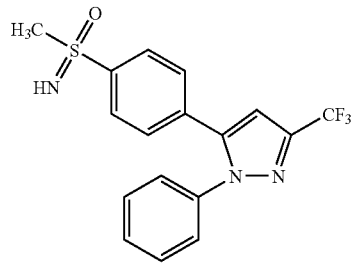

Step 1: Preparation of 5-(4-methylsulfanylphenyl)-1-phenyl-3-trifluoromethyl-1H-pyrazole A solution of 4,4,4-trifluoro-(4-methylsulfanylphenyl)-butane-1,3-dione (3.0 g) and phenyl hydrazine hydrochloride (1.18 g) in ethanol (20 mL) was refluxed for 7 h. The solvent was evaporated and the residue was chromatographed over silicagel using 20% ethyl acetate in petroleum ether as eluent yielding 2.25 g (% yield=83, Mol. Weight=334) of product as a gum.
$^1$H: 2.4(3H, s) 6.7(1H, s), 7.12(2H, dd, J=6.3 & 2.3 Hz), 7.15(2H, dd, J=6.3 & 2.2 Hz), 7.3(5H, m).

Step 2: Preparation of 5-(4-methylsulfinylphenyl)-1-phenyl-3-trifluoromethyl-1H-pyrazole Title compound (1.3 g, % yield=60, Mol. weight=350) was prepared from 5-(4-methyl sulfanylphenyl)-1-phenyl-3-trifluoromethyl-1H-pyrazole (2.1 g) (prepared in step 1 above) by a procedure similar to that described in preparation 2.
$^1$H: 2.7 (3H, s), 6.8(1H, s), 7.3(2H, dd, J=6.2 & 2.0 Hz), 7.4(5H, m), 7.6(2H, dd, J=8.2 & 1.6 Hz), Step 3: Preparation of 5-(4-methylsulfoximinylphenyl)-1-phenyl-3-trifluoromethyl-1H-pyrazole (Compound. No. 155)

Title compound (310 mg, % yield=45, Mol. weight=365) was prepared from 5-(4-methyl sulfinylphenyl)-1-phenyl-3-trifluoromethyl-1H-pyrazole (600 mg)(prepared in step 2 above) by a procedure similar to that described in preparation 3.
$^1$H, CD$_3$OD: 3.8(3H, s), 7.17(1H, s), 7.3(2H, m), 7.4(3H, m), 7.7(2H, dd, J=8.7 & 1.8 Hz), 8.1(2H, dd, J=8.7 & 1.8 Hz).

Preparation 11

Hydrochloride salt of 5-(3-fluoro-4-methoxyphenyl)-1-(4-methylsulfoximinylphenyl)-3-trifluoromethyl-1H-pyrazole (Compound No. 167)

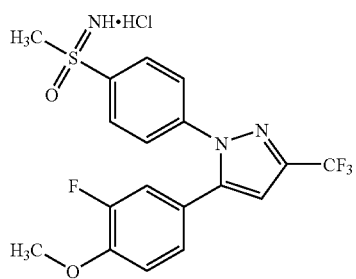

To 5-(3-fluoro-4-methoxyphenyl)-1-(4-methylsulfoximinylphenyl)-3-trifluoromethyl-1H-pyrazole (Compound. No. 74) (500 mg), methanolic HCl (10 mL, 15%) was added and stirred at 25-30° C. for 0.5 h. The solvent was evaporated under reduced pressure and the residual oil was stirred with diisopropyl ether to afford the product (440 mg) as a off white solid.

Preparation 12

Bisulphate salt of 5-(3-methoxy-4-methylphenyl)-1-(4-methylsulfoximinyl-phenyl)-3-trifluoromethyl-1H-pyrazole (Compound No. 168)

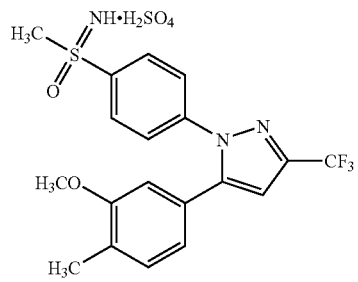

To 5-(3-methoxy-4-methylphenyl)-1-(4-methylsulfoxmi-nylphenyl)-3-trifluoromethyl-1H-pyrazole (Compound No. 75) (120 mg), a chilled solution of acetone (10 mL) containing sulfuric acid (28 mg) was added and stirred at 0° C. for 30 minutes. The solvent was evaporated under a flow of nitrogen and the residue was stirred with diisopropyl ether to afford the product (75 mg) as an off white solid.

In like manner compounds in the table 16 were prepared following the procedure described for the preparation of 11-12.

TABLE 16

| Compound No. | Free-base No. | Salt prepared | Melting Point (° C.)* |
|---|---|---|---|
| 156. | 61 | HCl | 182 |
| 157. | 62 | HCl | 200 |
| 158. | 63 | HCl | 171 |
| 159. | 64 | HCl | 178 |
| 160. | 66 | HCl | 163 |
| 161. | 68 | H$_2$SO$_4$ | 135 |
| 162. | 69 | H$_2$SO$_4$ | 195 |
| 163. | 70 | HCl | 150 |
| 164. | 71 | HCl | 170 |
| 165. | 72 | HCl | 178 |
| 166. | 73 | HCl | 170 |
| 167. | 74 | HCl | 168 |
| 168. | 75 | H$_2$SO$_4$ | 192 |
| 169. | 77 | HCl | 68 |
| 170. | 78 | HCl | 163 |
| 171. | 79 | H$_2$SO$_4$ | 141 |
| 172. | 80 | H$_2$SO$_4$ | 181 |
| 173. | 81 | H$_2$SO$_4$ | 165 |
| 174. | 82 | H$_2$SO$_4$ | 174 |
| 175. | 83 | H$_2$SO$_4$ | 199 |
| 176. | 84 | H$_2$SO$_4$ | 214 |
| 177. | 85 | H$_2$SO$_4$ | 115 |
| 178. | 92 | HCl | 168 |
| 179. | 121 | HCl | 178 |
| 180. | 123 | HCl | 184 |
| 181. | 124 | HCl | 170 |
| 182. | 125 | HCl | 120 |
| 183. | 126 | HCl | 176 |
| 184. | 147 | HCl | 166 |

TABLE 16-continued

| Compound No. | Free-base No. | Salt prepared | Melting Point (° C.)* |
|---|---|---|---|
| 185. | 148 | HCl | 171 |
| 186. | 149 | HCl | 169 |
| 187. | 151 | HCl | 169 |
| 188. | 152 | HCl | 158 |
| 189. | 153 | HCl | 168 |
| 190. | 155 | HCl | 153 |

*The melting points were uncorrected and may vary in the range of ±4° C.

We claim:

1. A compound of formula (I), their tautomers, their pharmaceutically acceptable salts, and their pharmaceutically acceptable compositions, wherein G represents one of A, B, C, E, or F as described below:

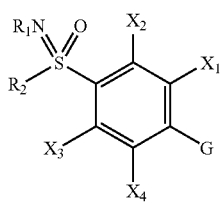
(I)

G =

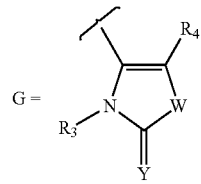 A

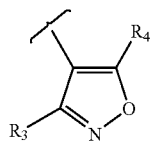 B

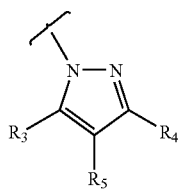 C

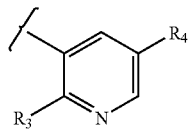 E

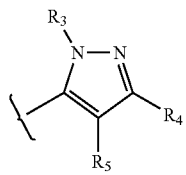 F $R_1$ represents hydrogen, substituted or unsubstituted groups selected the group consisting of from alkyl, aralkyl, acyl, alkylsulfonyl, and arylsulfonyl groups; $R_2$ represents alkyl, aralkyl, alkoxy or —NHR where R represents hydrogen or a lower alkyl group which may be suitably substituted; $X_1$, $X_2$, $X_3$, and $X_4$ may be same or different and represent hydrogen, cyano, nitro, halo, carboxyl, formyl, hydrazino, azido, amino, thio, hydroxy, or a substituted or unsubstituted group selected from the group consisting of alkyl which may be linear or branched, alkenyl, cycloalkyl, alkoxy, cycloalkoxy, cycloalkoxyalkyl, haloalkoxy, hydroxyalkyl, alkoxyalkyl, thioalkyl, carboxyalkyl, haloalkyl, aminoalkyl, cyanoalkyl, alkylthio, alkylsulfinyl, alkylsulfonyl, alkoxycarbonylalkyl, acyl, acyloxy, acyloxyalkyl, aralkyl, aryloxy, aralkoxy, aryloxyalkyl, aralkoxyalkyl, aralkenyl, acylamino, alkylamino, dialkylamino, aralkylamino, alkoxyamino, hydroxylamino, alkoxycarbonyl, and aralkoxycarbonyl groups; $R_3$ represents a substituted or unsubstituted alkyl, or a substituted or unsubstituted, single or fused group selected from the group consisting of aryl, aralkenyl, heteroaryl, and heterocyclic groups; $R_4$ and $R_5$ represent hydrogen atom, halogen atom, carboxy, or a substituted or unsubstituted group selected from the group consisting of linear or branched alkyl, alkoxycarbonyl, hydroxyalkyl, alkoxyalkyl, and phenyl groups; Y represents O or S; and W represents O or S.

2. The compound as claimed in claim 1, wherein the substituents on $R_3$ and $R_4$ represent a cyano, nitro, halo, carboxyl, amino, thio, hydroxy, or a substituted or unsubstituted group selected from the group consisting of alkyl which may be linear or branched, perhaloalkyl, alkoxy, acyl, acyloxy, oxo, carboxyalkyl, haloalkyl, aminoalkyl, haloalkoxy, hydroxyalkyl, alkoxyalkyl, thioalkyl, alkylthio, alkylsulfinyl, alkylsulfonyl, alkylsulfoximinyl, acylamino, N-alkylamino, N,N-dialkylamino, alkoxycarbonyl, aminocarbonyl, and-of cycloalkyl groups.

3. The compound as claimed in claim 1,wherein the substituents on $X_1$, $X_2$, $X_3$, and $X_4$ represent a cyano, nitro, halo, carboxyl, hydrazino, azido, formyl, amino, thio, hydroxy or a substituted or unsubstituted group selected from the group consisting of alkyl which may be linear or branched, alkoxy, alkoxycarbonyl, acyl, acylamino, acyloxy, hydrazinoalkyl, alkylhydrazido, carboxyalkyl, haloalkyl, aminoalkyl, haloalkoxy, hydroxyalkyl, alkoxyalkyl, thioalkyl, alkylthio, alkylsulfinyl, alkylsulfonyl, aryl, aralkyl, aryloxy, aralkoxy, aryloxyalkyl, aralkoxyalkyl, alkoxycarbonyl, and amidino groups.

4. The compound as claimed in claim 1, wherein the pharmaceutically acceptable salts are salts of tartaric acid, mandelic acid, fumaric acid, malic acid, lactic acid, maleic acid, salicylic acid, citric acid, ascorbic acid, benzene sulfonic acid, p-toluene sulfonic acid, hydroxynaphthoic acid, methane sulfonic acid, acetic acid, benzoic acid, succinic acid, palmitic acid, hydrochloric acid, hydrobromic acid, sulfuric acid, or nitric acid.

5. A pharmaceutical composition comprising one or more compounds as claimed in claim 1 or a pharmaceutically-acceptable salt thereof and a pharmaceutically-acceptable carrier, diluent, excipient, or solvate.

6. The pharmaceutical composition as claimed in claim 1, in the form of a tablet, capsule, powder, granule, syrup, solution, or suspension.

7. A pharmaceutical composition which comprises a pharmaceutically-acceptable salt as claimed in claim 4 and a pharmaceutically-acceptable carrier, diluent, excipient, or solvate.

8. The pharmaceutical composition as claimed in claim 7, in the form of a tablet, capsule, powder, granule, syrup, solution, or suspension.

9. A method of treating pain, fever, or inflammation in a subject, said method comprising treating the subject having or susceptible to such disorder with a therapeutically-effective amount of a compound as claimed in claim 1 or a pharmaceutically acceptable salt thereof.

10. The method as claimed in claim 9, wherein the compound is administered orally, nasally, parenterally, topically, transdermally, or rectally.

11. A method of treating pain, fever, or inflammation in a subject, said method comprising treating the subject having or susceptible to such disorder with a therapeutically-effective amount of a pharmaceutically-acceptable salt as claimed in claim 4.

12. The method as claimed in claim 11, wherein the pharmaceutically-acceptable salt is administered orally, nasally, parenterally, topically, transdermally, or rectally.

13. The compound as claimed in claim 1 which is selected from the group consisting of:
- 5-(4-Fluorophenyl)-1-(4-methylsulfoximinylphenyl)-3-trifluoromethyl-1H-pyrazole;
- 5-(4-Chlorophenyl)-1-(4-methylsulfoximinylphenyl)-3-trifluoromethyl-1H-pyrazole;
- 5-(4-Methylphenyl)-1-(4-methylsulfoximinylphenyl)-3-trifluoromethyl-1H-pyrazole;
- 5-(4-Methoxyphenyl)-1-(4-methylsulfoximinylphenyl)-3-trifluoromethyl-1H-pyrazole;
- 1-(4-methylsulfoximinylphenyl)-5-(4-n-propoxyphenyl)-3-trifluoromethyl-1H-pyrazole;
- 5-(4-Ethoxyphenyl)-1-(4-methylsulfoximinylphenyl)-3-trifluoromethyl-1H-pyrazole;
- 5-(4-Hydroxyphenyl)-1-(4-methylsulfoximinylphenyl)-3-trifluoromethyl-1H-pyrazole;
- 5-(3-Chloro-4-fluorophenyl)-1-(4-methylsulfoximinylphenyl)-3-trifluoromethyl-1H-pyrazole;
- 5-(3,4-Difluorophenyl)-1-(4-methylsulfoximinylphenyl)-3-trifluoromethyl-1H-pyrazole;
- 5-(4-Fluoro-3-methylphenyl)-1-(4-methylsulfoximinylphenyl)-3-trifluoromethyl-1H-pyrazole;
- 5-(4-Methoxy-3-methylphenyl)-1-(4-methylsulfoximinylphenyl)-3-trifluoromethyl-1H-pyrazole;
- 5-(3-Chloro-4-methoxyphenyl)-1-(4-methylsulfoximinylphenyl)-3-trifluoromethyl-1H-pyrazole;
- 5-(3-Bromo-4-methoxyphenyl)-1-(4-methylsulfoximinylphenyl)-3-trifluoromethyl-1H-pyrazole;
- 5-(3-Fluoro-4-methoxyphenyl)-1-(4-methylsulfoximinylphenyl)-3-trifluoromethyl-1H-pyrazole;
- 5-(3-Methoxy-4-methylphenyl)-1-(4-methylsulfoximinylphenyl)-3-trifluoromethyl-1H-pyrazole;
- 1-(2-Fluoro-4-methylsulfoximinylphenyl)-5-(4-Methoxyphenyl)-3-trifluoromethyl-1H-pyrazole;
- 1-(3-Fluoro-4-methylsulfoximinylphenyl)-5-(4-Methoxyphenyl)-3-trifluoromethyl-1H-pyrazole;
- 1-(4-Methylsulfoximinylphenyl)-5-phenyl-3-trifluoromethyl-1H-pyrazole;
- 1-(4-Methylsulfoximinylphenyl)-5-(1-naphthyl)-3-trifluoromethyl-1H-pyrazole;
- 5-(4-Methoxyphenyl)-3-methyl-1-(4-methylsulfoximinylphenyl)-1H-pyrazole;
- 1-(4-Methylsulfoximinylphenyl)-5-(4-nitrophenyl)-3-trifluoromethyl-1H-pyrazole;
- 5-(3-Methoxyphenyl)-1-(4-methylsulfoximinylphenyl)-3-trifluoromethyl-1H-pyrazole;
- 5-(3,5-Difluoro-4-Methoxyphenyl)-1-(4-methylsulfoximinylphenyl)-3-trifluoromethyl-1H-pyrazole;
- 5-(3-Hydroxy-4-methoxyphenyl)-1-(4-methylsulfoximinylphenyl)-3-trifluoromethyl-1H-pyrazole;
- 5-(4-Methoxyphenyl)-1-(4-methylsulfoximinylphenyl)-1H-pyrazole-3-carboxylicacid;
- 3-(Hydroxymethyl)-5-(4-Methoxyphenyl)-1-(4-methylsulfoximinylphenyl)-1H-pyrazole;
- 5-(4-Methoxyphenyl)-1-(4-methylsulfoximinylphenyl)-1H-pyrazol-3-ylmethylhydrogen sulphate;
- 5-{4-(2-Hydroxy-ethoxy)phenyl}-1-(4-methylsulfoximinylphenyl)-3-trifluoromethyl-1H-pyrazole;
- 1-(4-Methylsulfoximinylphenyl)-5-(4-pyridyl)-3-trifluoromethyl-1H-pyrazole;
- 1-(4-Methylsulfoximinylphenyl)-5-(3-pyridyl)-3-trifluoromethyl-1H-pyrazole;
- 1-(4-Methylsulfoximinylphenyl)-5-(2-pyridyl)-3-trifluoromethyl-1H-pyrazole;
- 5-(4-Isopropoxyphenyl)-1-(4-methylsulfoximinylphenyl)-3-trifluoromethyl-1H-pyrazole;
- 1-(4-Methylsulfoximinylphenyl)-5-(2-thiophenyl)-3-trifluoromethyl-1H-pyrazole;
- 5-(4-Methylsulfoxyminylphenyl)-1-phenyl-3-trifluoromethyl-1H-pyrazole;
- 1-(4-Methoxyphenyl)-5-(4-methylsulfoximinylphenyl)-3-trifluoromethyl-1H-pyrazole;
- 5-Ethyl-4-(4-methylsulfoximinylphenyl)-3-phenyl-isoxazole;
- 5-Methoxymethyl-4-(4-methylsulfoximinylphenyl)-3-phenyl-isoxazole;
- 3-(4-Fluorophenyl)-5-methyl-4-(4-methylsulfoximinylphenyl)-isoxazole;
- 3-(4-Chlorophenyl)-5-methyl-4-(4-methylsulfoximinylphenyl)-isoxazole;
- 3-Ethyl-4-(4-methylsulfoximinylphenyl)-5-phenyl-isoxazole;
- 5-Chloro-4-(4-methylsulfoximinylphenyl)-3-phenyl-isoxazole;
- 5-Methyl-4-(4-methylsulfoximinylphenyl)-3-phenyl-isoxazole;
- 3-(4-Methoxyphenyl)-5-methyl-4-(4-methylsulfoximinylphenyl)-isoxazole;
- 5-Chloro-3-(4-methylsulfoximinylphenyl)-6'-methyl-[2,3']bipyridinyl;
- 5-Chloro-3-(4-methylsulfoximinylphenyl)-[2,3']bipyridinyl;
- 3-(3-Fluorophenyl)-4-(4-methylsulfoximinylphenyl)-3H-thiazol-2-one;
- 3-(3,4-Dichlorophenyl)-4-(4-methylsulfoximinylphenyl)-3H-oxazol-2-one;
- 3-(3,4-Dichlorophenyl)-4-(4-methylsulfoximinylphenyl)-3H-thiazol-2-one;
- 3-(2-Fluorophenyl)-4-(4-methylsulfoximinylphenyl)-3H-oxazol-2-one;
- 3-(4-Bromophenyl)-4-(4-methylsulfoximinylphenyl)-3H-oxazol-2-one;
- 4-(4-Methylsulfoximinylphenyl)-3-phenyl-3H-oxazol-2-one;
- 3-(3,4-Dichlorophenyl)-4-[4-(N-chloroacetyl)methylsulfoximinyl-phenyl]-3H-oxazol-2-one;
- 3-(3,4-Dichlorophenyl)-4-[4-(N-acetyl)methylsulfoximinyl-phenyl]-3H-oxazol-2-one;
- 3-(3,4-Dichlorophenyl)-4-[4-(N-methylsulfonyl)methylsulfoximinyl-phenyl]-3H-oxazol-2-one;
- 3-(3,4-Dichlorophenyl)-4-[4-{N-(4-methylphenyl)sulfonyl}-methylsulfoximinyl-phenyl]-3H-oxazol-2-one; and pharmaceutically-acceptable salts thereof.

14. The compound as claimed in claim 13, wherein the pharmaceutically acceptable salts are salts of tartaric acid, mandelic acid, fumaric acid, malic acid, lactic acid, maleic acid, salicylic acid, citric acid, ascorbic acid, benzene sulfonic acid, p-toluene sulfonic acid, hydroxynaphthoic acid, methane sulfonic acid, acetic acid, benzoic acid, succinic acid, palmitic acid, hydrochloric acid, hydrobromic acid, sulfuric acid, or nitric acid.

15. A pharmaceutical composition, which comprises a compound or pharmaceutically-acceptable salt thereof as claimed in claim 13, and a pharmaceutically acceptable carrier, diluent, excipient, or solvate.

16. The pharmaceutical composition as claimed in claim 15, in the form of a tablet, capsule, powder, granules, syrup, solution, or suspension.

17. A method of treating pain, fever, or inflammation in a subject, said method comprising treating the subject having or susceptible to such disorder with a therapeutically-effective amount of a compound or pharmaceutically acceptable salt thereof as claimed in claim 13.

18. A process for preparing a compound of formula (I),

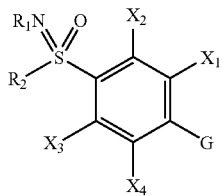

(I)

wherein G represents one of A, B, C, E, or F as desenbed below:

G =

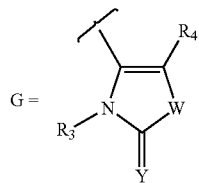  A

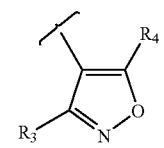  B

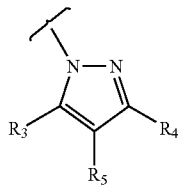  C

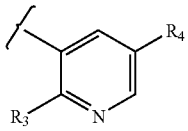  E

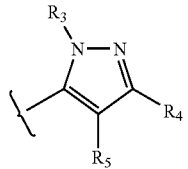  F $R_1$ represents hydrogen, substituted or unsubstituted groups selected from the group consisting of alkyl, aralkyl, acyl, alkylsulfonyl, and arylsulfonyl groups; $R_2$ represents alkyl, aralkyl, or —NHR or —OR where R represents hydrogen or a lower alkyl group which may be suitably substituted; $X_1$, $X_2$, $X_3$, and $X_4$ may be same or different and represent hydrogen, cyano, nitro, halo, carboxyl, formyl, hydrazino, azido, amino, thio, hydroxy, or a substituted or unsubstituted group selected from the group consisting of alkyl which may be linear or branched, alkenyl, oximealkyl, alkoxy, haloalkoxy, hydroxyalkyl, alkoxyalkyl, thioalkyl, carboxyalkyl, haloalkyl, aminoalkyl, cyanoalkyl, alkylthio, alkylsulfinyl, alkylsulfonyl, alkoxycarbonylalkyl, acyl, acyloxy, acyloxyalkyl, aralkyl, aryloxy, aralkoxy, aryloxyalkyl, aralkoxyalkyl, aralkenyl, acylamino, alkylamino, dialkylamino, aralkylamino, alkoxyamino, hydroxylamino, alkoxycarbonyl, and aralkoxycarbonyl groups; when G represents heterocycle "D", then at least one of $X_1$, $X_2$, $X_3$, and $X_4$ is not hydrogen; $R_3$ represents a substituted or unsubstituted alkyl, or a substituted or unsubstituted, single or fused group selected from the group consisting of aryl, aralkenyl, heteroaryl, and heterocyclic groups; $R_4$ and $R_5$ represent hydrogen atom, halogen atom, carboxy, or a substituted or unsubstituted group selected from the group consisting of linear or branched alkyl, alkoxycarbonyl, hydroxyalkyl, alkoxyalkyl, and phenyl groups; Y represents O or S; and W represents O or S;

said process comprising: (a) oxidizing a compound of formula (P) to produce a compound of formula (Q) and (b) iminating the compound of formula (Q) to produce a compound of formula (I)

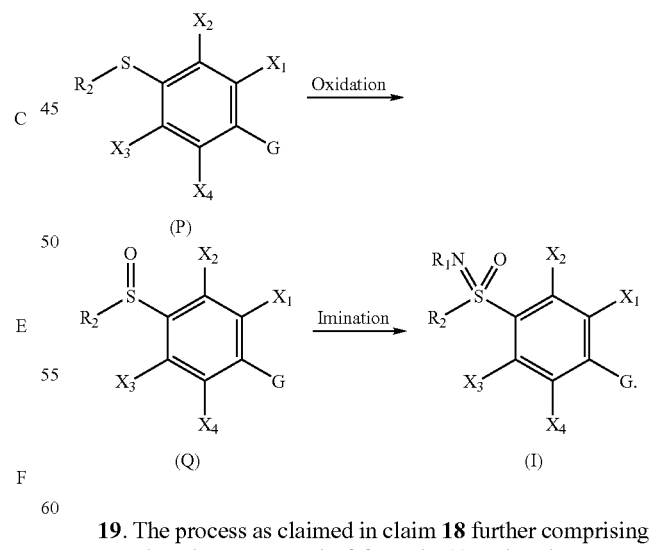

19. The process as claimed in claim 18 further comprising converting the compound of formula (I) to its pharmaceutically-acceptable salt.

* * * * *